(12) United States Patent
Sumino et al.

(10) Patent No.: US 9,650,394 B2
(45) Date of Patent: May 16, 2017

(54) METHODS OF PRODUCING SUBSTITUTED (3S,11AR)-6-HYDROXY-3-METHYL-5,7-DIOXO-2,3,5,7,11,11A-HEXAHYDROOXAZOLO[3,2-A]PYRIDO[1,2-D]PYRAZINE-8-CARBOXAMIDES

(71) Applicant: Shionogi & Co., Ltd., Osaka-shi, Osaka (JP)

(72) Inventors: Yukihito Sumino, Osaka (JP); Moriyasu Masui, Osaka (JP); Daisuke Yamada, Osaka (JP); Fumiya Ikarashi, Osaka (JP); Kazuya Okamoto, Osaka (JP)

(73) Assignee: Shionogi & Co., Ltd. (JP)

( * ) Notice: Subject to any disclaimer, the term of this patent is extended or adjusted under 35 U.S.C. 154(b) by 0 days.

(21) Appl. No.: 15/072,388

(22) Filed: Mar. 17, 2016

(65) Prior Publication Data

US 2016/0229870 A1 Aug. 11, 2016

Related U.S. Application Data

(62) Division of application No. 14/518,209, filed on Oct. 20, 2014, now Pat. No. 9,321,789, which is a division of application No. 13/814,333, filed as application No. PCT/JP2011/067832 on Aug. 4, 2011, now abandoned.

(30) Foreign Application Priority Data

Aug. 5, 2010 (JP) .................................. 2010-175899
Dec. 14, 2010 (JP) .................................. 2010-277713

(51) Int. Cl.
*C07D 498/14* (2006.01)
*A61K 31/5365* (2006.01)
*C07D 213/80* (2006.01)

(52) U.S. Cl.
CPC ........ *C07D 498/14* (2013.01); *A61K 31/5365* (2013.01); *C07D 213/80* (2013.01)

(58) Field of Classification Search
CPC .................................................... C07D 498/14

USPC ......................................................... 544/346
See application file for complete search history.

(56) References Cited

FOREIGN PATENT DOCUMENTS

| JP | 2008-540343 A | 11/2008 |
|---|---|---|
| WO | 2010/011812 A1 | 1/2010 |
| WO | 2010/011819 A1 | 1/2010 |
| WO | 2010/068253 A | 6/2010 |
| WO | 2010/110409 A1 | 9/2010 |
| WO | 2011/119566 A1 | 9/2011 |

OTHER PUBLICATIONS

Shinogi & Co., Ltd., Extended European Search Report dated Nov. 29, 2013, Application No. 11814690.1-1452/2602260 PCT/JP2011067832.

*Primary Examiner* — Douglas M Willis
(74) *Attorney, Agent, or Firm* — J. Scott Young

(57) ABSTRACT

A process for preparing a compound represented by formula (Y1) or (Y2)

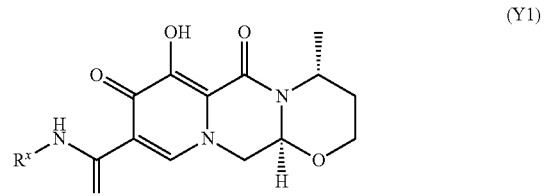

(Y1)

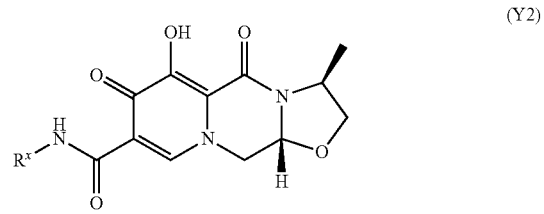

(Y2)

wherein $R^x$ is an optionally substituted carbocyclyl lower alkyl, or the like or a salt thereof, using a novel process for preparing a pyridone derivative represented by formula (X4) wherein $R^{1d}$, $R^{2d}$, and $R^{4d}$ are as defined herein.

7 Claims, 3 Drawing Sheets

METHODS OF PRODUCING SUBSTITUTED (3S,11AR)-6-HYDROXY-3-METHYL-5,7-DIOXO-2,3,5,7,11,11A-HEXAHYDROOXAZOLO[3,2-A]PYRIDO[1,2-D]PYRAZINE-8-CARBOXAMIDES

CROSS-REFERENCE TO RELATED APPLICATIONS

This application is filed as a divisional application of U.S. Ser. No. 14/518,209 filed on Oct. 20, 2014, which is a divisional application of U.S. Ser. No. 13/814,333 filed on Aug. 4, 2011, now abandoned, which was filed pursuant to 35 USC 371 as a United States National Phase Application of International Patent Application Serial No. PCT/JP2011/067832 filed on Aug. 4, 2011, which claims priority from 2010-175899 filed on Aug. 5, 2010 and 2010-277713 filed on Dec. 14, 2010 in Japan.

TECHNICAL FIELD

The present invention relates to a method of producing compounds having HIV integrase inhibitory activity, using a novel method of producing pyrone derivatives and pyridone derivatives.

BACKGROUND ART

Patent Document 1 describes compounds (I) and (II), which are useful as anti-HIV drugs and shown by formulae:

[Chemical formula 1]

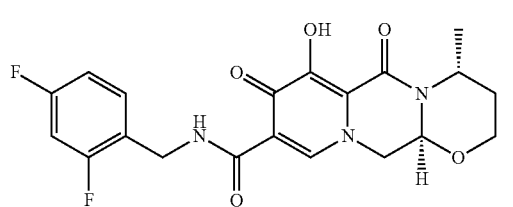
(I)

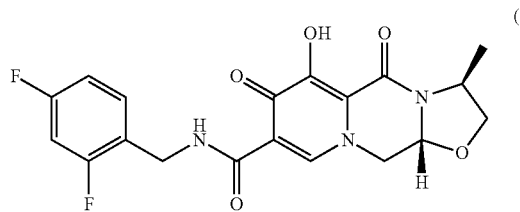
(II)

This document describes the following reaction formula as a method of producing compound (I).

[Chemical formula 2]

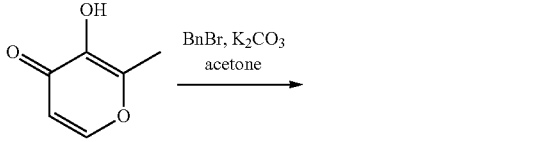

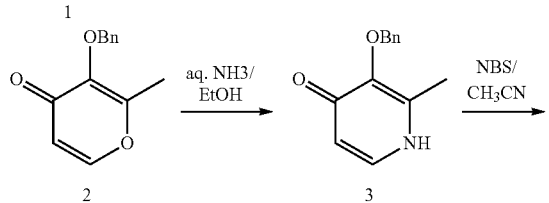

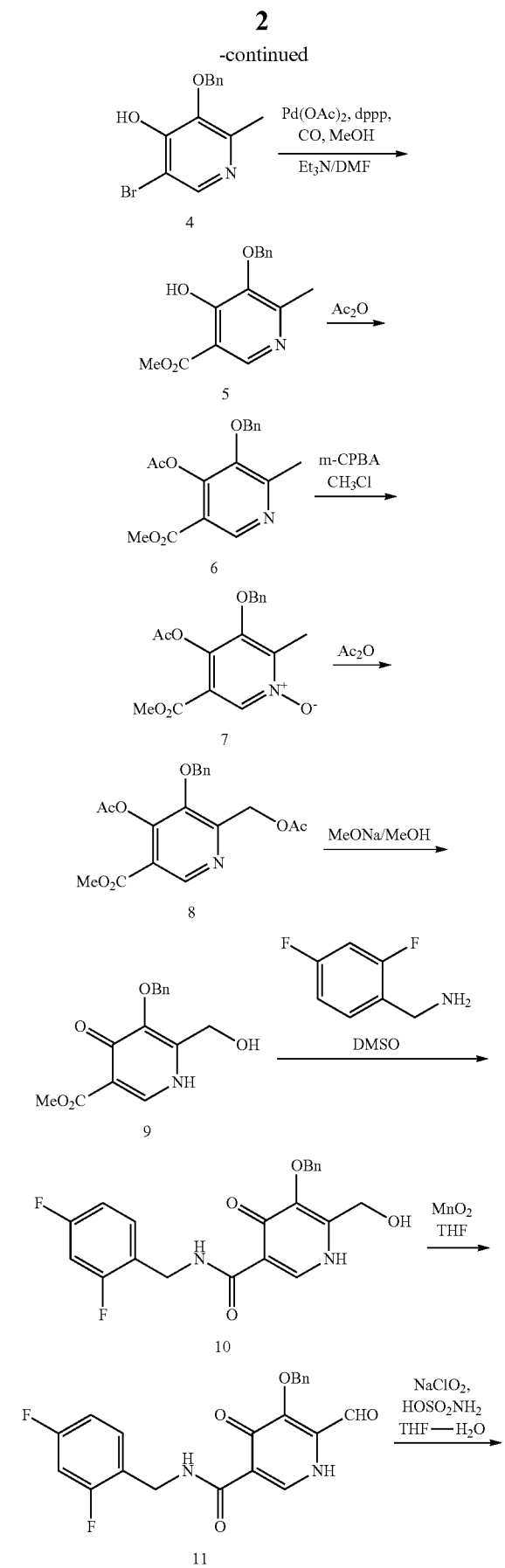

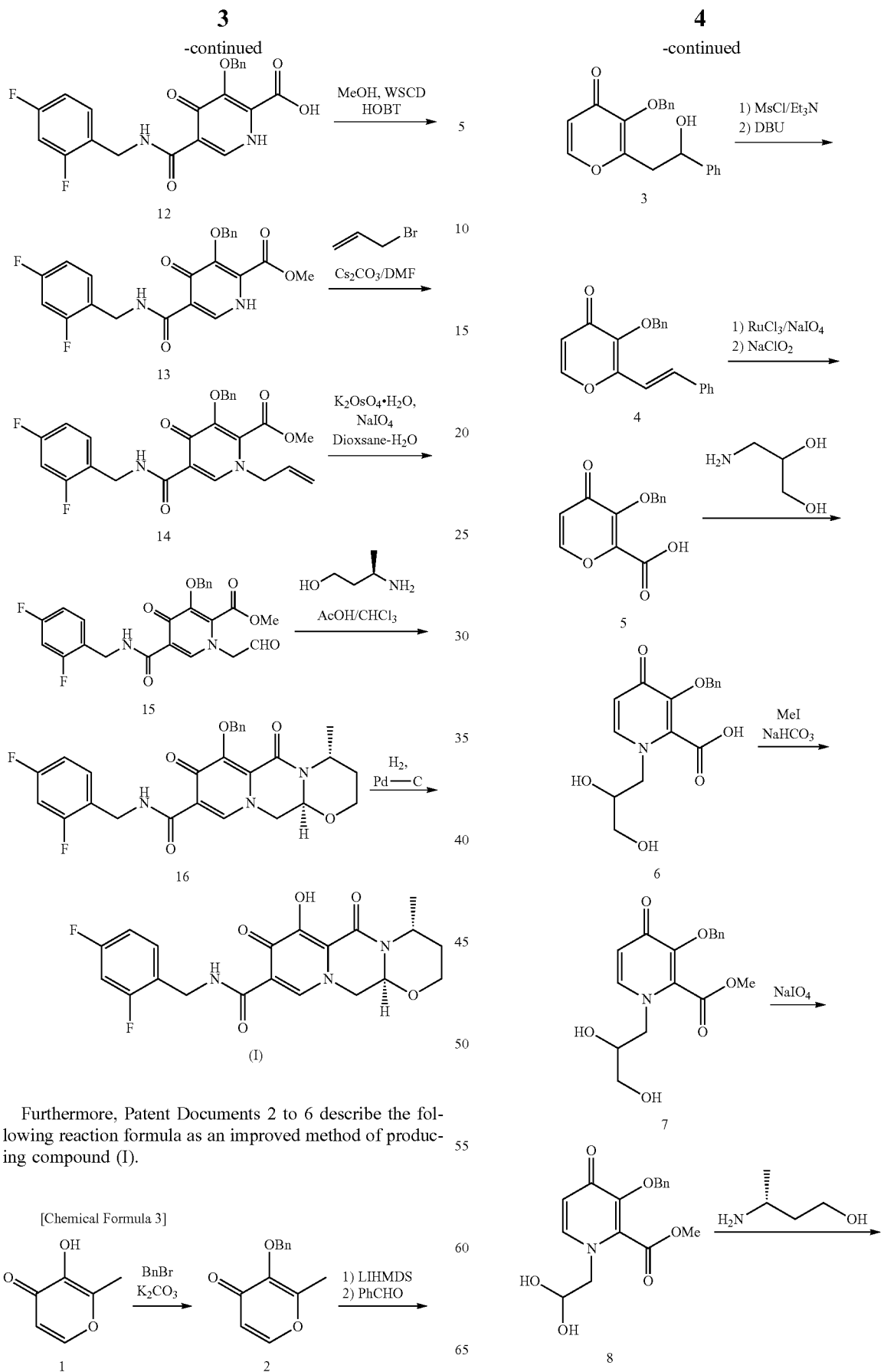
Furthermore, Patent Documents 2 to 6 describe the following reaction formula as an improved method of producing compound (I).
[Chemical Formula 3]

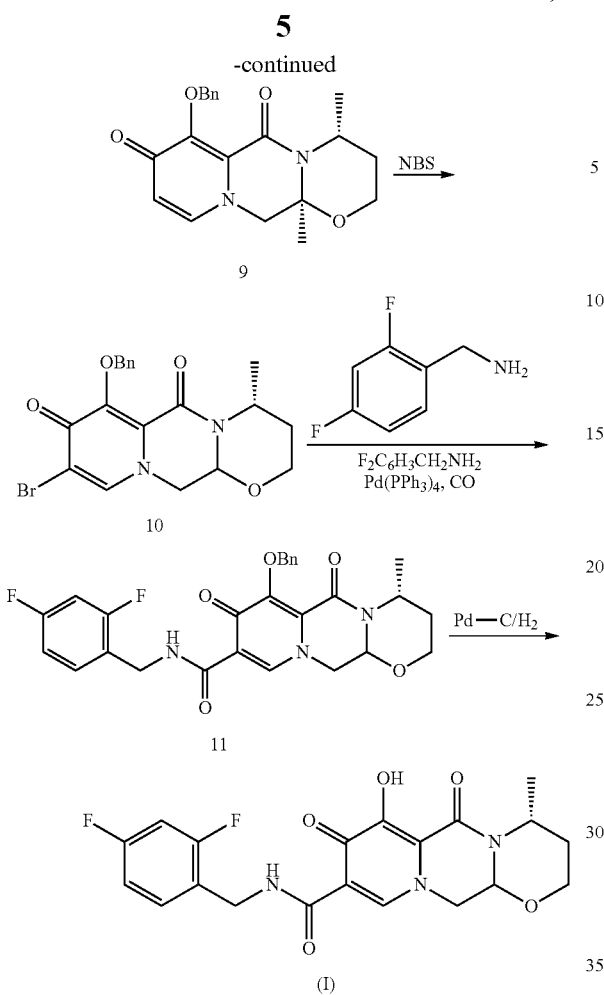

However, the above production methods of these documents are not satisfactory for the industrial manufacturing method because of the followings:

these reaction processes for obtaining compound (I) include 16 or 11 steps, respectively, and are very long, the total yield is low, thus being inefficient, a high toxic and harmful reaction is used.

an expensive reagent is used, an environmentally harmful reagent is used.

Therefore, the development of a method for more efficient industrial mass-production of compound (I), compound (II) and their derivatives has been desired.

Non-Patent Documents 1 and 2 describe a method of producing pyrane-4-one and pyridine 4-one. Patent Document 7 and Non-Patent Document 3 describe a method of producing enaminone derivatives. However, a method of producing pyronediester and pyridonediester of the present invention is not described in these documents. Furthermore, a method of manufacturing compounds having HIV-integrase inhibitory activity by using the production method of the present invention is not disclosed. Patent Document 8 is an international patent application by the present applicant. Though this document describes the method of producing pyronediester and pyridonediester identical to the present invention, compounds having HIV-integrase inhibitory activity and anti-HIV drugs are not described therein.

PRIOR ART DOCUMENTS

Patent Documents

[Patent Document 1] International publication No. 2006/116764 pamphlet
[Patent Document 2] International publication No. 2010/011812 pamphlet
[Patent Document 3] International publication No. 2010/011819 pamphlet
[Patent Document 4] International publication No. 2010/068262 pamphlet
[Patent Document 5] International publication No. 2010/067176 pamphlet
[Patent Document 6] International publication No. 2010/068253 pamphlet
[Patent Document 7] U.S. Pat. No. 4,769,380A
[Patent Document 8] International application PCT/JP2010/055316

Non-Patent Documents

[Non-Patent Document 1] Journal of Organic Chemistry, 1991, 56(16), 4963-4967
[Non-Patent Document 2] Science of Synthesis, 2005, 15, 285-387
[Non-Patent Document 3] Journal of Chemical Society Parkin Transaction. 1, 1997, Issue. 2, 163-169

SUMMARY OF THE INVENTION

Problem to be Solved by the Invention

An object of the present invention is to efficiently produce compounds useful as an anti-HIV drug having HIV-integrase inhibitory activity, which are shown by formula (Y1) or formula (Y2), a pharmaceutically acceptable salt thereof, or their solvate, by using a novel pyrone derivative and a pyridone derivative, a method of producing the same, and a method of using the same:

[Chemical formula 4]

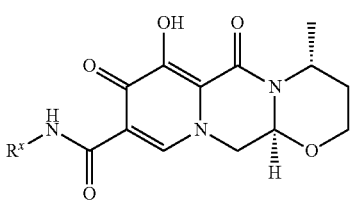

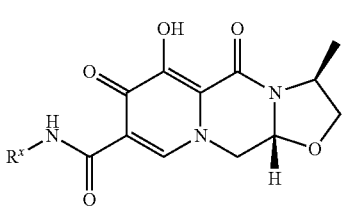

(wherein is carbocyclyl optionally substituted by substituent E, heterocyclyl optionally substituted by substituent E, carbocyclyl lower alkyl optionally substituted by substituent E, or heterocyclyl lower alkyl optionally substituted by substituent E.

Substituent E: halogen, cyano, hydroxy, carboxy, formyl, amino, oxo, nitro, lower alkyl, halogeno lower alkyl, lower alkyloxy, carbocyclyl optionally substituted by substituent F, heterocyclyl optionally substituted by substituent F, carbocyclyl lower alkyloxy optionally substituted by substituent F, heterocyclyl lower alkyloxy optionally substituted by substituent F, carbocyclyl lower alkylthio optionally substituted by substituent F, heterocyclyl lower alkylthio optionally substituted by substituent F, carbocyclyl lower alkylamino optionally substituted by substituent F, heterocyclyl lower alkylamino optionally substituted by substituent F, carbocyclyloxy optionally substituted by substituent F, heterocyclyloxy optionally substituted by substituent F, carbocyclylcarbonyl optionally substituted by substituent F, heterocyclylcarbonyl optionally substituted by substituent F, carbocyclylaminocarbonyl optionally substituted by substituent F, heterocyclylaminocarbonyl optionally substituted by substituent F, halogeno lower alkyloxy, lower alkyloxy lower alkyl, lower alkyloxy lower alkyloxy, lower alkylcarbonyl, lower alkyloxycarbonyl, lower alkyloxycarbonylamino, lower alkylamino, lower alkylcarbonylamino, lower alkylaminocarbonyl, lower alkylsulfornyl, and lower alkylsulfornylamino;

Substituent F: halogen, hydroxy, carboxy, amino, oxo, nitro, lower alkyl, halogeno lower alkyl, lower alkyloxy, and amino protective group)

Means for Solving the Problems

The prevent invention provides the following items, which relate to a production method shown by the following reaction formula:

[Chemical formula 5]

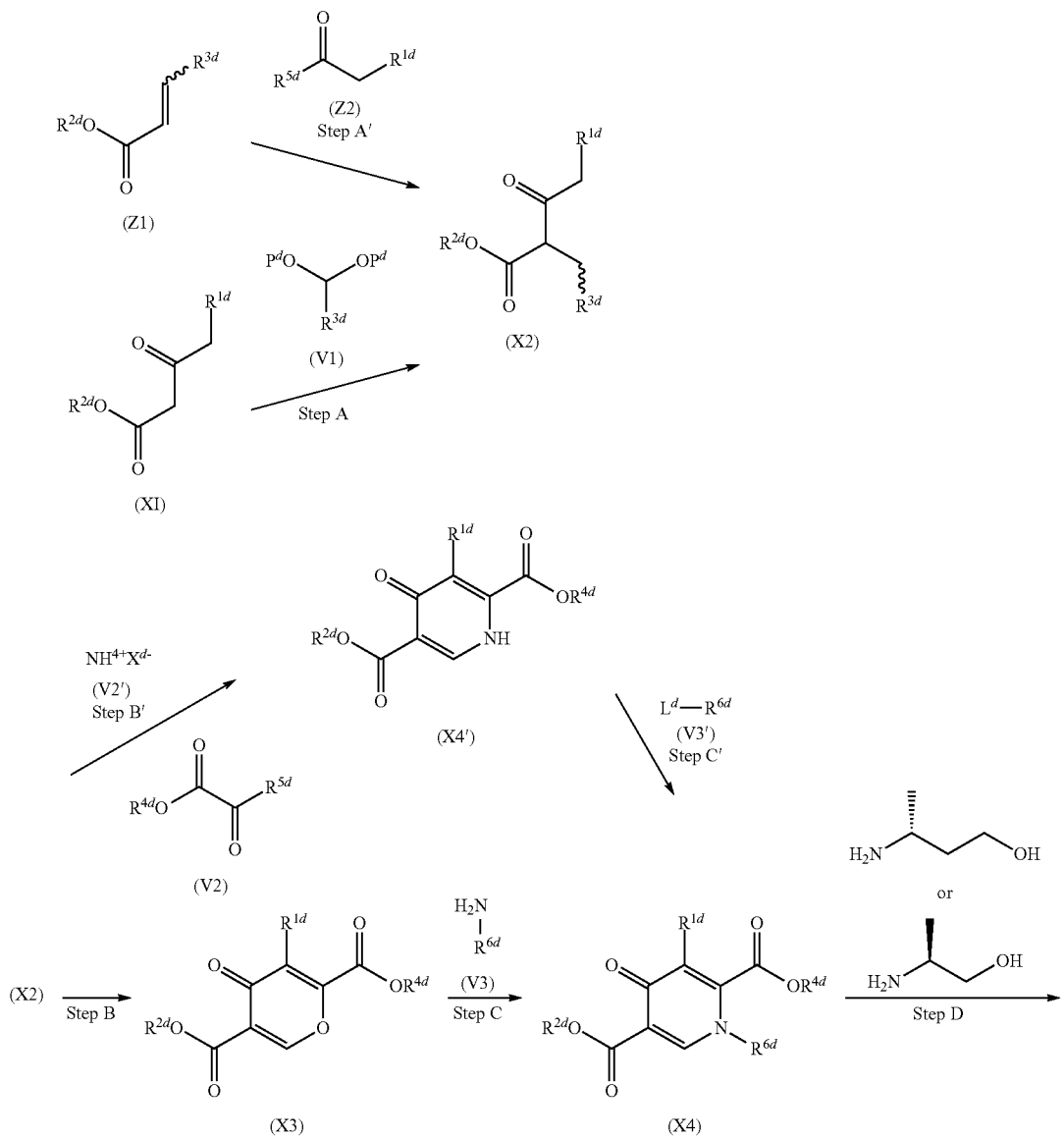

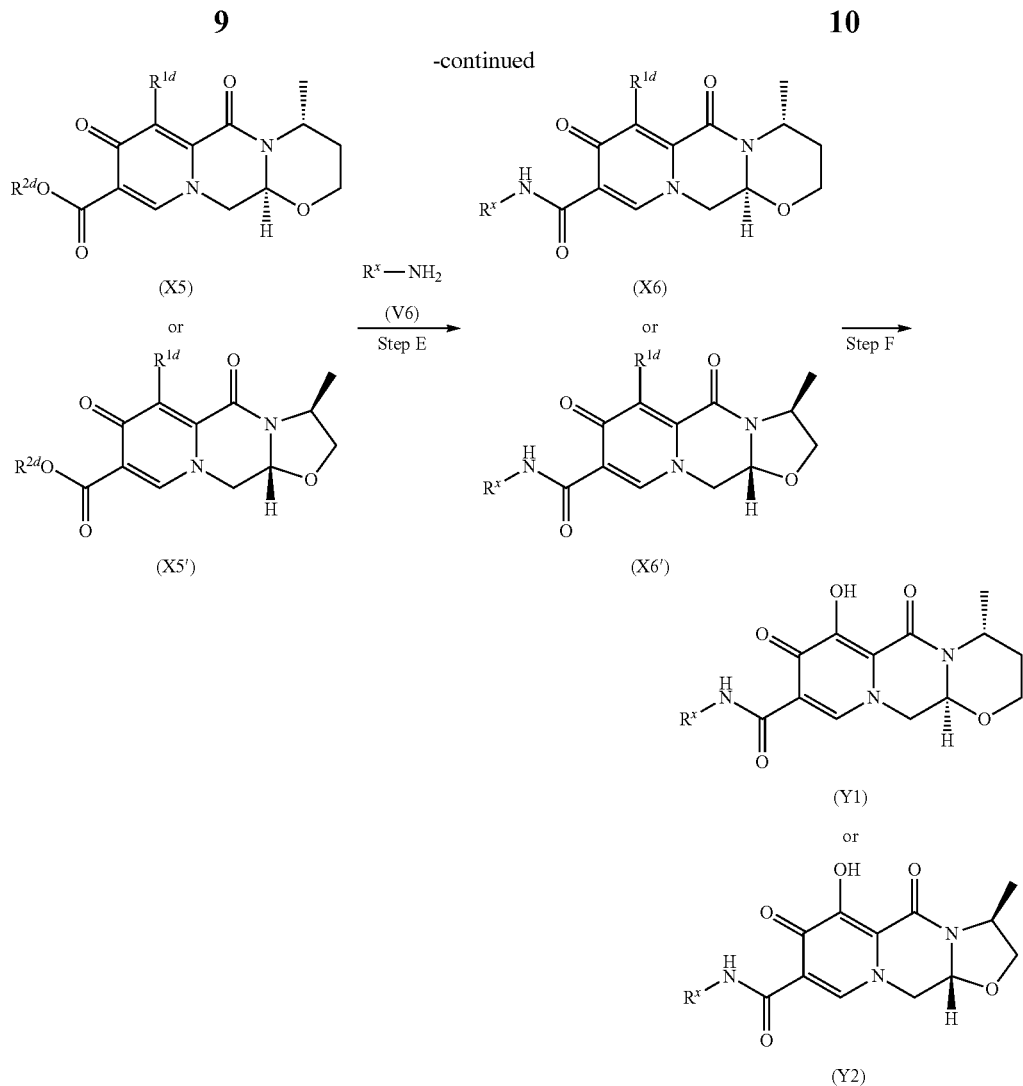

(Item 1)

A method of producing a compound shown by formula (Y1) or formula (Y2) or a salt thereof:

[Chemical formula 6]

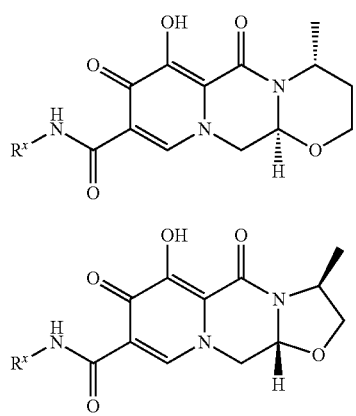

(wherein $R^x$ is carbocyclyl optionally substituted by substituent E, heterocyclyl optionally substituted by substituent E, carbocyclyl lower alkyl optionally substituted by substituent E, or heterocyclyl lower alkyl optionally substituted by substituent E, and substitutent E is as defined below) comprising a step of:

(Step B)

reacting a compound shown by formula (X2):

[Chemical formula 7]

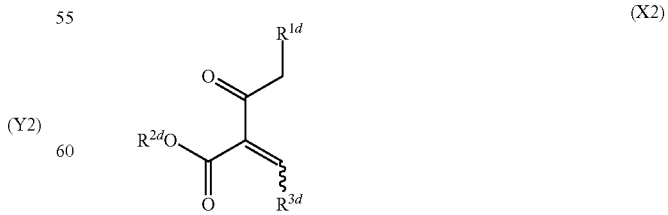

(wherein, $R^{1d}$ is hydrogen, halogen, lower alkyloxy optionally substituted by substituent E, carbocyclyl lower alkyloxy optionally substituted by substituent E, heterocyclyl lower alkyloxy optionally substituted by substituent E, or —OSi($R^{1e}$)$_3$, $R^{1e}$s are each independently lower alkyl optionally substituted by substituent E, carbocyclyl optionally substituted by substituent E, heterocyclyl optionally substituted by substituent E, carbocyclyl lower alkyl optionally substituted by substituent E, or heterocyclyl lower alkyl optionally substituted by substituent E, $R^{2d}$ is hydrogen, lower alkyl optionally substituted by substituent E, carbocyclyl lower alkyl optionally substituted by substituent E, or heterocyclyl lower alkyl optionally substituted by substituent E, $R^{3d}$ is hydrogen, lower alkyloxy optionally substituted by substituent E, —N($R^{3e}$)$_2$, or —O$R^{3e}$, $R^{3e}$s are each independently lower alkyl optionally substituted by substituent E, or two $R^{3e}$s in —N($R^{3e}$)$_2$ together with the adjacent nitrogen atom may form a heterocycle, and a wavy line means E form and/or Z form or a mixture thereof.

Substituent E: halogen, cyano, hydroxyl, carboxy, formyl, amino, oxo, nitro, lower alkyl, halogeno lower alkyl, lower alkyloxy, carbocyclyl optionally substituted by substituent F, heterocyclyl optionally substituted by substituent F, carbocyclyl lower alkyloxy optionally substituted by substituent F, heterocyclyl lower alkyloxy optionally substituted by substituent F, carbocyclyl lower alkylthio optionally substituted by substituent F, heterocyclyl lower alkylthio substituted by substituent F, carbocyclyl lower alkylamino optionally substituted by substituent F, heterocyclyl lower alkylamino optionally substituted by substituent F, carbocyclyloxy optionally substituted by substituent F, heterocyclyloxy optionally substituted by substituent F, carbocyclylcarbonyl optionally substituted by substituent F, heterocyclylcarbonyl optionally substituted by substituent F, carbocyclylaminocarbonyl optionally substituted by substituent F, heterocyclylaminocarbonyl optionally substituted by substituent F, halogeno lower alkyloxy, lower alkyloxy lower alkyl, lower alkyloxy lower alkyloxy, lower alkylcarbonyl, lower alkyloxycarbonyl, lower alkyloxy carbonylamino, lower alkylamino, lower alkylcarbonylamino, lower alkylaminocarbonyl, lower alkylsulfonyl, and lower alkylsulfornylamino;

Substituent F: halogeno, hydroxyl, carboxy, amino, oxo, nitro, lower alkyl, halogeno lower alkyl, lower alkyloxy, and amino protecting group)

with a compound shown by formula (V2):

[Chemical formula 8]

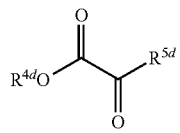

(V2)

(wherein,
$R^{4d}$ is lower alkyl optionally substituted by substituent E, carbocyclyl lower alkyl optionally substituted by substituent E, or heterocyclyl lower alkyl optionally substituted by substituent E,
$R^{5d}$ is hydrogen, halogen, lower alkyloxy optionally substituted by substituent E, or —O—SO$_2$—$R^{5e}$,
$R^{5e}$ is lower alkyl optionally substituted by substituent E, carbocyclyl optionally substituted by substituent E, heterocyclyl optionally substituted by substituent E, carbocyclyl lower alkyl optionally substituted by substituent E, or heterocyclyl lower alkyl substituted by substituent E, and Substituent E is as defined above)

to obtain a compound shown by formula (X3) or a salt thereof:

[Chemical formula 9]

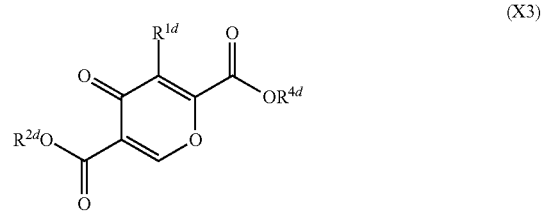

(X3)

(wherein each symbol is as defined above).

(Item 2)

A method of producing a compound shown by formula (Y1) or formula (Y2), or a salt thereof:

[Chemical formula 10]

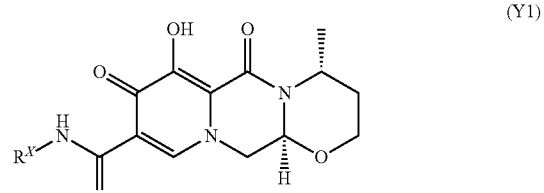

(Y1)

(Y2)

(wherein $R^x$ is as defined in Item 1)

comprising a step of:

(Step C)

reacting a compound shown by formula (X3), or a salt thereof:

[Chemical formula 11]

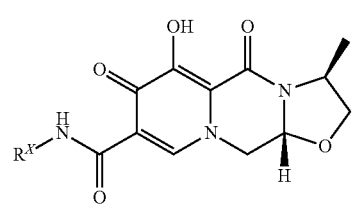

(X3)

(wherein each symbol is as defined above).

with a compound shown by formula (V3), or a salt thereof:

[Chemical formula 12]

H$_2$N—$R^{6d}$ (V3)

(wherein $R^{6d}$ is lower alkyl optionally substituted by substituent E, or lower alkenyl optionally substituted by substituent E, and substituent E is as defined in Item 1).

to obtain a compound shown by formula (X4), or a salt thereof:

[Chemical formula 13]

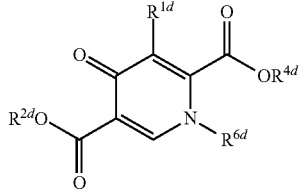
(X4)

(wherein each symbol is as defined in Item 1 or above).

(Item 3)

A method of producing of a compound shown by formula (Y1) or formula (Y2), or a salt thereof:

[Chemical formula 14]

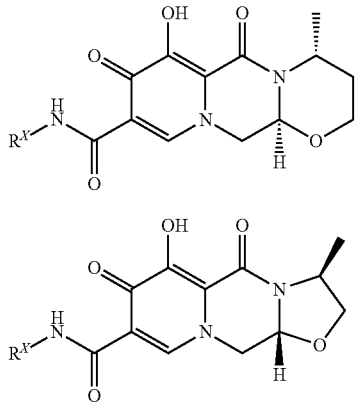
(Y1)
(Y2)

(wherein each symbol is as defined in Item 1)

comprising a step of:

(Step D)

reacting a compound shown by formula (X4), or a salt thereof:

[Chemical formula 15]

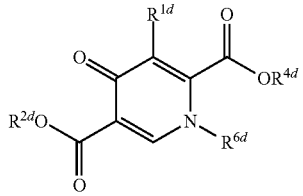
(X4)

(wherein each symbol is as defined in Item 1 or Item 2) with (R)-3-amino-butan-1-ol, or (S)-2-amino-propan-1-ol to obtain a compound shown by formula (X5) or formula (X5'):

[Chemical formula 16]

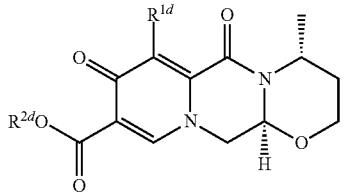
(X5)

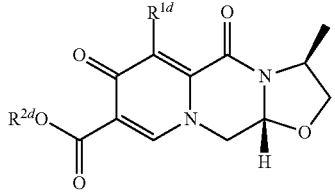
(X5')

(wherein each symbol is as defined in Item 1).

(Item 4)

A method according to Item 1 comprising a step of:

(Step C)

reacting a compound shown by formula (X3), or a salt thereof:

[Chemical formula 17]

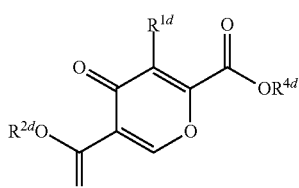
(X3)

(wherein each symbol is as defined in Item 1)

with a compound shown by formula (V3), or a salt thereof:

[Chemical formula 18]

$$H_2N—R^{6d}$$ (V3)

(wherein $R^{6d}$ is as defined in Item 2)

to obtain a compound shown by formula (X4), or a salt thereof:

[Chemical formula 19]

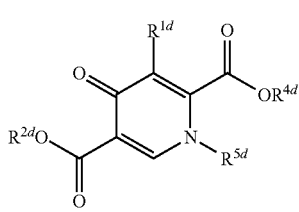
(X4)

(wherein each symbol is as defined in Item 1 or Item 2).

(Item 5)

A method according to Item 4 comprising a step of:

(Step D)

reacting a compound shown by formula (X4), or a salt thereof:

[Chemical formula 20]

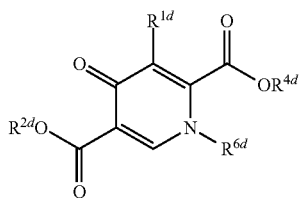
(X4)

(wherein each symbol is as defined in Item 1 or Item 2) with (R)-3-amino-butan-1-ol, or (S)-2-amino-propan-1-ol to obtain a compound shown by formula (X5) or formula (X5'), or a salt thereof:

[Chemical formula 21]

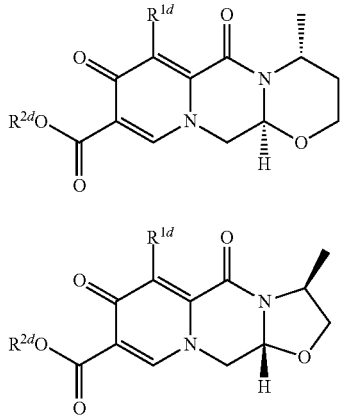

(wherein each symbol is as defined in Item 1).

(Item 6)

A method according to Item 3 or 5 comprising a step of:

(Step E)

reacting a compound shown by formula (X5) or formula (X5'), or a salt thereof:

[Chemical formula 22]

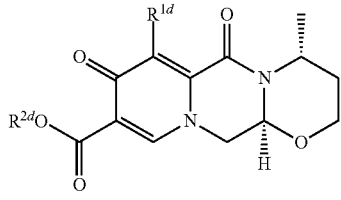
(X5)

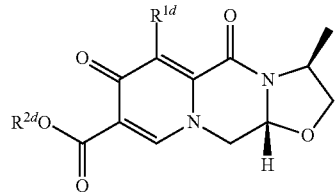
(X5')

(wherein each symbol is as defined in Item 1) with a compound shown by formula (V6), or a salt thereof:

[Chemical formula 23]

$$R^x-NH_2 \quad (V6)$$

(wherein $R^x$ is as defined in Item 1) to obtain a compound shown by formula (X6) or formula (X6'), or a salt thereof:

[Chemical formula 24]

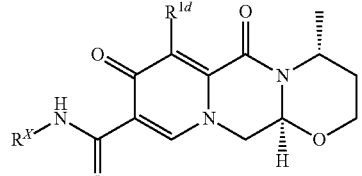
(X6)

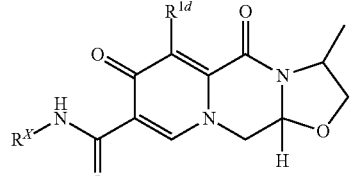
(X6')

(wherein each symbol is as defined in Item 1).

(Item 7)

A method according to Item 4, 5 or 6, wherein Step B and Step C are continuously performed.

(Item 8)

A method of producing of a compound shown by formula (Y1) or formula (Y2), or a salt thereof:

[Chemical formula 25]

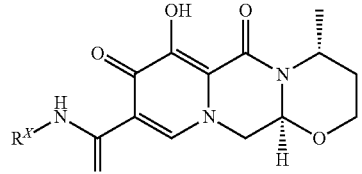
(Y1)

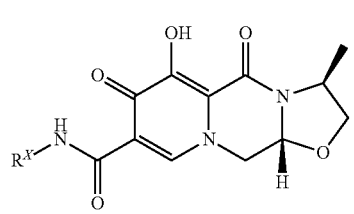
(Y2)

(wherein $R^x$ is as defined in Item 1)
comprising a step of:
(Step B')
reacting a compound shown by formula (X2):

[Chemical formula 26]

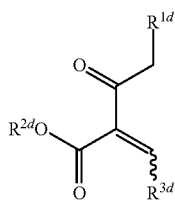
(X2)

(wherein each symbol is as defined in Item 1)
with a compound shown by formula (V2):

[Chemical formula 27]

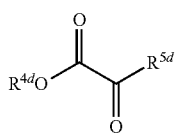
(V2)

(wherein each symbol is as defined in Item 1)
and a compound shown by formula (V2'):

[Chemical formula 28]

$NH_4^+ X^{d-}$ (V2')

(wherein $X^{d-}$ is a counter anion of ammonium cation)
to obtain a compound shown by formula (X4'), or a salt thereof:

[Chemical formula 29]

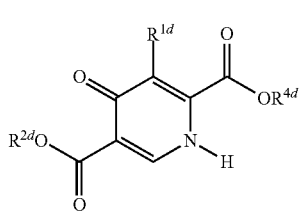
(X4')

(wherein each symbol is as defined in Item 1).
(Item 9)
A method according to Item 8 comprising a step of:
(Step C')
reacting a compound shown by formula (X4'):

[Chemical formula 30]

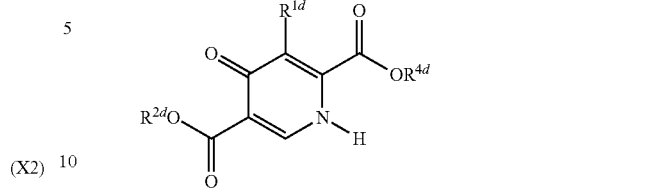
(X4')

(wherein each symbol is as defined in Item 1)
with a compound shown by formula (V3'):
[Chemical formula 31]

$R^{6d}\text{-}L^d$ (V3')

(wherein $R^{6d}$ is as defined in Item 2, $L^d$ is a leaving group)
to obtain a compound shown by formula (X4), or a salt thereof:

[Chemical formula 32]

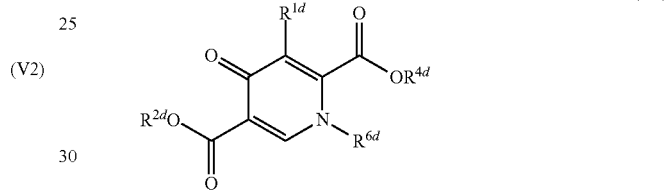
(X4)

(wherein each symbol is as defined in Item 1 or 2).
(Item 10)
A method according to Item 9 comprising a step of:
(Step D)
reacting a compound shown by formula (X4):

[Chemical formula 33]

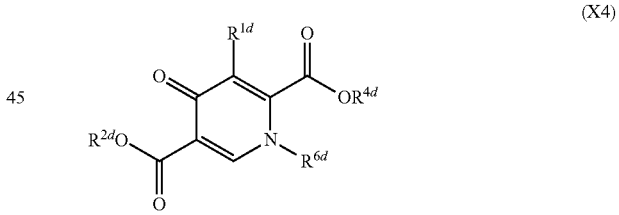
(X4)

(wherein each symbol is as defined in Item 1 or Item 2)
with (R)-3-amino-butan-1-ol or (S)-2-amino-propan-1-ol to obtain a compound shown by formula (X5) or formula (X5'), or a salt thereof:

[Chemical formula 34]

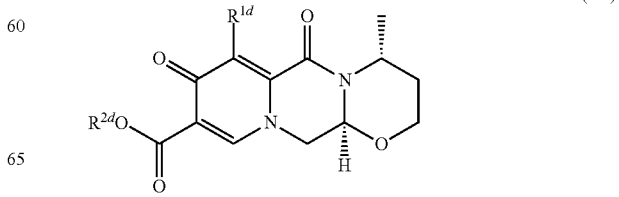
(X5)

-continued

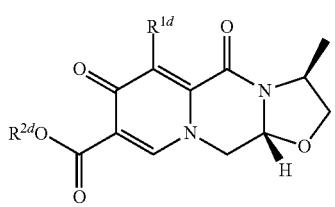
(X5')

(wherein each symbol is as defined in Item 1).
(Item 11)
A method according to Item 10 comprising a step of:
(Step E)
reacting a compound shown by formula (X5) or formula (X5'):

[Chemical formula 35]

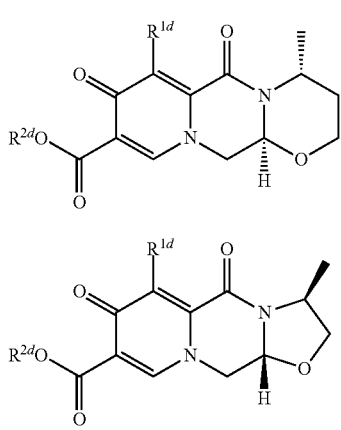
(X5)

(X5')

(wherein each symbol is as defined in Item 1)
with a compound shown by formula (V6), or a salt thereof:
[Chemical formula 36]

$R^x$—NH$_2$   (V6)

(wherein $R^x$ is as defined in Item 1)
to obtain a compound shown by formula (X6) or formula (X6'), or a salt thereof:

[Chemical formula 37]

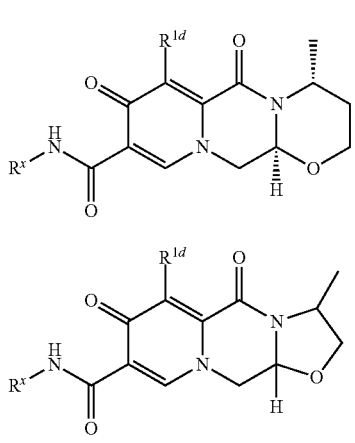
(X6)

(X6')

(wherein each symbol is as defined in Item 1).
(Item 12)
A method according to Item 1, or any one of Items 4 to 11, wherein the compound shown by formula (X2) is obtained by reacting a compound shown by formula (X1):

[Chemical formula 38]

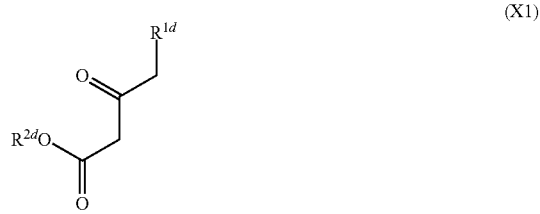
(X1)

(wherein each symbol is as defined in Item 1)
with a compound shown by formula (V1):

[Chemical formula 39]

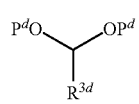
(V1)

(wherein $P^d$ is lower alkyl optionally substituted by substituent E, and $R^{3d}$ and substituent E are as defined in Item 1).
(Item 13)
A method according to Item 1 or any one of Items 4 to 11, wherein the compound shown by formula (X2) is obtained by reacting a compound shown by formula (Z1):

[Chemical formula 40]

(Z1)

(wherein each symbol is as defined in Item 1)
with a compound shown by formula (Z2):

[Chemical formula 41]

(Z2)

(wherein each symbol is as defined in Item 1).
(Item 14)
A method according to any one of Items 1 to 13, wherein $R^x$ is carbocyclyl lower alkyl optionally substituted by substituent E.
(Item 15)
A method according to any one of Items 1 to 13, wherein $R^x$ is 2,4-difluorobenzyl.
(Item 16)
A method of producing a compound shown by formula (Y1) or formula (Y2), or a salt thereof:

[Chemical formula 42]

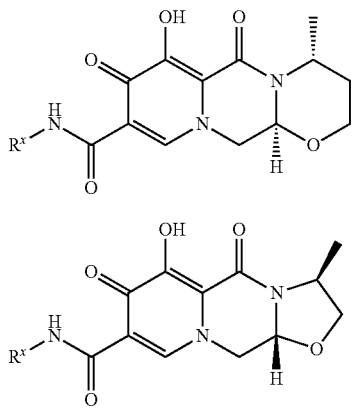

(Y1)

(Y2)

(wherein $R^x$ is as defined in Item 1)
comprising steps of:
(Step C″)
reacting a compound shown by formula (W1):

[Chemical formula 43]

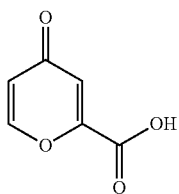

(W1)

with a compound shown by formula (V3), or a salt thereof:
[Chemical formula 44]

$H_2N—R^{6d}$  (V3)

(wherein $R^{6d}$ is as defined in Item 2)
to obtain a compound shown by formula (W2), or a salt thereof:

[Chemical formula 45]

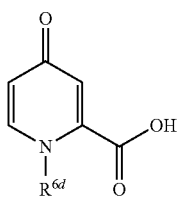

(W2)

(wherein $R^{6d}$ is as defined in Item 2), and
(Step D″)
reacting a compound shown by formula (W2) with (R)-3-amino-burane-1-ol or (S)-2-amino-propan-1-ol to obtain a compound shown by formula (W3) or formula (W4), or a salt thereof:

[Chemical formula 46]

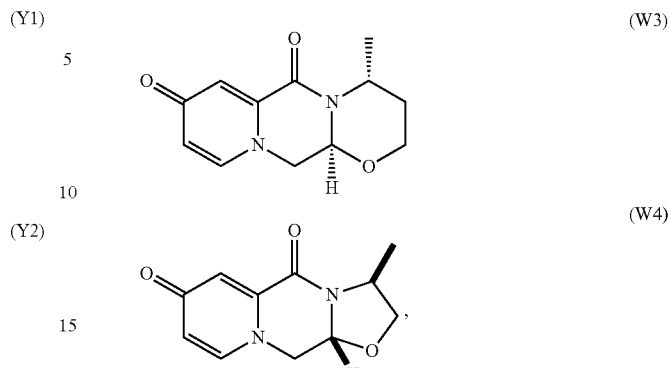

(W3)

(W4)

and
(Step F)
reacting a compound shown by formula (W3) or formula (W4) with a halogenating agent to obtain a compound shown by formula (W5) or formula (W6), or a salt thereof:

[Chemical formula 47]

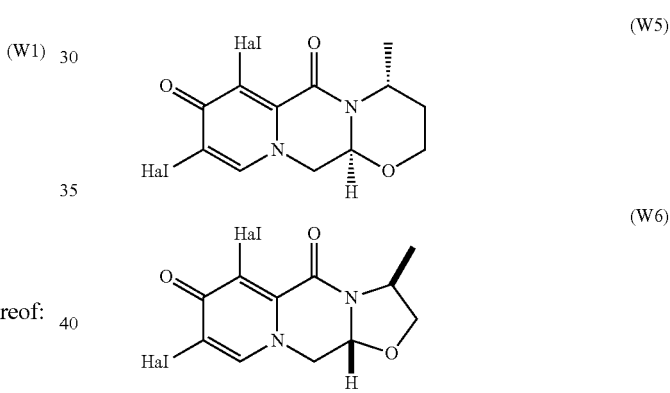

(W5)

(W6)

(wherein Hal is a halogen atom).
(Item 17)
A crystal of a compound shown by formula (U1) or a solvate thereof:

[Chemical formula 48]

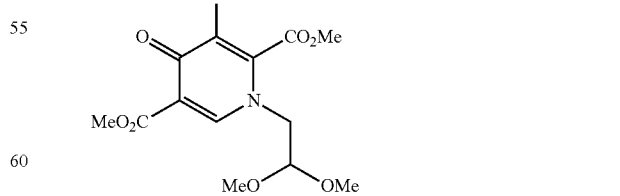

(U1)

(wherein Me is methyl, and Bn is benzyl)
which has peaks in a powder X-ray diffraction spectrum at diffraction angle (2θ): 11.2°±0.2°, 17.2°±0.2°, 17.7°±0.2°, 20.5°±0.2°, 22.0°±0.2° and 26.1°±0.2°.

(Item 18)

A crystal of a compound shown by formula (U2) or a solvate thereof:

[Chemical formula 49]

(U2)

(wherein Me is methyl, and Bn is benzyl)

which has peaks in a powder X-ray diffraction spectrum at diffraction angle (2θ): 7.3°±0.2°, 14.4°±0.2°, 16.1°±0.2°, 18.4°±0.2°, 22.3°±0.2° and 23.1°±0.2°.

(Item 19)

A crystal of a compound shown by formula (U3) or a solvate thereof:

[Chemical formula 50]

(U3)

(wherein Me is methyl, and Bn is benzyl)

which has peaks in a powder X-ray diffraction spectrum at diffraction angle (2θ): 7.2°±0.2°, 16.1°±0.2°, 18.3°±0.2°, 20.6°±0.2°, 22.6°±0.2°, 23.1°±0.2° and 23.7°±0.2°.

(Item 20)

A crystal according to Item 17, which is characterized by a powder X-ray diffraction spectrum substantially consistent with FIG. 1.

(Item 21)

A crystal according to Item 18, which is characterized by a powder X-ray diffraction spectrum substantially consistent with FIG. 2.

(Item 22)

A crystal according to Item 19, which is characterized by a powder X-ray diffraction spectrum substantially consistent with FIG. 3.

The present invention provides the following items as other embodiments.

(Item I)

A method of producing a compound shown by formula (Y1) or formula (Y2) or a salt thereof:

[Chemical formula 51]

(Y1)

(Y2)

(wherein $R^x$ is carbocyclyl optionally substituted by substituent E, heterocyclyl optionally substituted by substituent E, carbocyclyl lower alkyl optionally substituted by substituent E, or heterocyclyl lower alkyl substituted by substituent E, and substituent E is as defined below)

comprising a step of reacting a compound shown by formula (X2):

[Chemical formula 52]

(X2)

(wherein $R^{1d}$ is hydrogen, halogen, lower alkyloxy optionally substituted by substituent E, carbocyclyl lower alkyloxy optionally substituted by substituent E, heterocyclyl lower alkyloxy optionally substituted by substituent E, or —OSi$(R^{1e})_3$, $R^{1e}$s are each independently lower alkyl optionally substituted by substituent E, carbocyclyl optionally substituted by substituent E, heterocyclyl optionally substituted by substituent E, carbocyclyl lower alkyl optionally substituted by substituent E, or heterocyclyl lower alkyl substituted by substituent E, $R^{2d}$ is hydrogen, lower alkyl optionally substituted by substituent E, carbocyclyl optionally substituted by substituent E, or heterocyclyl lower alkyl optionally substituted by substituent E, $R^{3d}$ is hydrogen, lower alkyloxy optionally substituted by substituent E, —N$(R^{3e})_2$, or —OR$^{3e}$, $R^{3e}$s are each independently lower alkyl optionally substituted by substituent E, or two $R^{3e}$s in —N$(R^{3e})_2$ together with the adjacent nitrogen atom may form a heterocycle, and the wavy line means E form and/or Z form or their mixture. Substituent E: halogen, cyano, hydroxy, carboxy, formyl, amino, oxo, nitro, lower alkyl, halogeno lower alkyl, lower alkyloxy, carbocyclyl optionally substituted by substituent F, heterocyclyl optionally substituted by substituent F, carbocyclyl lower alkyloxy optionally substituted by substituent F, heterocyclyl lower alkyloxy optionally substituted by substituent F, carbocyclyl lower alkylthio optionally substituted by substituent F, heterocyclyl lower alkylthio substituted by substituent F, carbocyclyl lower alkylamino optionally substituted by substituent F, heterocyclyl lower alkylamino optionally substituted by substituent F, carbocyclyloxy optionally substituted by substituent F, heterocyclyloxy optionally substituted by substituent F, carbocyclylcarbonyl optionally substituted by substituent F, heterocyclylcarbonyl optionally substituted by substituent F, carbocyclylaminocarbonyl optionally substituted by substituent F, heterocyclylaminocarbonyl optionally substituted by substituent F, halogeno lower alkyloxy, lower alkyloxy lower alkyl, lower alkyloxy lower alkyloxy, lower alkylcarbonyl, lower alkyloxycarbonyl, lower alkyloxycarbonylamino, lower alkylamino, lower alkylcarbonylamino, lower alkylaminocarbonyl, lower alkylsulfonyl, and lower alkylsulfonylamino;

Substituent F: halogen, hydroxyl, carboxy, amino, oxo, nitro, lower alkyl, halogeno lower alkyl, lower alkyloxy, and amino protective group)

with a compound shown by formula (V2):

[Chemical formula 53]

$$R^{4d}O\underset{O}{\overset{O}{\diagdown}}R^{5d}$$ (V2)

(wherein $R^{4d}$ is lower alkyl optionally substituted by substituent E, carbocyclyl lower alkyl optionally substituted by substituent E, or heterocyclyl lower alkyl substituted by substituent E, $R^{5d}$ is hydrogen, halogen, lower alkyloxy substituted by substituent E, or —O—SO$^2$—R$^{5e}$, $R^{5e}$ is lower alkyl optionally substituted by substituent E, carbocyclyl optionally substituted by substituent E, heterocyclyl optionally substituted by substituent E, carbocyclyl lower alkyl optionally substituted by substituent E, or heterocyclyl lower alkyl optionally substituted by substituent E, and substituent E is as defined above)

to obtain a compound shown by formula (X3) or a salt thereof:

[Chemical formula 54]

(X3)

(wherein each symbol is as defined above).

(Item II)

A method of producing a compound shown by formula (Y1) or formula (Y2) or a salt thereof:

[Chemical formula 55]

(Y1)

(Y2)

(wherein $R^x$ is as defined in Item I)

comprising a step of reacting a compound shown by formula (X3) or a salt thereof:

[Chemical formula 56]

(X3)

(wherein each symbol is as defined in Item I)
with a compound shown by formula (V3), or a salt thereof:

[Chemical formula 57]

$$H_2N—R^{6d}$$ (V3)

(wherein $R^{6d}$ is lower alkyl optionally substituted by substituent E, or lower alkenyl optionally substituted by substituent E, and substituent E is as defined in Item I)

to obtain a compound shown by formula (X4), or a salt thereof:

[Chemical formula 58]

(X4)

(wherein each symbol is as defined in Item I or above).

(Item III)

A method of producing a compound shown by formula (Y1) or formula (Y2), or a salt thereof:

[Chemical formula 59]

(Y1)

(Y2)

(wherein R$^x$ is as defined in Item 1)

comprising a step of reacting a compound shown by formula (X4), or a salt thereof:

[Chemical formula 60]

(X4)

(wherein each symbol is as defined in Item I or II)

with (R)-3-amino-butan-1-ol or (S)-2-amino-propan-1-ol to obtain a compound shown by formula (X5) or formula (X5'):

[Chemical formula 61]

(X5)

(X5')

(wherein each symbol is as defined in Item I).

(Item IV)

A method of producing a compound shown by formula (Y1) or formula (Y2), or a salt thereof:

[Chemical formula 62]

(Y1)

(Y2)

(wherein R$^x$ is as defined in Item I)

comprising steps of:

(Step B)

reacting a compound shown by formula (X2):

[Chemical formula 63]

(X2)

(wherein each symbol is as defined in Item I)

with a compound shown by formula (V2):

[Chemical formula 64]

(V2)

(wherein each symbol is as defined in Item I)

to obtain a compound shown by formula (X3) or a salt thereof:

[Chemical formula 65]

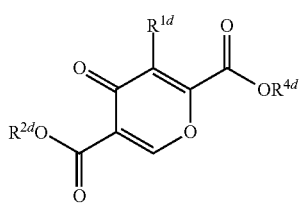
(X3)

(wherein each symbol is as defined in Item I); and (Step C)
reacting a compound shown by formula (X3) or a salt thereof with a compound shown by formula (V3), or a salt thereof:

[Chemical formula 66]

(V3)

(wherein R' is as defined in Item II)
to obtain a compound shown by formula (X4), or a salt thereof:

[Chemical formula 67]

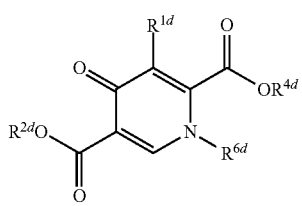
(X4)

(wherein each symbol is as defined in Item I or II).

(Item IV')
A method of producing a compound shown by formula (Y1) or formula (Y2), or a salt thereof:

[Chemical formula 68]

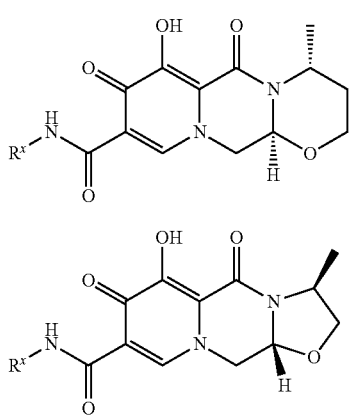
(Y1)
(Y2)

(wherein $R^x$ is as defined in Item I)
comprising steps of:

(Step B)
reacting a compound shown by formula (X2):

[Chemical formula 69]

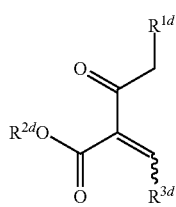
(X2)

(wherein each symbol is as defined in Item I)
with a compound shown by formula (V2):

[Chemical formula 70]

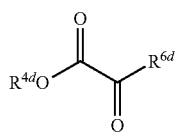
(V2)

(wherein each symbol is as defined in Item I)
to obtain a compound shown by formula (X3), or a salt thereof:

[Chemical formula 71]

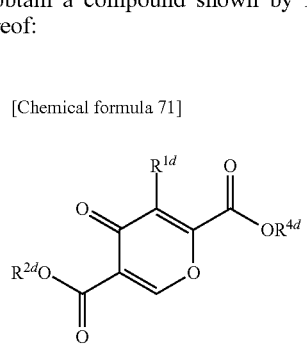
(X3)

(wherein each symbol is as defined in Item I);
(Step C)
reacting a compound shown by formula (X3) with a compound shown by formula (V3), or a salt thereof:
[Chemical formula 72]

(V3)

(wherein Rod is as defined in Item II)
to obtain a compound shown by formula (X4), or a salt thereof:

[Chemical formula 73]

(X4)

(wherein each symbol is as defined in Item I or II); and
(Step D)
reacting a compound shown by formula (X4), or a salt thereof with (R)-3-amino-butan-1-ol or (S)-2-amino-propan-1-ol to obtain a compound shown by formula (X5) or formula (X5'), or a salt thereof:

[Chemical formula 74]

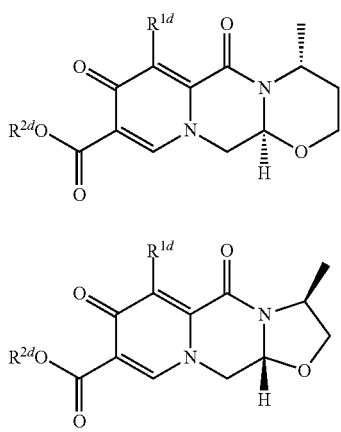

(X5)

(X5')

(wherein each symbol is as defined in Item I).
(Item IV")
A method of producing a compound shown by formula (Y1) or formula (Y2), or a salt thereof:

[Chemical formula 75]

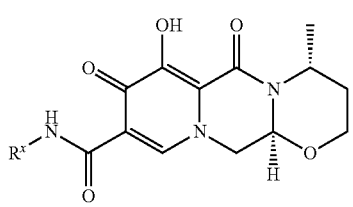

(Y1)

(Y2)

(wherein $R^x$ is as defined in Item I)
comprising steps of:

(Step B)
reacting a compound shown by formula (X2):

[Chemical formula 76]

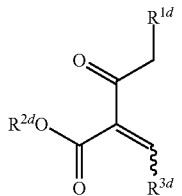

(X2)

(wherein each symbol is as defined in Item I)
with a compound shown by formula (V2):

[Chemical formula 77]

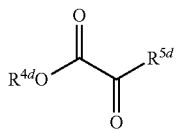

(V2)

(wherein each symbol is as defined in Item I)
to obtain a compound shown by formula (X3), or a salt thereof:

[Chemical formula 78]

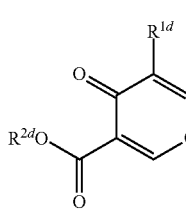

(X3)

(wherein each symbol is as defined in Item I); and
(Step C)
reacting a compound shown by formula (X3) with a compound shown by formula (V3), or a salt thereof:
[Chemical formula 79]

$H_2N—R^{6d}$ (V3)

(wherein $R^{6d}$ is as defined in Item II)
to obtain a compound shown by formula (X4), or a salt thereof:

[Chemical formula 80]

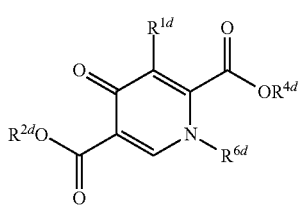

(X4)

(wherein each symbol is as defined in Item I or II);

(Step D)

reacting a compound shown by formula (X4), or a salt thereof with (R)-3-amino-butan-1-ol or (S)-2-amino-propan-1-ol to obtain a compound shown by formula (X5) or formula (X5'), or a salt thereof:

[Chemical formula 81]

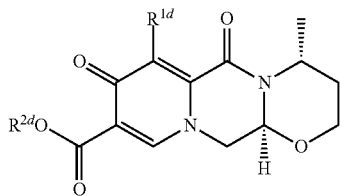
(X5)

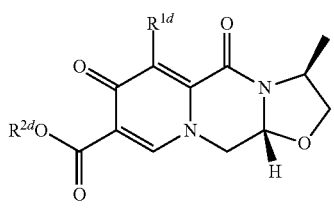
(X5')

(wherein each symbol is as defined in Item I); and (Step E)

reacting with a compound shown by formula (V6), or a salt thereof:

[Chemical formula 82]

$R^x$—$NH_2$ (V6)

(wherein $R^x$ is as defined in Item I).

(Item V)

A method according to Item IV, IV', or IV'', wherein Step B and Step C are continuously performed.

(Item VI)

A method of producing a compound shown by formula (Y1) or formula (Y2), or a salt thereof:

[Chemical formula 83]

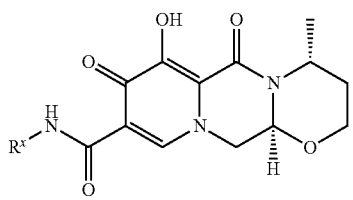
(Y1)

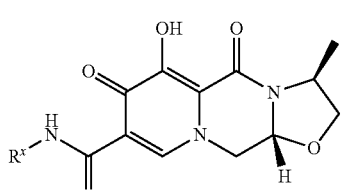
(Y2)

(wherein $R^x$ is as defined in Item I)

comprising a step of reacting a compound shown by formula (X2):

[Chemical formula 84]

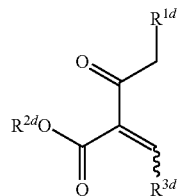
(X2)

(wherein each symbol is as defined in Item I) with a compound shown by formula (V2):

[Chemical formula 85]

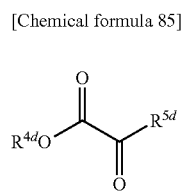
(V2)

(wherein each symbol is as defined in Item I) and a compound shown by formula (V2')

[Chemical formula 86]

$NH_4^+X^{d-}$ (V2')

(wherein $X^{d-}$ is a counter anion of ammonium cation) to obtain a compound shown by formula (X4'), or a salt thereof:

[Chemical formula 87]

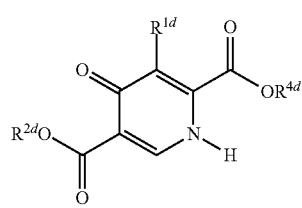
(X4')

(wherein each symbol is as defined in Item I).

(Item VII)

A method of producing a compound shown by formula (Y1) or formula (Y2), or a salt thereof:

[Chemical formula 88]

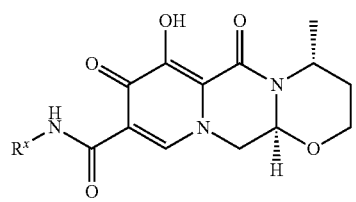
(Y1)

-continued

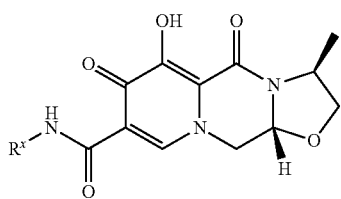
(Y2)

(wherein $R^x$ is as defined in Item I)
comprising steps of:
(Step B')
reacting a compound shown by formula (X2):

[Chemical formula 89]

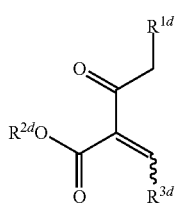
(X2)

(wherein each symbol is as defined in Item I)
with a compound shown by formula (V2):

[Chemical formula 90]

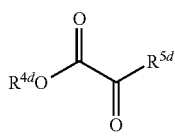
(V2)

(wherein each symbol is as defined in Item I)
and a compound shown by formula (V2'):
[Chemical formula 91]

$NH_4^+X^{d-}$ (V2')

(wherein $X^{d-}$ is a counter anion of ammonium cation)
to obtain a compound shown by formula (X4'), or a salt thereof:

[Chemical formula 92]

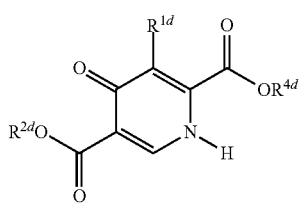
(X4')

(wherein each symbol is as defined in Item I); and
(Step C')
reacting a compound shown by formula (X4') with a compound shown by formula (V3'):

[Chemical formula 93]

$R^{6d}\text{-}L^d$ (V3')

(wherein $R^{6d}$ is as defined in Item II, and $L^d$ is a leaving group)
to obtain a compound shown by formula (X4), or a salt thereof:

[Chemical formula 94]

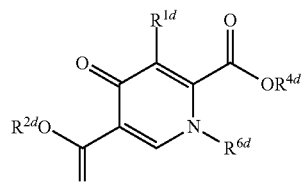
(X4)

(wherein each symbol is as defined in Item I or II).
(Item VII')
A method of producing a compound shown by formula (Y1) or formula (Y2), or a salt thereof:

[Chemical formula 95]

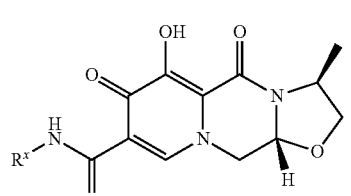
(Y1)

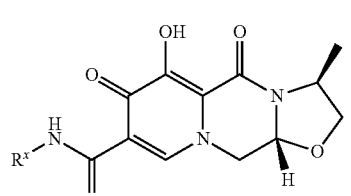
(Y2)

(wherein $R^x$ is as defined in Item I)
comprising steps of:
(Step B')
reacting a compound shown by formula (X2):

[Chemical formula 96]

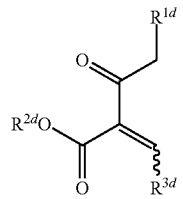
(X2)

(wherein each symbol is as defined in Item I)
with a compound shown by formula (V2):

[Chemical formula 97]

$$\text{R}^{4d}\text{O}-\overset{\overset{\displaystyle O}{\|}}{\underset{\underset{\displaystyle O}{\|}}{C}}-\text{R}^{5d}$$ (V2)

(wherein each symbol is as defined in Item I)
and a compound shown by formula (V2'):
[Chemical formula 98]

NH₄⁺Xᵈ⁻ (V2')

(wherein $X^{d-}$ is a counter anion of ammonium cation)
to obtain a compound shown by formula (X4'), or a salt thereof:

[Chemical formula 99]

(X4')

(wherein each symbol is as defined in Item I);
(Item C')
reacting a compound shown by formula (X4') with a compound shown by formula (V3'):
[Chemical formula 100]

$R^{6d}-L^d$ (V3')

(wherein $R^{6d}$ is as defined in Item II, and $L^d$ is a leaving group)
to obtain a compound shown by formula (X4), or a salt thereof:

[Chemical formula 101]

(X4)

(wherein each symbol is as defined in Item I or II); and
(Step D)
reacting a compound shown by formula (X4) with (R)-3-amino-butan-1-ol or (S)-2-amino-propan-1-ol to obtain a compound shown by formula (X5) or formula (X5'), or a salt thereof:

[Chemical formula 102]

(X5)

(X5')

(wherein each symbol is as defined in Item I).
(Item VII")
A method of producing a compound shown by formula (Y1) or formula (Y2), or a salt thereof:

[Chemical formula 103]

(Y1)

(Y2)

(wherein $R^x$ is as defined in Item I)
comprising steps of:
(Step B')
reacting a compound shown by formula (X2):

[Chemical formula 104]

(X2)

(wherein each symbol is as defined in Item I)
with a compound shown by formula (V2):

[Chemical formula 105]

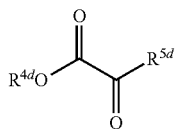
(V2)

(wherein each symbol is as defined in Item I)
and a compound shown by formula (V2'):
[Chemical formula 106]

$$NH_4^+ X^{d-} \quad (V2')$$

(wherein $X^{d-}$ is a counter anion of ammonium cation)
to obtain a compound shown by formula (X4'), or a salt thereof:

[Chemical formula 107]

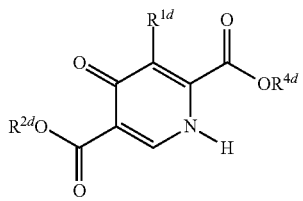
(X4')

(wherein each symbol is as defined in Item I);
(Step C')
reacting a compound shown by formula (X4') or a salt thereof with a compound shown by formula (V3'):
[Chemical formula 108]

$$R^{6d}\text{-}L^d \quad (V3')$$

(wherein $R^{6d}$ is as defined in Item II and $L^d$ is a leaving group)
to obtain a compound shown by formula (X4), or a salt thereof:

[Chemical formula 109]

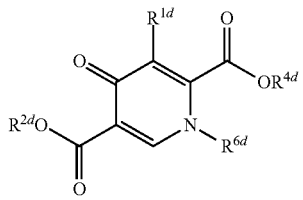
(X4)

(wherein each symbol is as defined in Item I or II);
(Step D)
reacting a compound shown by formula (X4) with (R)-3-amino-butan-1-ol or (S)-2-amino-propan-1-ol to obtain a compound shown by formula (X5) or formula (X5'), or a salt thereof:

[Chemical formula 110]

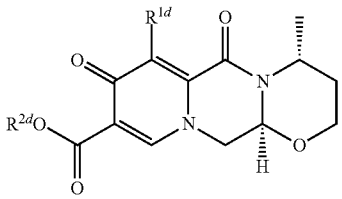
(X5)

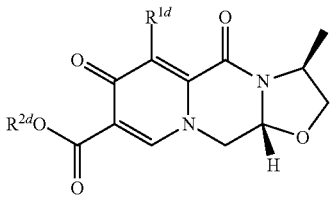
(X5')

(wherein each symbol is as defined in Item I); and
(Step E)
reacting with a compound shown by formula (V6), or a salt thereof:
[Chemical formula 111]

$$R^X\text{—}NH_2 \quad (V6)$$

(wherein $R^x$ is as defined in Item I).
(Item VIII)
A method according to any one of Items I, IV, IV', IV''', VI, VII, VII', or VII'', wherein A compound shown by formula (X2) is obtained by reacting a compound shown by formula (X1):

[Chemical formula 112]

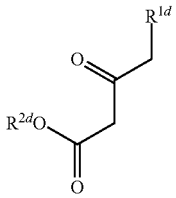
(X1)

(wherein each symbol is as defined in Item I)
with a compound shown by formula (V1):

[Chemical formula 113]

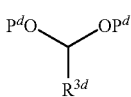
(V1)

(wherein $P^d$ is lower alkyl optionally substituted by substituent E, and $R^{3d}$ and substituent E are as defined in Item I).
(Item IX)
A method according to any one of Items I, IV, IV', IV''', VI, VII, VII', or VII'', wherein a compound shown by formula (X2) is obtained by reacting a compound by formula (Z1):

[Chemical formula 114]

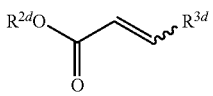

(Z1)

(wherein each symbol is as defined in Item I) with a compound shown by formula (Z2):

[Chemical formula 115]

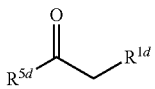

(Z2)

(wherein each symbol is as defined in Item I).
(Item X)
A method according to any one of Items I to VII, IV', IV'', VII', and VII'', wherein $R^x$ is carbocyclyl lower alkyl optionally substituted by substituent E.
(Item XI)
A method according to any one of Item I to VII, IV', IV'', VII', and VII'', wherein $R^x$ is 2,4-difluorobenzyl.

Effect of the Invention

The present invention enables production of compound (Y1) and compound (Y2) useful as anti-HIV drugs having HIV integrase inhibitory activity in a short step as compared to conventional methods, so the compounds can be efficiently produced in a high yield. In addition, the present invention has a number of advantages, that use of a reaction reagent with toxicity can be avoided, use of harmful reaction can be avoided, use of an expensive reaction reagent can be avoided, use of an environmentally harmful reagent and solvent can be avoided, and the like. Therefore, the present invention is useful for the industrial production of anti-HIV drugs.

In addition, the crystals of compound (U1), compound (U2), and compound (U3) according to the present invention have advantages such as high stability to heat, high stability to light, high purification effect to remove impurities, easy handling, and/or small hygroscopy, and therefore, can be efficiently produced by utilizing those advantages.

BEST MODE FOR CARRYING OUT THE INVENTION

Figure 1:
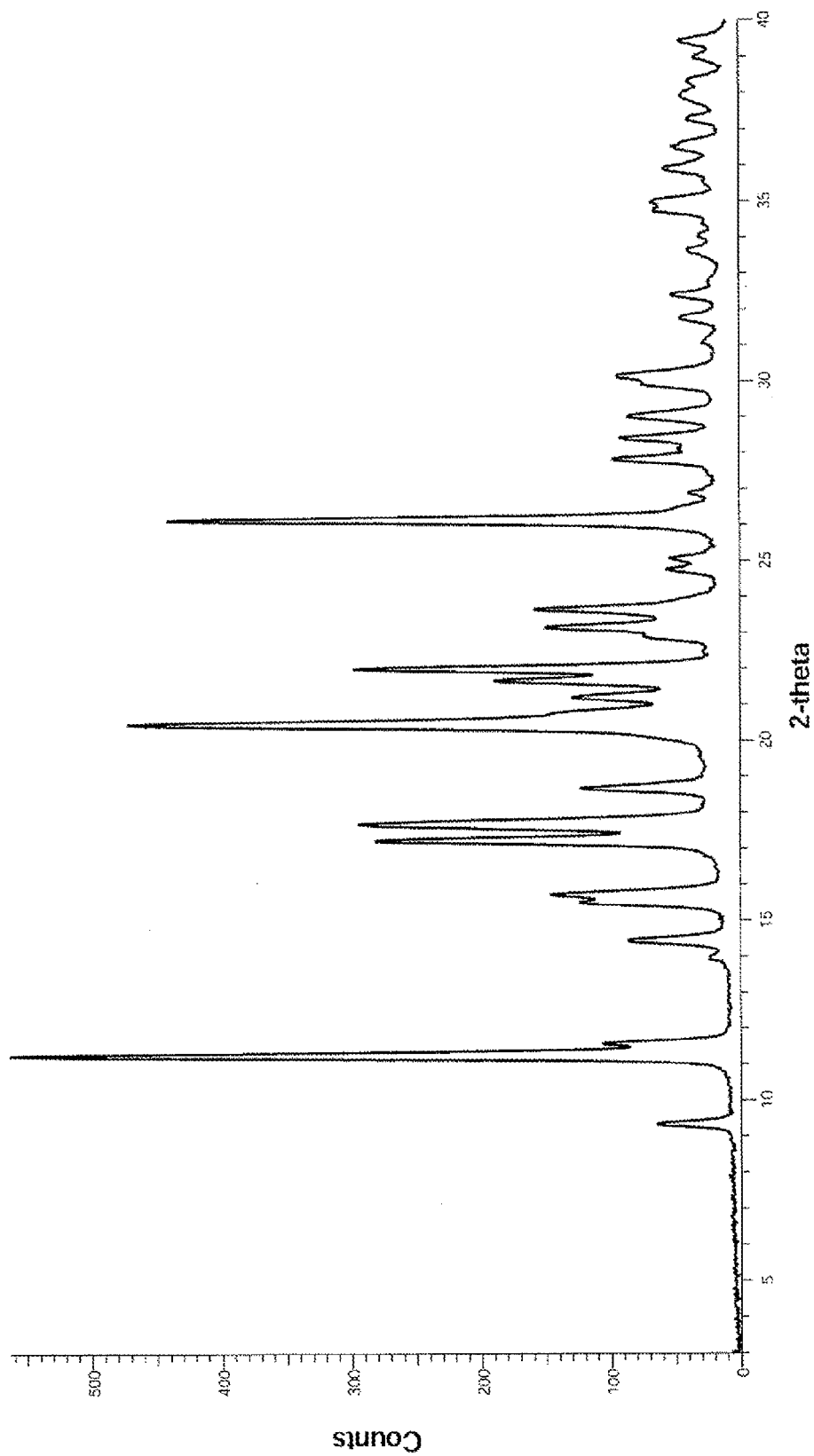
FIG. 1 is a powder X-ray diffraction pattern of compound 12B obtained in Step 1 of Example 12. The ordinate represents peak intensity, and the abscissa represents a diffraction angle (2θ).
Figure 2:
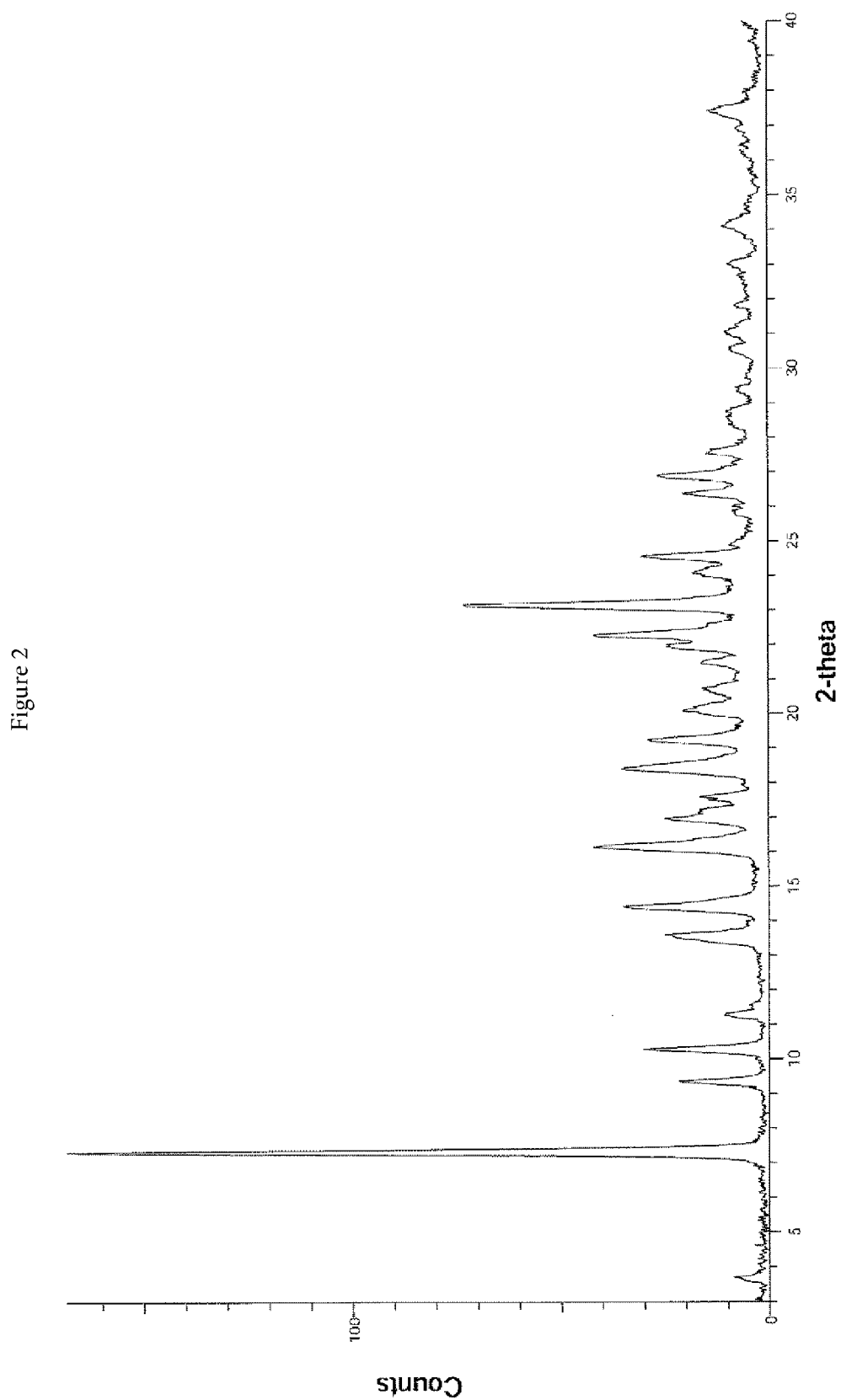
FIG. 2 is a powder X-ray diffraction pattern of compound 15A obtained in Example 15A. The ordinate represents peak intensity, and the abscissa represents a diffraction angle (2θ).
Figure 3:
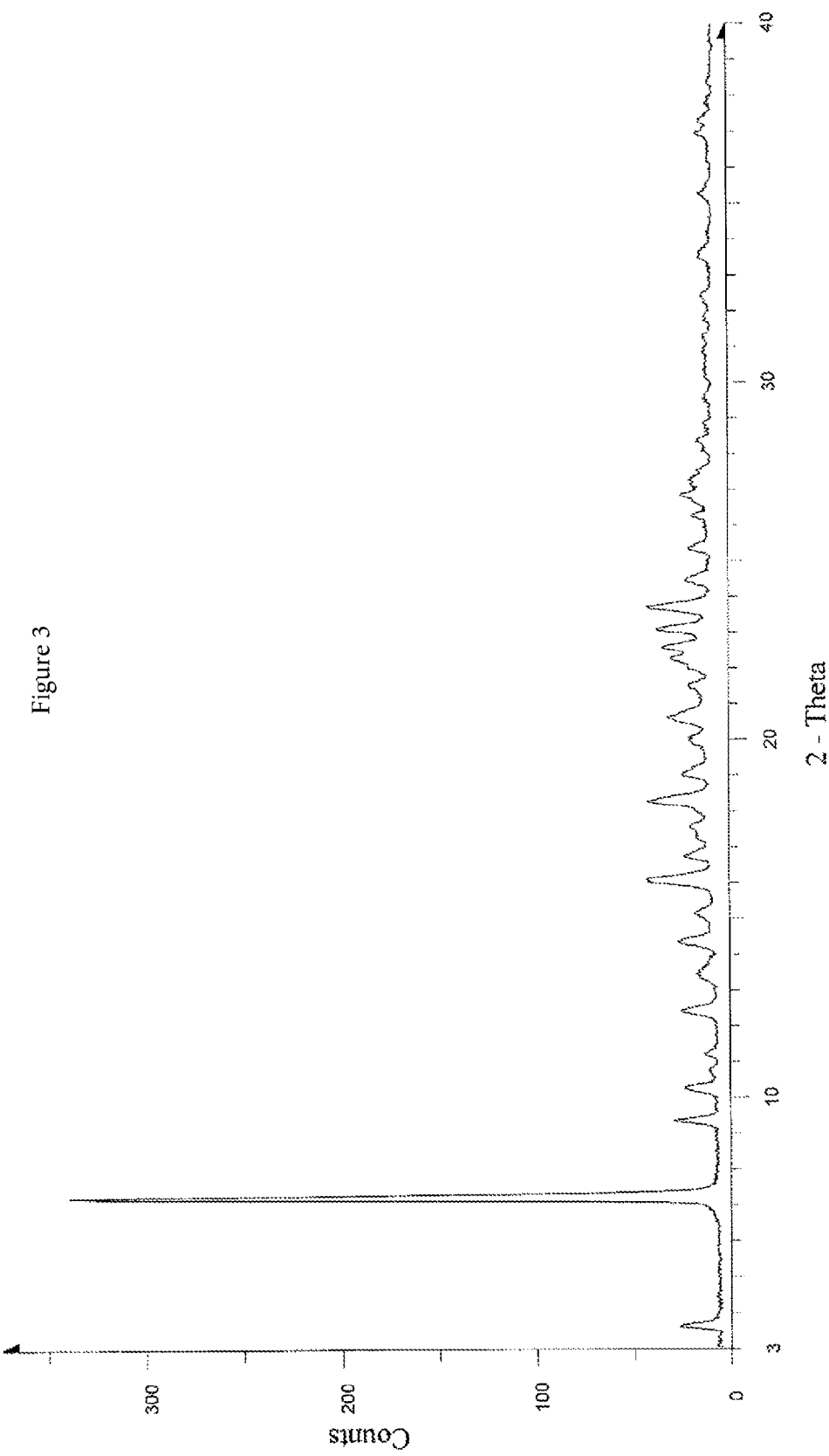
FIG. 3 is a powder X-ray diffraction pattern of compound 15B obtained in Example 15B. The ordinate represents peak intensity, and the abscissa represents a diffraction angle (2θ).

Hereinafter, the terms described in the present specification will be described. Each term alone or in combination with other terms has the same meaning.

The term "halogen" encompasses fluorine, chlorine, bromine, and iodine atoms.

The term "lower alkyl" encompasses linear or branched alkyl having 1 to 15 carbon atoms, preferably 1 to 10 carbon atoms, more preferably 1 to 6 carbon atoms, further preferably 1 to 4 carbon atoms, most preferably 1 or 2 carbon atoms. Examples thereof include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, and n-decyl. Examples of preferred embodiments of "lower alkyl" include methyl, ethyl, n-propyl, isopropyl, n-butyl, isobutyl, sec-butyl, tert-butyl, and n-pentyl. Examples of more preferred embodiments thereof include methyl, ethyl, n-propyl, isopropyl, and tert-butyl.

The term "lower alkenyl" encompasses linear or branched alkenyl having 2 to 15 carbon atoms, preferably 2 to 10 carbon atoms, more preferably 2 to 6 carbon atoms, further preferably 2 to 4 carbon atoms and having one or more double bonds at an arbitrary position. Specifically, the "lower alkenyl" encompasses vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl, and the like. Examples of preferred embodiments of "lower alkenyl" include vinyl, allyl, propenyl, isopropenyl, and butenyl. Examples of particularly preferred embodiments thereof include allyl.

The lower alkyl moieties of "lower alkyloxy", "lower alkylcarbonyl", "lower alkyloxycarbonyl", "carbocyclyl lower alkyl", "heterocyclyl lower alkyl", "halogeno lower alkyl", "carbocyclyl lower alkyloxy", "heterocyclyl lower alkyloxy", "halogeno lower alkyloxy", "lower alkyloxy lower alkyl", "lower alkyloxy lower alkyloxy", "lower alkylamino", "lower alkylcarbonylamino", "lower alkylaminocarbonyl", "lower alkylsulfonyl", "lower alkylsulfonylamino", "carbocyclyl lower alkylthio", "heterocyclyl lower alkylthio", "carbocyclyl lower alkylamino", and "heterocyclyl lower alkylamino" are also the same as the "lower alkyl" described above.

The halogen moieties of "halogeno lower alkyl" and "halogeno lower alkyloxy" are also the same as the "halogen" described above. In this context, the "lower alkyl" and the "lower alkyloxy" may be substituted by one halogen atom or more identical or different halogen atoms at their respective arbitrary positions on the alkyl groups.

The term "carbocyclyl" means carbocyclyl having 3 to 20 carbon atoms, preferably 3 to 16 carbon atoms, more preferably 4 to 12 carbon atoms and encompasses cycloalkyl, cycloalkenyl, aryl, non-aromatic condensed carbocyclyl, and the like.

The "cycloalkyl" means carbocyclyl having 3 to 16 carbon atoms, preferably 3 to 12 carbon atoms, more preferably 4 to 8 carbon atoms and encompasses, for example, cyclopropyl, cyclobutyl, cyclopentyl, cyclohexyl, cycloheptyl, cyclooctyl, cyclononyl, and cyclodecyl.

The "cycloalkenyl" encompasses a group having one or more double bonds at an arbitrary position in the ring of the cycloalkyl. Examples thereof include cyclopropenyl, cyclobutenyl, cyclopentenyl, cyclohexenyl, cycloheptenyl, cyclooctyl, and cyclohexadienyl.

The "aryl" encompasses phenyl, naphthyl, anthryl, phenanthryl, and the like. Particularly, phenyl is preferred.

The "non-aromatic condensed carbocyclyl" encompasses a group in which two or more cyclic groups selected from the "cycloalkyl", "cycloalkenyl", and "aryl" described above are condensed. Examples thereof include indanyl, indenyl, tetrahydronaphthyl, fluorenyl, and adamantyl.

Examples of preferred embodiments of "carbocyclyl" include cycloalkyl, aryl, and non-aromatic condensed carbocyclyl. Specific examples thereof include cyclopropyl, cyclobutyl, cyclopentyl, cyclohexyl, cycloheptyl, and phenyl.

The carbocyclyl moieties of "carbocyclyl lower alkyl", "carbocyclyl lower alkyloxy", "carbocyclyl lower alkylthio", "carbocyclyl lower alkylamino", "carbocyclyloxy", "carbocyclylcarbonyl", and "carbocyclylaminocarbonyl" are also the same as the "carbocyclyl" described above. In this context, the "carbocyclyl lower alkyl" in particularly preferred embodiments is benzyl.

Examples of preferred embodiments of "carbocyclyl lower alkyloxy" include benzyloxy.

Examples of preferred embodiments of "carbocyclyl lower alkylthio" include benzylthio.

Examples of preferred embodiments of "carbocyclyl lower alkylamino" include benzylamino.

Examples of preferred embodiments of "carbocyclyloxy" include phenyloxy.

Examples of preferred embodiments of "carbocyclylcarbonyl" include phenylcarbonyl.

Examples of preferred embodiments of "carbocyclylaminocarbonyl" include phenylaminocarbonyl.

The term "heterocyclyl" encompasses heterocyclyl having, in the ring, one or more identical or different heteroatoms arbitrarily selected from O, S, and N, such as heteroaryl, none-aromatic heterocyclyl, bicyclic condensed heterocyclyl, and tricyclic condensed heterocyclyl.

Examples of the "heteroaryl" include 5- to 6-membered aromatic cyclyl such as pyrrolyl, imidazolyl, pyrazolyl, pyridyl, pyridazinyl, pyrimidinyl, pyrazinyl, triazolyl, triazinyl, tetrazolyl, furyl, thienyl, isoxazolyl, oxazolyl, oxadiazolyl, isothiazolyl, thiazolyl, and thiadiazolyl.

Examples of the "none-aromatic heterocyclyl" include dioxanyl, thiiranyl, oxiranyl, oxetanyl, oxathiolanyl, azetidinyl, thianyl, thiazolidinyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydropyridyl, tetrahydrofuryl, tetrahydropyranyl, dihydrothiazolyl, tetrahydrothiazolyl, tetrahydroisothiazolyl, dihydrooxazinyl, hexahydroazepinyl, tetrahydrodiazepinyl, hexahydropyridazinyl, hexahydropyrimidinyl, and dioxolanyl.

Examples of the "bicyclic condensed heterocyclyl" include indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, thienopyridyl, thienopyrrolyl, thienopyrazolyl, thienopyrazinyl, furopyrrolyl, thienothienyl, imidazopyridyl, pyrazolopyridyl, thiazolopyridyl, pyrazolopyrimidinyl, pyrazolotriazinyl, pyridazolopyridyl, triazolopyridyl, imidazothiazolyl, pyrazinopyridazinyl, quinazolinyl, quinolyl, isoquinolyl, naphthyridinyl, dihydrothiazolopyrimidinyl, tetrahydroquinolyl, tetrahydroisoquinolyl, dihydrobenzofuryl, dihydrobenzoxazinyl, dihydrobenzimidazolyl, tetrahydrobenzothienyl, tetrahydrobenzofuryl, benzodioxolyl, benzodioxonyl, chromanyl, chromenyl, octahydrochromenyl, dihydrobenzodioxynyl, dihydrobenzooxedinyl, dihydrobenzodioxepinyl, and dihydrothienodioxynyl.

Examples of the "tricyclic condensed heterocyclyl" include carbazolyl, acridinyl, xanthenyl, phenothiazinyl, phenoxathiinyl, phenoxazinyl, dibenzofuryl, imidazoquinolyl, and tetrahydrocarbazolyl.

Examples of preferred embodiments of "heterocyclyl" include 5- to 6-membered heteroaryl or none-aromatic heterocyclyl, and tricyclic condensed heterocyclyl.

The heterocyclyl moieties of "heterocyclyl lower alkyl", "heterocyclyl lower alkyloxy", "heterocyclyl lower alkylthio", "heterocyclyl lower alkylamino", "heterocyclyloxy", "heterocyclylcarbonyl", and "heterocyclylaminocarbonyl" are also the same as the "heterocyclyl" described above. In this context, the "heterocyclyl lower alkyl" in particularly preferred embodiments is pyridylmethyl.

Examples of preferred embodiments of "heterocyclyl lower alkyloxy" include pyridylmethyloxy.

Examples of preferred embodiments of "heterocyclyl lower alkylthio" include pyridylmethylthio.

Examples of preferred embodiments of "heterocyclyl lower alkylamino" include pyridylmethylamino.

Examples of preferred embodiments of "heterocyclyloxy" include pyridyloxy.

Examples of preferred embodiments of "heterocyclylcarbonyl" include pyridylcarbonyl.

Examples of preferred embodiments of "heterocyclylaminocarbonyl" include pyridylaminocarbonyl.

The phrase "Step B and Step C are continuously performed" means that after the completion of Step B, Step C is carried out without performing the isolation operation (e.g., crystallization and collection by filtration, and distillation), extraction operation, and column chromatography purification of the product of Step B. Step B and Step C may be performed in the same or different reactors.

The term "lower alkyl optionally substituted by substituent E" means that "lower alkyl" is unsubstituted or is bonded to one or more chemically acceptable substituents selected from substituent E. When the lower alkyl is bonded to a plurality of substituents, these substituents may be the same as or different from each other. Examples thereof include methyl, fluoromethyl, trifluoromethyl, chlorodifluoromethyl, and

[Chemical Formula 116]

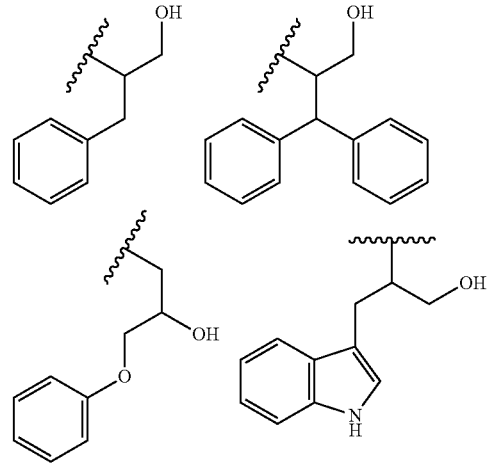

The term "carbocyclyl optionally substituted by substituent E" means that "carbocyclyl" is unsubstituted or is bonded to one or more chemically acceptable substituents selected from substituent E. When the carbocyclyl is bonded to a plurality of substituents, these substituents may be the same as or different from each other. The "carbocyclyl optionally substituted by substituent E" encompasses, for example, fluorophenyl, difluorophenyl, and methoxyfluorophenyl.

The term "carbocyclyl lower alkyl optionally substituted by substituent E" means that "carbocyclyl" and/or "lower alkyl" is unsubstituted or is bonded to one or more chemically acceptable substituents selected from substituent E. When the carbocyclyl and/or the lower alkyl is bonded to a plurality of substituents, these substituents may be the same as or different from each other. The "carbocyclyl lower alkyl optionally substituted by substituent E" encompasses, for example, 4-fluorobenzyl, 2,4-difluorobenzyl, 4-methoxy-2-fluorobenzyl, and 4-methoxyphenyldifluoromethyl.

The terms "lower alkyloxy optionally substituted by substituent E", "carbocyclyl lower alkyloxy optionally substituted by substituent E", "heterocyclyl lower alkyloxy optionally substituted by substituent E", and "lower alkenyl optionally substituted by substituent E" are also defined similarly.

The term "carbocyclyl optionally substituted by substituent F" means that "carbocyclyl" is unsubstituted or is bonded to one or more chemically acceptable substituents selected from substituent F. When the carbocyclyl is bonded to a plurality of substituents, these substituents may be the same as or different from each other. The "carbocyclyl optionally substituted by substituent F" encompasses, for example, fluorophenyl, difluorophenyl, and methoxyfluorophenyl.

The term "carbocyclyl lower alkyloxy optionally substituted by substituent F" means that the "carbocyclyl" moiety is unsubstituted or is bonded to one or more chemically acceptable substituents selected from substituent F. When the carbocyclyl moiety is bonded to a plurality of substituents, these substituents may be the same as or different from each other. The "carbocyclyl lower alkyloxy optionally substituted by substituent F" encompasses, for example, fluorobenzyloxy, difluorobenzyloxy, and methoxyfluorobenzyloxy.

The terms "heterocyclyl optionally substituted by substituent F", "heterocyclyl lower alkyloxy optionally substituted by substituent F", "carbocyclyl lower alkylthio optionally substituted by substituent F", "heterocyclyl lower alkylthio optionally substituted by substituent F", "carbocyclyl lower alkylamino optionally substituted by substituent F", "heterocyclyl lower alkylamino optionally substituted by substituent F", "carbocyclyloxy optionally substituted by substituent F", "heterocyclyloxy optionally substituted by substituent F", "carbocyclylcarbonyl optionally substituted by substituent F", "heterocyclylcarbonyl optionally substituted by substituent F", "carbocyclylaminocarbonyl optionally substituted by substituent F", and "heterocyclylaminocarbonyl optionally substituted by substituent F" are also defined similarly.

The phrase "two $R^{3e}$s in $-N(R^{3e})_2$ together with the adjacent nitrogen atom may form a heterocycle" encompasses, for example, formulas shown below:

[Chemical Formula 117]

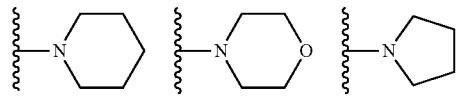

The "amino protective group" can be any general protective group for the amino group and exemplified by amino protective groups described in, for example, Protective Groups in Organic Synthesis, Theodora W Greene (John Wiley & Sons). The "amino protective group" is preferably a tert-butyloxycarbonyl or benzyloxycarbonyl group.

The "carboxyl protective group" can be any general protective group for the carboxyl group and exemplified by carboxyl protective groups described in, for example, Protective Groups in Organic Synthesis, Theodora W Greene (John Wiley & Sons). Preferred examples thereof include methyl, ethyl, tert-butyl, methoxymethyl, allyl, benzyl, and p-methoxybenzyl groups.

Examples of the "counter anion of ammonium cation" represented by $X^d$ include halogen$^-$, $CH_3COO^-$, $HCOO^-$, $NO_3^-$, $BF_4^-$, $PF_6^-$, $HO^-$, $Ph\text{-}SO_3^-$, $CH_3\text{-}Ph\text{-}SO_3^-$, $CH_3\text{---}SO_3^-$, $PO_4^{3-}$, $SO_4^{2-}$ and $HSO_4^-$. The "counter anion of ammonium cation" is preferably halogen$^-$, $CH_3COO^-$, $NO_3^-$, or $SO_4^{2-}$. In the case of divalent or trivalent anion, the counter anion represents that each $NH_4^+$ cation is in an uncharged state by the binding of two or three molecules thereof. Specific examples of $NH_4^+X^{d-}$ include $NH_4^+Cl^-$, $NH_4^+CH_3COO^-$, $(NH_4^+)_2SO_4^{2-}$, and $(NH_4^+)_3PO_4^{3-}$.

The "leaving group" refers to a substituent that is eliminated through nucleophilic reaction. Examples thereof include halogen, $-O-SO_2-CH_3$, $-O-SO_2-CF_3$, $-O-SO_2\text{-}Ph$, and $-O-SO_2\text{-}Ph\text{-}CH_3$. The "leaving group" is preferably halogen.

(In this context, Ph represents a phenyl group.)

Examples of the salt include basic salts or acidic salts.

Examples of the basic salts include: alkali metal salts such as sodium salt, potassium salt, and lithium salt; alkaline earth metal salts such as calcium salt and magnesium salt; ammonium salt; aliphatic amine salts such as trimethylamine salt, triethylamine salt, dicyclohexylamine salt, ethanolamine salt, diethanolamine salt, triethanolamine salt, procaine salt, meglumine salt, diethanolamine salt, and ethylenediamine salt; aralkylamine salts such as N,N-dibenzylethylenediamine and benethamine salt;

heterocyclic aromatic amine salts such as pyridine salt, picoline salt, quinoline salt, and isoquinoline salt;

quaternary ammonium salts such as tetramethylammonium salt, tetraethylammonium salt, benzyltrimethylammonium salt, benzyltriethylammonium salt, benzyltributylammonium salt, methyltrioctylammonium salt, and tetrabutylammonium salt; and basic amino acid salts such as arginine salt and lysine salt.

Examples of the acidic salts include: inorganic acid salts such as hydrochloride, sulfate, nitrate, phosphate, carbonate, bicarbonate, and perchlorate; organic acid salts such as acetate, propionate, lactate, maleate, fumarate, tartrate, malate, citrate, and ascorbate; sulfonates such as methanesulfonate, isethionate, benzenesulfonate, and p-toluenesulfonate; and acidic amino acids such as aspartate and glutamate.

The salt derived from the carboxyl or hydroxyl group is preferably a basic salt, more preferably an alkali metal salt. Particularly preferred examples of the salt include sodium salt, lithium salt, and potassium salt. The most preferred example of the salt includes sodium salt.

The salt derived from the amine site is preferably an acidic salt, more preferably an inorganic acid salt. Examples of preferable salts include hydrochloride and sulfate.

Hereinafter, the production method of the present invention will be described.

(Step A)

This step is the step of reacting compound (X1) with compound (V1) to obtain a solution containing compound (X2), as shown below in the reaction formula.

In this context, the "solution" means compound (X2) in a dissolved state and also encompasses compound (X2) in a suspension or slurry form in which the compound is dispersed without being completely dissolved. This holds true for the description below, and the "solution" according to the present specification encompasses suspension and slurry forms.

[Chemical Formula 118]

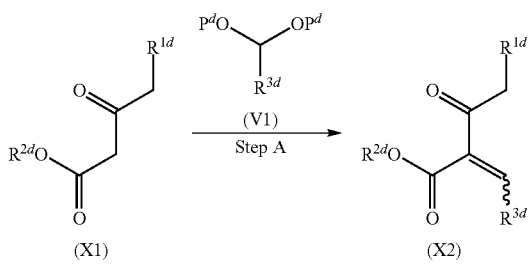

(wherein each symbol is as defined above).

The compound (X1) may be a commercially available reagent or can be obtained by a method known in the art.

When $R^{1d}$ is halogen, nucleophilic substitution reaction may be performed, if desired in the presence of a base, in a solvent supplemented with an alcohol reagent such as a lower alcohol optionally substituted by substituent E, a carbocyclyl lower alkyl alcohol optionally substituted by substituent E, a heterocyclyl lower alkyl alcohol optionally substituted by substituent E, or $(R^{1e})_3Si$—OH to obtain compound (X1) wherein $R^{1d}$ is lower alkyloxy optionally substituted by substituent E, carbocyclyl lower alkyloxy optionally substituted by substituent E, heterocyclyl lower alkyloxy optionally substituted by substituent E, or —OSi$(R^{1e})_3$.

Examples of the "lower alkyloxy optionally substituted by substituent E" represented by $R^{1d}$ include methoxy, ethoxy, isopropoxy, trichloromethoxy, and trifluoromethoxy. Methoxy is preferred.

Examples of the "carbocyclyl lower alkyloxy optionally substituted by substituent E" represented by $R^{1d}$ include benzyloxy, phenethyloxy, 2,4-difluorobenzyloxy, and 4-methoxybenzyloxy. Benzyloxy is preferred.

Examples of the "heterocyclyl lower alkyloxy optionally substituted by substituent E" represented by $R^{1d}$ include pyridylmethyloxy.

$R^{1d}$ in preferred embodiments is hydrogen, chloro, bromo, methoxy, or benzyloxy.

When $R^{1d}$ is —OSi$(R^{1e})_3$, $R^{1e}$ in preferred embodiments is methyl, ethyl, n-propyl, isopropyl, tert-butyl, or the like.

Examples of the "lower alkyl optionally substituted by substituent E" represented by $R^{2d}$ include methyl, ethyl, n-propyl, isopropyl, and tert-butyl.

Examples of the "carbocyclyl lower alkyl optionally substituted by substituent E" represented by $R^{2d}$ include benzyl and 4-methoxybenzyl.

Examples of the "heterocyclyl lower alkyl optionally substituted by substituent E" represented by $R^{2d}$ include pyridylmethyl.

$R^{2d}$ in preferred embodiments is methyl, ethyl, n-propyl, isopropyl, tert-butyl, benzyl, 4-methoxybenzyl, or the like.

The reaction solvent used in the nucleophilic substitution reaction for obtaining the compound (X1) is preferably an aprotic solvent. Examples thereof include acetonitrile, tetrahydrofuran, dioxane, diethyl ether, dichloromethane, chloroform, toluene, xylene, ethyl acetate, N,N-dimethylformamide, N,N-dimethylacetamide, dimethylimidazolidinone, and mixed solvents thereof.

The base can be any base capable of deprotonating the alcohol reagent. Examples thereof include n-butyllithium, tert-butyllithium, sodium tert-butoxide, potassium-tert-butoxide, sodium tert-pentoxide, sodium methoxide, sodium ethoxide, sodium hydride, lithium diisopropylamide, and lithium bis(trimethylsilyl)amide.

The amount of the base is approximately 1.0 to 3.0 molar equivalents with respect to compound (X1) wherein $R^{1d}$ is halogen.

The amount of the alcohol reagent is approximately 0.5 to 1.5 molar equivalents with respect to compound (X1) wherein $R^{1d}$ is halogen.

The reaction temperature is usually 0° C. to reflux temperature, preferably room temperature to 50° C.

The reaction time is usually 10 minutes to 50 hours, preferably 1 to 4 hours.

The compound (V1) can be obtained as a commercially available reagent or by a method known in the art.

Examples of the "lower alkyl optionally substituted by substituent E" represented by $P^d$ include methyl, ethyl, and trifluoromethyl. $P^d$ in preferred embodiments is methyl.

Examples of the "lower alkyloxy optionally substituted by substituent E" represented by $R^{3d}$ include methoxy and ethoxy.

When $R^{3d}$ is —N$(R^{3e})_2$, examples of the "lower alkyl optionally substituted by substituent E" represented by $R^{3e}$ include methyl, ethyl, and trifluoromethyl.

$R^{3d}$ in preferred embodiments is —N$(CH_3)_2$, —OCH$_3$, or pyrrolidinyl.

Examples of the solvent of the reaction include acetonitrile, tetrahydrofuran, dioxane, diethyl ether, dichloromethane, chloroform, toluene, xylene, ethyl acetate, N,N-dimethylformamide, N,N-dimethylacetamide, dimethylimidazolidinone, and mixed solvents thereof.

The amount of the compound (V1) used is approximately 1.0 to 3.0 molar equivalents with respect to compound (X1), or the compound (V1) may be used as a solvent.

The reaction temperature is usually 0° C. to reflux temperature, preferably room temperature.

The reaction time is usually 30 minutes to 50 hours, preferably 2 to 8 hours.

The compound (X2) may be isolated by a general purification method (extraction, distillation, column chromatography, crystallization, etc.) or can also be used in the next reaction without being isolated.

(Step A')

Compound (X2) may be obtained through the following reaction:

[Chemical Formula 119]

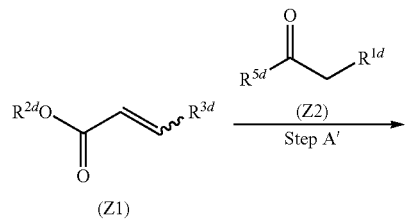

49

-continued

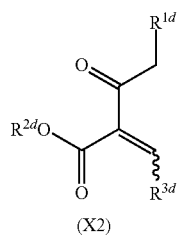

(X2)

(wherein $R^{5d}$ is halogen, lower alkyloxy optionally substituted by substituent E, or —O—SO$_2$—$R^{5e}$; and each of the other symbols is as defined above).

The compound (Z1) may be a commercially available reagent or can be obtained by a method known in the art.

Examples of the "lower alkyl optionally substituted by substituent E" represented by $R^{2d}$ include methyl, ethyl, n-propyl, isopropyl, and tert-butyl.

Examples of the "carbocyclyl lower alkyl optionally substituted by substituent E" represented by $R^{2d}$ include benzyl and 4-methoxybenzyl.

Examples of the "heterocyclyl lower alkyl optionally substituted by substituent E" represented by $R^{2d}$ include pyridylmethyl.

$R^{2d}$ in preferred embodiments is methyl, ethyl, n-propyl, isopropyl, tert-butyl, benzyl, 4-methoxybenzyl, or the like.

Examples of the "lower alkyloxy optionally substituted by substituent E" represented by $R^{3d}$ include methoxy and ethoxy.

When $R^{3d}$ is —N($R^{3e}$)$_2$, examples of the "lower alkyl optionally substituted by substituent E" represented by $R^{3e}$ include methyl, ethyl, and trifluoromethyl.

$R^{3d}$ in preferred embodiments is —N(CH$_3$)$_2$, —OCH$_3$, or pyrrolidinyl.

The compound (Z2) may be a commercially available reagent or can be obtained by a method known in the art.

Examples of the "lower alkyloxy optionally substituted by substituent E" represented by $R^{1d}$ include methoxy, ethoxy, isopropoxy, trichloromethoxy, and trifluoromethoxy. Methoxy is preferred.

Examples of the "carbocyclyl lower alkyloxy optionally substituted by substituent E" represented by $R^{1d}$ include benzyloxy, phenethyloxy, 2,4-trifluorobenzyloxy, and 4-methoxybenzyloxy. Benzyloxy is preferred.

Examples of the "heterocyclyl lower alkyloxy optionally substituted by substituent E" represented by $R^{1d}$ include pyridylmethyloxy.

$R^{1d}$ in preferred embodiments is hydrogen, chloro, bromo, methoxy, or benzyloxy.

Examples of preferred embodiments of $R^{5d}$ include chloro, bromo, methoxy, ethoxy, methanesulfonyloxy, trifluoromethanesulfonyloxy, and p-toluenesulfonyloxy.

Examples of the solvent of the reaction include acetonitrile, tetrahydrofuran, dioxane, diethyl ether, dichloromethane, chloroform, toluene, xylene, ethyl acetate, N,N-dimethylformamide, N,N-dimethylacetamide, dimethylimidazolidinone, and mixed solvents thereof.

The amount of the compound (Z2) used is approximately 1.0 to 3.0 molar equivalents with respect to compound (Z1).

The reaction temperature is usually −10° C. to reflux temperature, preferably room temperature.

The reaction time is usually 10 minutes to 10 hours, preferably 1 to 4 hours.

Tertiary amine is added, if necessary. Examples of the tertiary amine include pyridine, triethylamine, dimethylaminopyridine, and N-methylmorpholine.

50

The compound (X2) may be isolated by a general purification method (extraction, distillation, column chromatography, crystallization, etc.) or can also be used in the next reaction without being isolated.

(Step B)

This step is the step of reacting compound (X2) with compound (V2), if desired in the presence of a base, to obtain a solution containing compound (X3) or a salt thereof, as shown below in the reaction formula:

[Chemical Formula 120]

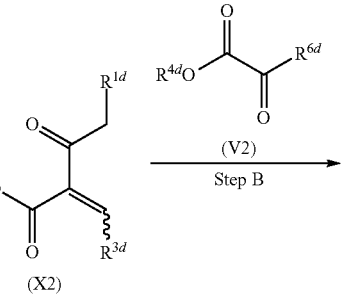

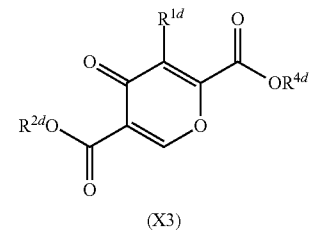

(X3)

(wherein each symbol is as defined above).

Examples of the "lower alkyloxy optionally substituted by substituent E" represented by $R^{1d}$ include methoxy, ethoxy, isopropoxy, trichloromethoxy, and trifluoromethoxy. Methoxy is preferred.

Examples of the "carbocyclyl lower alkyloxy optionally substituted by substituent E" represented by $R^{1d}$ include benzyloxy, phenethyloxy, 2,4-trifluorobenzyloxy, and 4-methoxybenzyloxy. Benzyloxy is preferred.

Examples of the "heterocyclyl lower alkyloxy optionally substituted by substituent E" represented by $R^{1d}$ include pyridylmethyloxy.

$R^{1d}$ in Preferred embodiments is hydrogen, chloro, bromo, methoxy, or benzyloxy.

Examples of the "lower alkyl optionally substituted by substituent E" represented by $R^{2d}$ include methyl, ethyl, n-propyl, isopropyl, and tert-butyl.

Examples of the "carbocyclyl lower alkyl optionally substituted by substituent E" represented by $R^{2d}$ include benzyl and 4-methoxybenzyl.

Examples of the "heterocyclyl lower alkyl optionally substituted by substituent E" represented by $R^{2d}$ include pyridylmethyl.

$R^{2d}$ in preferred embodiments is methyl, ethyl, n-propyl, isopropyl, tert-butyl, benzyl, 4-methoxybenzyl, or the like.

Examples of the "lower alkyloxy optionally substituted by substituent E" represented by $R^{3d}$ include methoxy and ethoxy.

Examples of the "lower alkyl optionally substituted by substituent E" represented by $R^{3e}$ include methyl, ethyl, and trifluoromethyl.

$R^{3d}$ in preferred embodiments is —N(CH$_3$)$_2$, —OCH$_3$, or pyrrolidinyl.

The compound (V2) can be obtained as a commercially available reagent or by a method known in the art.

Examples of the "lower alkyl optionally substituted by substituent E" represented by $R^{4d}$ include methyl, ethyl, n-propyl, isopropyl, and tert-butyl.

Examples of the "carbocyclyl lower alkyl optionally substituted by substituent E" represented by $R^{4d}$ include benzyl and 4-methoxybenzyl.

Examples of the "heterocyclyl lower alkyl optionally substituted by substituent E" represented by $R^{4d}$ include pyridylmethyl.

Examples of preferred embodiments of $R^{4d}$ include methyl, ethyl, n-propyl, isopropyl, tert-butyl, benzyl, and 4-methoxybenzyl. Particularly, methyl or ethyl is preferred.

Examples of preferred embodiments of $R^{5d}$ include chloro, bromo, methoxy, ethoxy, acetoxy, methanesulfonyloxy, trifluoromethanesulfonyloxy, and p-toluenesulfonyloxy. Particularly, chloro, methoxy, or ethoxy is preferred.

Examples of the reaction solvent include acetonitrile, tetrahydrofuran, dioxane, toluene, xylene, ethyl acetate, N,N-dimethylformamide, N,N-dimethylacetamide, dimethylimidazolidinone, N-methylmorpholine, N-methylpyrrolidinone, and mixed solvents thereof.

Examples of the base include n-butyllithium, tert-butyllithium, sodium tert-butoxide, potassium-tert-butoxide, sodium tert-pentoxide, sodium methoxide, sodium ethoxide, sodium hydride, lithium diisopropylamide, and lithium bis(trimethylsilyl)amide.

The amount of the base used is approximately 1.0 to 5.0 molar equivalents with respect to compound (X2).

The amount of the compound (V2) used is approximately 1.5 to 5.0 molar equivalents with respect to compound (X2), or the compound (V2) may be used as a solvent.

The reaction temperature is usually −80° C. to reflux temperature, preferably −20° C. to 50° C.

The reaction time is usually 30 minutes to 50 hours, preferably 2 to 12 hours.

The compound (X3) may be isolated by a general purification method (extraction, distillation, column chromatography, crystallization, etc.) or can also be used in the next reaction without being isolated. Preferably, the compound (X3) is isolated as crystals free from impurities by crystallization.

(Step B')

This step is the step of reacting compound (X2) with compound (V2) and compound (V2'), if desired in the presence of a base, to obtain compound (X4') or a salt thereof as shown below in the reaction formula:

[Chemical Formula 121]

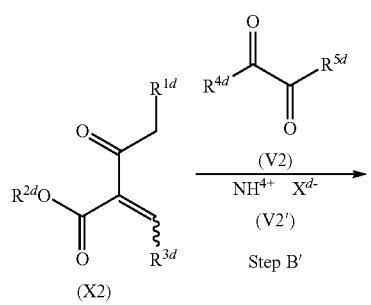

-continued

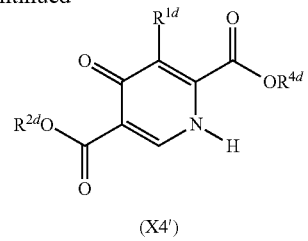

(wherein each symbol is as defined above).

Examples and preferred embodiments of $R^{1d}$, $R^{2d}$, $R^{3d}$, $R^{4d}$, and $R^{5d}$ in the formulae (X2) and (V2) are the same as above.

Examples of the reaction solvent include acetonitrile, tetrahydrofuran, dioxane, toluene, xylene, ethyl acetate, N,N-dimethylformamide, N,N-dimethylacetamide, dimethylimidazolidinone, N-methylmorpholine, N-methylpyrrolidinone, and mixed solvents thereof.

Examples of the base include n-butyllithium, tert-butyllithium, sodium tert-butoxide, potassium-tert-butoxide, sodium tert-pentoxide, sodium methoxide, sodium ethoxide, sodium hydride, lithium diisopropylamide, and lithium bis(trimethylsilyl)amide.

The amount of the base used is approximately 1.0 to 5.0 molar equivalents with respect to compound (X2).

The amount of the compound (V2) used is approximately 1.0 to 3.0 molar equivalents with respect to compound (X2), or the compound (V2) may be used as a solvent.

The reaction temperature is usually −80° C. to reflux temperature, preferably −20° C. to 30° C.

The reaction time is usually 10 minutes to 10 hours, preferably 30 minutes to 4 hours.

Subsequently, compound (V2') is added to the reaction solution and reacted therewith.

Examples of the compound (V2') include ammonium acetate, ammonium chloride, ammonium bromide, ammonium sulfate, ammonium bisulfate, ammonium formate, ammonium nitrate, ammonium hydroxide, ammonium phosphate, $NH_4^+BF_4^-$, $NH_4^+PF_6^-$, $NH_4^+Ph\text{-}SO_3^-$, $NH_4^+CH_3\text{-}Ph\text{-}SO_3^-$, and $NH_4^+CH_3\text{—}SO_3^-$. The compound (V2') is preferably ammonium acetate, ammonium chloride, ammonium sulfate, ammonium bisulfate, or ammonium formate. (In this context, Ph represents a phenyl group.)

The amount of the compound (V2') used is approximately 1.0 to 3.0 molar equivalents with respect to compound (X2).

The reaction temperature is usually 0° C. to reflux temperature, preferably 20° C. to 80° C.

The reaction time is usually 10 minutes to 10 hours, preferably 30 minutes to 4 hours.

The compound (X4') may be isolated by a general purification method (extraction, distillation, column chromatography, crystallization, etc.) or can also be used in the next reaction without being isolated. Preferably, the compound (X4') is isolated as crystals free from impurities by crystallization.

(Step C)

This step is the step of reacting compound (X3) or a salt thereof with compound (V3) or a salt thereof to obtain compound (X4) or a salt thereof, as shown below in the reaction formula:

[Chemical Formula 122]

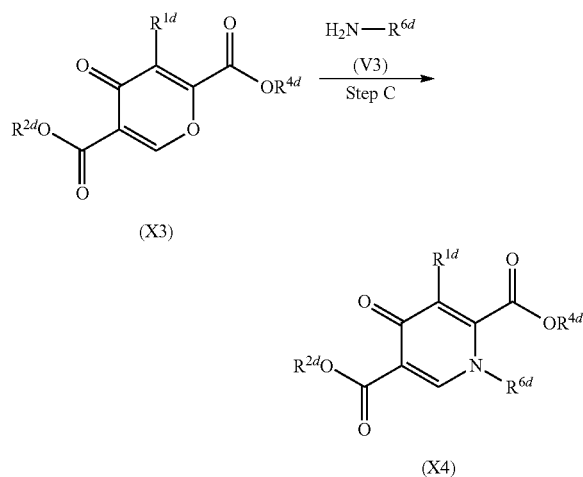

(wherein each symbol is as defined above).

Examples and preferred embodiments of $R^{1d}$, $R^{2d}$, and $R^{4d}$ in the formula (X3) are the same as those described above in Step B.

The compound (V3) can be obtained as a commercially available reagent or by a method known in the art.

Examples of the "lower alkyl optionally substituted by substituent E" represented by $R^{6d}$ include $HC(=O)-CH_2-$, $CH(-OH)_2-CH_2-$, $CH_3O-CH(-OH)-CH_2-$, dimethoxyethyl, diethoxyethyl, $HO-CH_2-CH(-OH)-CH_2-$,

[Chemical Formula 123]

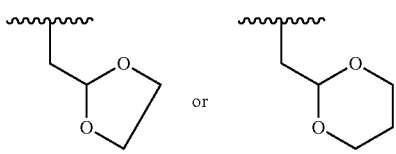

Examples of the "lower alkenyl optionally substituted by substituent E" represented by $R^{6d}$ include $CH_2=CH-CH_2-$.

Examples of the reaction solvent include acetonitrile, tetrahydrofuran, dioxane, toluene, xylene, ethyl acetate, N,N-dimethylformamide, N,N-dimethylacetamide, dimethylimidazolidinone, N-methylmorpholine, N-methylpyrrolidinone, methanol, ethanol, isopropanol, and mixed solvents thereof.

The amount of the compound (V3) used is approximately 1.0 to 2.0 molar equivalents with respect to compound (X3).

The reaction temperature is usually 0° C. to reflux temperature, preferably 20° C. to 70° C.

The reaction time is usually 30 minutes to 50 hours, preferably 2 to 12 hours.

When $R^{6d}$ in the formed compound (X4) is not an aldehyde group or a group having an equivalent thereof, such as $HC(=O)-CH_2-$, $CH_3O-CH(-OH)-CH_2-$, or $CH(-OH)_2-CH_2-$, this moiety can be converted to $HC(=O)-CH_2-$, $CH_3O-CH(-OH)-CH_2-$, or $CH(-OH)_2-CH_2-$, which is an aldehyde group or a group having an equivalent thereof, by deprotection methods for protective groups in aldehyde groups described in Protective Groups in Organic Synthesis, Theodora W Greene (John Wiley & Sons) or a method known in the art as described in International Publication No. WO 2006/116764 or 2006/088173.

When $R^{6d}$ in compound (X4) is, for example, dimethoxyethyl, this moiety can be converted to $HC(=O)-CH_2-$ by the addition of an acid to the solution containing compound (X4). The acid is not particularly limited and is exemplified by hydrochloric acid, hydrobromic acid, sulfuric acid, nitric acid, phosphoric acid, p-toluenesulfonic acid, methanesulfonic acid, formic acid, acetic acid, trifluoroacetic acid, maleic acid, and oxalic acid. The amount of the acid used is 2.0 to 10.0 molar equivalents with respect to compound (X4). Acetic acid or formic acid may be used as a solvent and may be used as a mixture with any of the acids described above.

The reaction temperature is usually approximately 0° C. to 80° C., preferably 10° C. to 40° C.

The reaction time is usually 30 minutes to 50 hours, preferably 2 to 12 hours.

When the amino group is protected with an amino protective group, a compound with a deprotected amino group can also be obtained by deprotection methods for protective groups in amino groups described in Protective Groups in Organic Synthesis, Theodora W Greene (John Wiley & Sons) or a method known in the art. The order of deprotection reactions can be changed appropriately.

When $R^{6d}$ is an amino protective group, the amino protective group in compound (X4) can be subjected to deprotection reaction, followed by reaction with compound (V3') in the subsequent step, as in Step C' shown below, to obtain the compound (X4) of interest.

The compound (X4) may be isolated by a general purification method (extraction, distillation, column chromatography, crystallization, etc.) or can also be used in the next reaction without being isolated. Preferably, the compound (X4) is isolated as crystals free from impurities by crystallization.

(Step C')

This step is the step of reacting compound (X4') or a salt thereof with compound (V3'), if desired in the presence of a base, to obtain compound (X4) or a salt thereof, as shown below in the reaction formula:

[Chemical Formula 124]

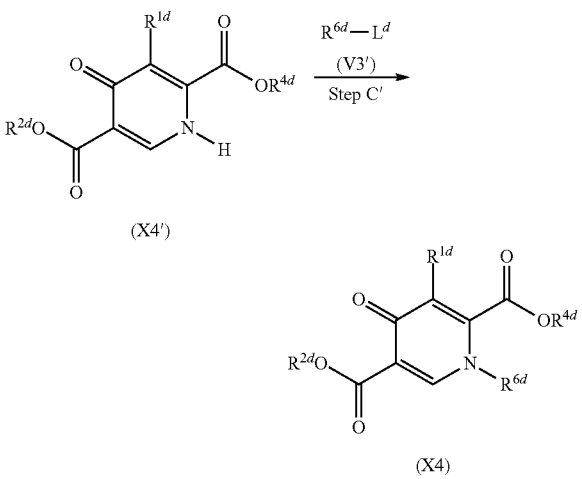

(wherein each symbol is as defined above).

Examples and preferred embodiments of $R^{1d}$, $R^{2d}$, $R^{4d}$, and $R^{6d}$ in the formulae (X4') and (V3') are the same as those described above in Step B' and Step C.

Examples of the "leaving group" represented by $L^d$ include halogen, —O—SO$_2$—CH$_3$, —O—SO$_2$—CF$_3$, —O—SO$_2$-Ph, and —O—SO$_2$-Ph-CH$_3$. Halogen is preferred. (In this context, Ph represents a phenyl group.)

When $R^{6d}$ in the formed compound (X4) does not have an aldehyde group or an equivalent thereof, such as HC(=O)—CH$_2$—, CH$_3$O—CH(—OH)—CH$_2$—, or CH(—OH)$_2$—CH$_2$—, the method of converting this moiety to the aldehyde group or the equivalent thereof is also the same as above.

Examples of the reaction solvent include acetonitrile, ethyl acetate, N,N-dimethylformamide, N,N-dimethylacetamide, dimethylimidazolidinone, N-methylmorpholine, N-methylpyrrolidinone, and mixed solvents thereof.

Examples of the base include potassium carbonate, cesium carbonate, sodium hydride, n-butyllithium, tert-butyllithium, sodium tert-butoxide, potassium-tert-butoxide, sodium tert-pentoxide, sodium methoxide, triethylamine, 4-dimethylaminopyridine, diisopropylethylamine, and DBU (1,8-diazabicyclo[5.4.0]undec-7-ene).

The amount of the base used is approximately 1.0 to 5.0 molar equivalents with respect to compound (X4').

The amount of the compound (V3') used is approximately 1.0 to 4.0 molar equivalents with respect to compound (X4'), or the compound (V3') may be used as a solvent.

The reaction temperature is usually 0° C. to reflux temperature, preferably 20° C. to 80° C.

The reaction time is usually 30 minutes to 24 hours, preferably 1 to 8 hours.

The compound (X4) may be isolated by a general purification method (extraction, distillation, column chromatography, crystallization, etc.) or can also be used in the next reaction without being isolated. Preferably, the compound (X4) is isolated as crystals free from impurities by crystallization.

(Step D)

This step is the step of reacting compound (X4) or a salt thereof with compound (V5) or compound (V5'), if desired in the presence of an acid, to obtain compound (X5) or compound (X5'), or a salt thereof, as shown below in the reaction formula:

[Chemical Formula 125]

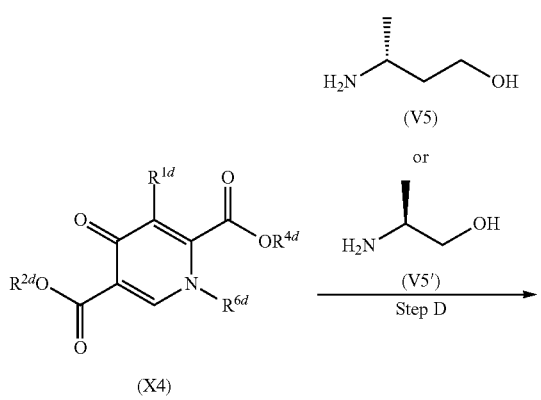

(X4)

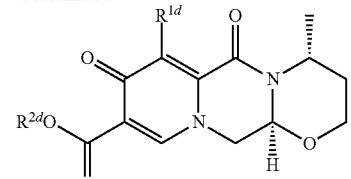

(X5)

or

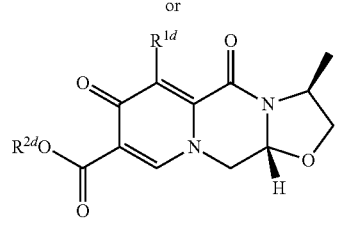

(X5')

(wherein $R^{1d}$, $R^{2d}$, and $R^{4d}$ are as defined above; $R^{6d}$ is an aldehyde group or an equivalent thereof, such as HC(=O)—CH$_2$—, CH$_3$O—CH(—OH)—CH$_2$—, or CH(—OH)$_2$—CH$_2$—; and when $R^{6d}$ is not the aldehyde or the equivalent thereof, the method described above in Step C is performed).

Examples and preferred embodiments of $R^{1d}$, $R^{2d}$, and $R^{4d}$ in the formulae (X4), (X5), and (X5') are the same as above.

The compound (V5) and the compound (V5') are commercially available reagents.

Examples of the reaction solvent include acetonitrile, tetrahydrofuran, dioxane, toluene, xylene, ethyl acetate, N,N-dimethylformamide, N,N-dimethylacetamide, dimethylimidazolidinone, N-methylmorpholine, N-methylpyrrolidinone, and mixed solvents thereof.

Examples of the acid include acetic acid, trifluoroacetic acid, formic acid, and methanesulfonic acid. The amount of the acid used is 0.5 to 3.0 molar equivalents with respect to compound (X4).

The amount of the compound (V5) or the compound (V5') used is approximately 1.0 to 2.0 molar equivalents with respect to compound (X4), or the compound (V5) or the compound (V5') may be used as a solvent.

In this reaction, 1.0 to 5.0 molar equivalents of an alcohol reagent may be added, if desired, to thereby improve the reaction rate. The alcohol reagent is preferably methanol, ethanol, or isopropanol, particularly preferably methanol.

The reaction temperature is usually 20° C. to reflux temperature, preferably 60° C. to 80° C.

The reaction time is usually 30 minutes to 24 hours, preferably 1 to 8 hours.

The compound (X5) or the compound (X5') may be isolated by a general purification method (extraction, distillation, column chromatography, crystallization, etc.) or can also be used in the next reaction without being isolated. Preferably, the compound (X5) or the compound (X5') is isolated as crystals free from impurities by crystallization.

(Step E)

This step is the step of reacting compound (X5) or compound (X5'), or a salt thereof with compound (V6) or a salt thereof to obtain compound (X6) or compound (X6'), as shown below in the reaction formula:

[Chemical Formula 126]

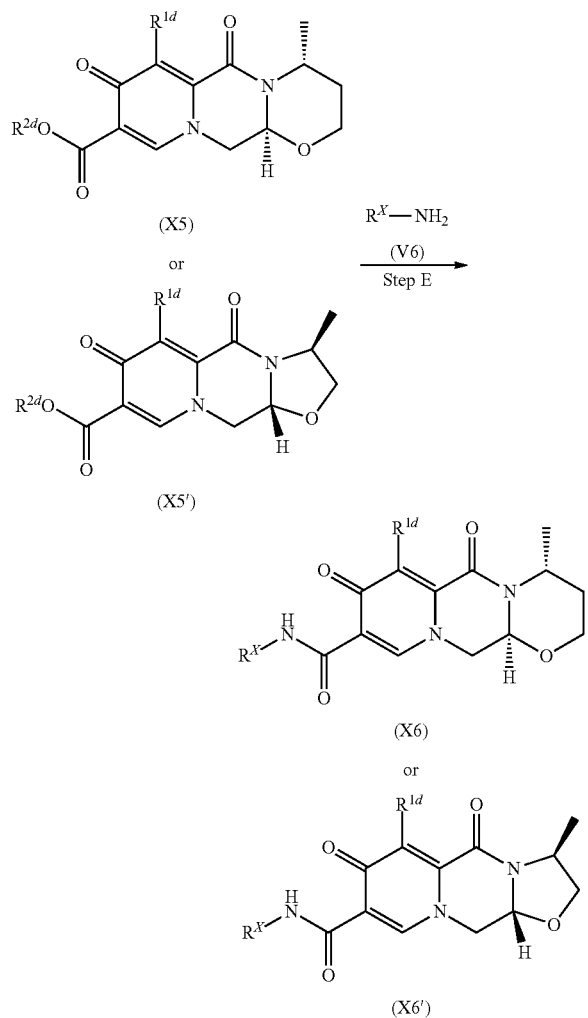

(wherein $R^{1d}$ and $R^{2d}$ are as defined above; $R^X$ is carbocyclyl optionally substituted by substituent E, heterocyclyl optionally substituted by substituent E, carbocyclyl lower alkyl optionally substituted by substituent E, or heterocyclyl lower alkyl optionally substituted by substituent E).

Examples of the "carbocyclyl optionally substituted by substituent E" represented by $R^X$ include phenyl, 2,4-difluorophenyl, and cyclohexyl.

Examples of the "heterocyclyl optionally substituted by substituent E" represented by $R^X$ include pyridyl, morpholinyl, and isoxazolyl.

Examples of the "carbocyclyl lower alkyl optionally substituted by substituent E" represented by $R^X$ include benzyl, 4-methoxybenzyl, and 2,4-difluorobenzyl.

Examples of the "heterocyclyl lower alkyl optionally substituted by substituent E" represented by $R^X$ include pyridylmethyl and isoxazolylmethyl.

Preferred examples of substituent E for the "carbocyclyl optionally substituted by substituent E", "heterocyclyl optionally substituted by substituent E", "carbocyclyl lower alkyl optionally substituted by substituent E", and "heterocyclyl lower alkyl optionally substituted by substituent E" represented by $R^X$ include halogen, cyano, hydroxy, carboxy, formyl, amino, oxo, nitro, lower alkyl, halogeno lower alkyl, lower alkyloxy, halogeno lower alkyloxy, lower alkyloxy lower alkyl, lower alkyloxy lower alkyloxy, lower alkylcarbonyl, lower alkyloxycarbonyl, lower alkyloxycarbonylamino, lower alkylamino, lower alkylcarbonylamino, lower alkylaminocarbonyl, lower alkylsulfonyl, and lower alkylsulfonylamino. More preferred examples thereof include halogen, cyano, hydroxy, carboxy, formyl, amino, lower alkyl, halogeno lower alkyl, and lower alkyloxy. Further preferred examples thereof include halogen, lower alkyl, and lower alkyloxy. Halogen is most preferred.

$R^X$ in preferred embodiments is "carbocyclyl lower alkyl optionally substituted by substituent E" or "heterocyclyl lower alkyl optionally substituted by substituent E". $R^X$ in more preferred embodiments is "carbocyclyl lower alkyl optionally substituted by substituent E". $R^X$ in further preferred embodiments is "carbocyclyl lower alkyl optionally substituted by halogen". $R^X$ in the most preferred embodiment is 2,4-difluorobenzyl.

When $R^{1d}$ is hydrogen, this moiety can be converted appropriately to halogen using a halogenating agent such as N-bromosuccinimide, N-chlorosuccinimide, or sulfuryl chloride.

$R^{1d}$ can be selected appropriately according to the reactivity of the reaction substrate. The order of these reactions can be changed appropriately.

When $R^{2d}$ is hydrogen, compound (X6) or compound (X6') can be induced through general dehydration-condensation reaction (e.g., a method using a condensation agent, an acid chloride formation method, or an acid anhydride formation method) of the carboxyl group and compound (V6). For example, amide compound (X6) or compound (X6') can be obtained through reaction at 0° C. to 60° C., preferably 10° C. to 40° C., for 1 hour to 48 hours, preferably 1 hour to 24 hours, in the presence of a dehydration-condensation agent such as dicyclohexylcarbodiimide, carbonyldiimidazole, dicyclohexylcarbodiimide-N-hydroxybenzotriazole, 4-(4, 6-dimethoxy-1,3,5-triazin-2-yl)-4-methylmorpholinium chloride, 2-(7-aza-1H-benzotriazol-1-yl)-1,1,3,3-tetramethyluronium hexafluorophosphate, or WSC.

When $R^{2d}$ is not hydrogen, this moiety is converted to a carboxyl group through general deprotection reaction of the carboxyl protective group. Compound (X6) or compound (X6') can be induced through the same dehydration-condensation reaction as above of the formed carboxyl group and compound (V6). The carboxyl protective group is exemplified by carboxyl protective groups described in, for example, Protective Groups in Organic Synthesis, Theodora W Greene (John Wiley & Sons). Preferred examples thereof include methyl, ethyl, tert-butyl, methoxymethyl, allyl, benzyl, and p-methoxybenzyl groups.

When $R^{2d}$ is "lower alkyl optionally substituted by substituent E", compound (X6) or compound (X6') can also be induced through aminolysis reaction using compound (V6).

The compound (X6) or the compound (X6') may be isolated by a general purification method (extraction, distillation, column chromatography, crystallization, etc.) or can also be used in the next reaction without being isolated. Preferably, the compound (X6) or the compound (X6') is isolated as crystals free from impurities by crystallization.

Compound X6 or compound X6' may also be obtained by the following Step E' and Step D':

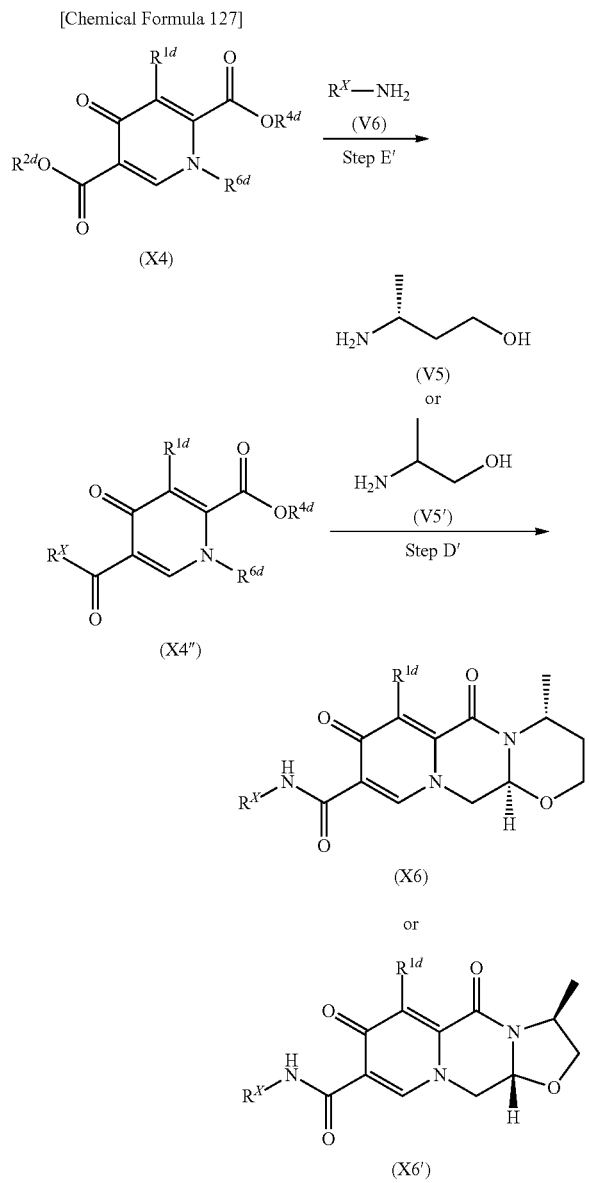

(wherein $R^{1d}$, $R^{2d}$, $R^{4d}$, $R^{6d}$, and $R^X$ are as defined above; $R^{6d}$ is an aldehyde group or an equivalent thereof such as HC(=O)—CH$_2$—, CH$_3$O—CH(—OH)—CH$_2$—, or CH(—OH)$_2$—CH$_2$—; and when $R^{6d}$ is not the aldehyde or the equivalent thereof, the method described above in Step C is performed).

(Step E')

This step is the step of reacting compound (X5) or compound (X4), or a salt thereof with compound (V6) or a salt thereof to obtain compound (X4").

Examples and preferred embodiments of $R^{1d}$, $R^{2d}$, $R^{4d}$, and $R^X$ are the same as above.

When $R^{2d}$ is hydrogen, compound (X4") can be induced through general dehydration-condensation reaction (e.g., a method using a condensation agent, an acid chloride formation method, or an acid anhydride formation method) of the carboxyl group and compound (V6). For example, amide compound (X6) can be obtained through reaction at 0° C. to 60° C., preferably 10° C. to 40° C., for 1 hour to 48 hours, preferably 1 hour to 24 hours, in the presence of a dehydration-condensation agent such as dicyclohexylcarbodiimide, carbonyldiimidazole, dicyclohexylcarbodiimide-N-hydroxybenzotriazole, 4-(4,6-dimethoxy-1,3,5-triazin-2-yl)-4-methylmorpholinium chloride, 2-(7-aza-1H-benzotriazol-1-yl)-1,1,3,3-tetramethyluronium hexafluorophosphate, or WSC.

When $R^{2d}$ is not hydrogen, this moiety is converted to a carboxyl group through general deprotection reaction of the carboxyl protective group. Compound (X4") can be induced through the same dehydration-condensation reaction as above of the formed carboxyl group and compound (V6). The carboxyl protective group is exemplified by carboxyl protective groups described in, for example, Protective Groups in Organic Synthesis, Theodora W Greene (John Wiley & Sons). Preferred examples thereof include methyl, ethyl, tert-butyl, methoxymethyl, allyl, benzyl, and p-methoxybenzyl groups. A methyl group is particularly preferred.

When $R^{2d}$ is "lower alkyl optionally substituted by substituent E", compound (X4") can also be induced through aminolysis reaction of compound (V6).

(Step D')

This step is the step of reacting the compound (X4') obtained in Step E' with compound (V5) or compound (V5'), if desired in the presence of an acid, to obtain compound (X6) or compound (X6'), or a salt thereof.

(Step F)

This step is the step of obtaining compound (Y1) or compound (Y2), or a salt thereof from compound (X6) or compound (X6'), as shown below in the reaction formula:

[Chemical Formula 128]

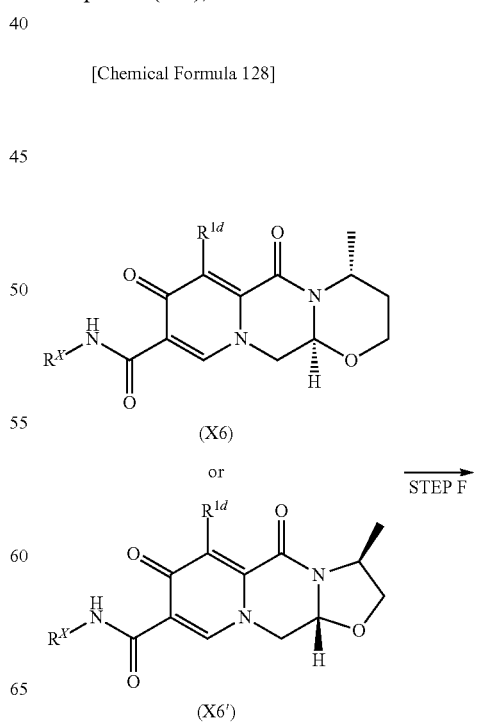

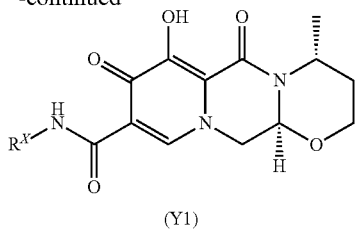

(Y1)

or

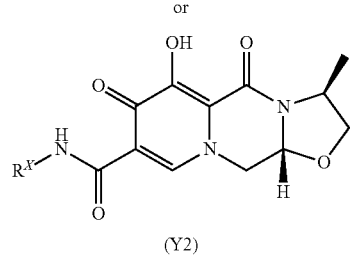

(Y2)

(wherein each symbol is as defined above).

Examples and preferred embodiments of $R^X$ are as defined above.

When $R^{1d}$ is lower alkyloxy optionally substituted by substituent E, carbocyclyl lower alkyloxy optionally substituted by substituent E, heterocyclyl lower alkyloxy optionally substituted by substituent E, or —OSi($R^{1e}$)$_3$, this moiety can be converted to a hydroxy group through hydroxy deprotection reaction known in the art described in, for example, Protective Groups in Organic Synthesis, Theodora W Greene (John Wiley & Sons).

Specifically, when $R^{1d}$ is methyloxy, this moiety can be converted to a hydroxy group using a reagent such as (CH$_3$)$_3$—Si—I, BBr$_3$, or BF$_3$.Et$_2$O. When $R^{1d}$ is benzyloxy, this moiety can be converted to a hydroxy group using Pd—C/H$_2$ gas, a Raney-Ni reagent, or the like. When $R^{1d}$ is —OSi(CH$_3$)$_3$, this moiety can be converted to a hydroxy group using a tetramethylammonium fluoride reagent.

When $R^{1d}$ is halogen, this moiety can be converted to a hydroxy group by reaction with potassium trimethylsilanolate or lithium trimethylsilanolate and the subsequent addition of an aqueous solution of an inorganic acid. Examples of other conditions for the conversion reaction of halogen to a hydroxy group also include use of sodium hydride/water (Bioorganic Medicinal Chemistry Letters, 17, 1713, 2007), potassium hydroxide/tris(dibenzylideneacetone)dipalladium (Pd$_2$dba$_3$)/di-tert-butylarylphosphine (Journal of the American Chemical Society, 128, 10694, 2006), potassium phosphate hydrate (K$_3$PO$_4$.H$_2$O)/tris(dibenzylideneacetone)dipalladium (Pd$_2$dba$_3$)/tri-tert-butylphosphine (Tetrahedron Letters, 48, 473, 2007). As described above, the halogen represented by $R^{1d}$ in the starting material may be derivatized directly. Thus, this approach requires a smaller number of reaction steps and may construct a more advantageous industrial production method, compared with the method involving alcohol protection and/or deprotection reactions.

When $R^{1d}$ is hydrogen, this $R^{1d}$ may be converted to halogen through reaction with a halogenating agent such as N-bromosuccinimide, N-chlorosuccinimide, or sulfuryl chloride, followed by reaction with potassium trimethylsilanolate or lithium trimethylsilanolate and the subsequent addition of an aqueous solution of an inorganic acid in the same way as above to induce a hydroxy group. Accordingly, $R^{1d}$ can be selected appropriately from among these substituents according to the reactivity of the reaction substrate.

In the step, the order of these reactions can be changed appropriately.

The compound (Y1) or the compound (Y2) can be isolated by a general purification method (extraction, distillation, column chromatography, crystallization, etc.).

The compound (Y1) or the compound (Y2) can be converted to a salt by the desired method. The salt is preferably a basic salt, more preferably an alkali metal salt such as sodium salt, potassium salt, or lithium. The most preferred example thereof includes sodium salt.

The salt of compound (Y1) or compound (Y2) can be deposited by dissolving the compound (Y1) or the compound (Y2) in an organic solvent or a mixed solution of an organic solvent and water and adding an aqueous alkali solution or an organic base to the solution, followed by stirring. This dissolution is performed by heating, if necessary. Also, the salt deposition is performed by cooling, if necessary.

For example, ethanol, methanol, isopropyl alcohol, acetone, acetonitrile, tetrahydrofuran, or dichloromethane may be used as the organic solvent.

In the present invention, preferably, the steps described above can be combined arbitrarily to obtain compound (Y1) or compound (Y2), or a salt thereof. Also, one or two or more chemical reactions well known by those skilled in the art may be combined appropriately before and/or after each step.

Hereinafter, the present invention will be described more specifically with reference to Examples and Test Examples of the present invention. However, the present invention is not limited to them. Each symbol used in Examples is as follows:

Me: Methyl

Et: Ethyl

Bn: Benzyl

Ph: Phenyl

DMI: Dimethylimidazolidinone

THF: Tetrahydrofuran

WSC: N-ethyl-N'-(3-dimethylaminopropyl)carbodiimide

HATU: O-(7-azabenzotriazol-1-yl)-N,N,N',N'-tetramethyluronium hexafluorophosphate DBU: 1,8-diazabicyclo[5.4.0]-7-undecene DMF: N,N-dimethylformamide HOBt: 1-hydroxybenzotriazole NBS: N-bromosuccinimide Example 1

[Chemical Formula 129]

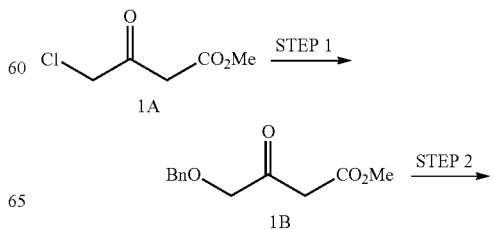

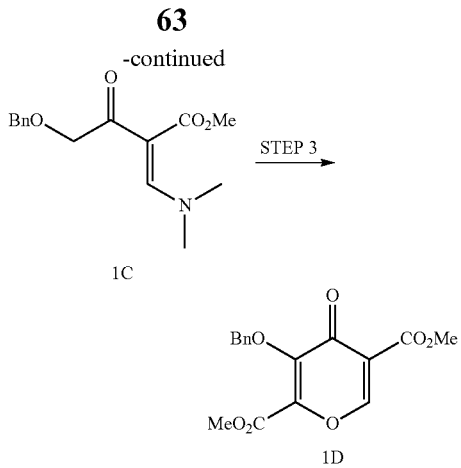

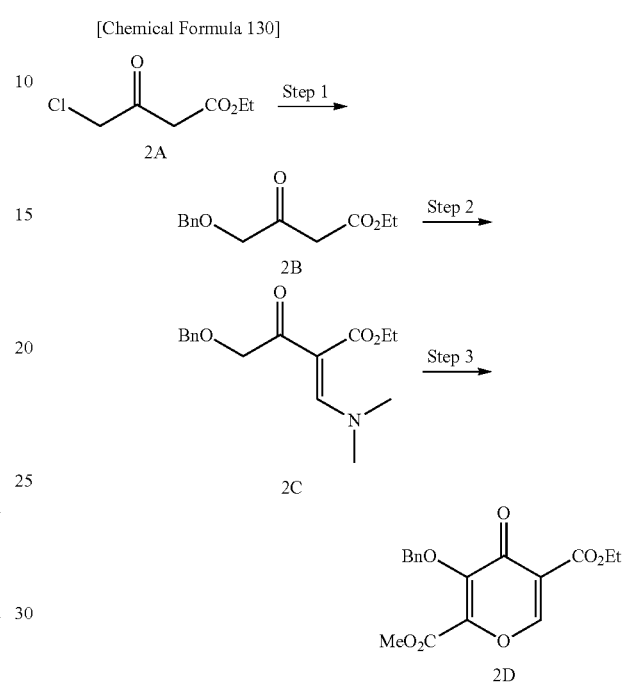

Step 1

A THF (3 ml) solution of benzyl alcohol (1.00 g, 9.25 mmol) was added to a THF (4 ml) suspension of sodium tert-pentoxide (2.55 g, 23.2 mmol) at room temperature in a nitrogen atmosphere, and the mixture was stirred at 40° C. for 2 hours. This reaction solution was cooled in an ice bath, and a THF (3 ml) solution of compound 1A (1.53 g, 10.2 mmol) was added dropwise thereto at 0-10° C. The reaction solution was stirred at room temperature for 2 hours, and 2 N hydrochloric acid (15 ml) was then added thereto, followed by extraction two times with ethyl acetate. The combined extracts were washed with water, a saturated aqueous solution of sodium bicarbonate, water, and saturated saline in this order and then dried over anhydrous sodium sulfate. The solvent was distilled off, and the obtained oil was purified by silica gel column chromatography (n-hexane-ethyl acetate: 4:1, v/v) to obtain 1.89 g (yield: 92%) of compound 1B as an oil.

$^1$H-NMR (CDCl$_3$) δ: 3.56 (2H, s), 3.71 (3H, s), 4.14 (2H, s), 4.59 (2H, s), 7.27-7.42 (5H, m).

Step 2

Compound 1B (1.80 g, 8.1 mmol) was dissolved in 1,4-dioxane (18 mL). To the solution, N,N-dimethylformamide dimethyl acetal (1.45 g, 12.2 mmol) was added, and the mixture was stirred at room temperature for 6 hours. The reaction solution was concentrated under reduced pressure. Then, the residue was purified by silica gel column chromatography (n-hexane-ethyl acetate: 1:4, v/v) to obtain 1.77 g (yield: 79%) of compound 1C as an oil.

$^1$H-NMR (CDCl$_3$) δ: 2.90 (3H, br), 3.25 (3H, br), 3.69 (3H, s), 4.45 (2H, s), 4.59 (2H, s), 7.24-7.40 (5H, m), 7.73 (s, 1H).

Step 3

Sodium tert-butoxide (2.55 g, 23.2 mmol), dimethyl oxalate (639 mg, 5.41 mmol), and DMI (3 ml) were added to a three-neck flask in a nitrogen atmosphere, and a DMI (2 ml) solution of compound 1C (0.50 g, 1.80 mmol) was added dropwise thereto at 25-30° C. After stirring at room temperature for 7 hours, 2 N hydrochloric acid (10 ml) was added thereto, and the mixture was stirred at room temperature for 15 hours. After extraction two times with ethyl acetate, the combined extracts were washed with water, a saturated aqueous solution of sodium bicarbonate, water, and saturated saline in this order and then dried over anhydrous sodium sulfate. The solvent was distilled off, and the obtained residue was purified by silica gel column chromatography (n-hexane-ethyl acetate: 2:1→1:1, v/v) to obtain 488 mg (yield: 85%) of compound 1D as white crystals.

$^1$H-NMR (CDCl$_3$) δ: 3.89 (3H, s), 3.93 (3H, s), 5.34 (2H, s), 7.32-7.40 (3H, m), 7.45-7.49 (2H, m), 8.50 (1H, s).

Example 2

[Chemical Formula 130]

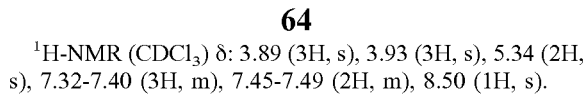

Step 1

A DMI (3 ml) solution of benzyl alcohol (0.66 g, 6.1 mmol) was added to a DMI (4 ml) suspension of sodium tert-pentoxide (1.67 g, 15.2 mmol) at room temperature in a nitrogen atmosphere, and the mixture was stirred at 40° C. for 2 hours. This reaction solution was cooled in an ice bath, and a DMI (3 ml) solution of compound 2A (1.10 g, 6.68 mmol) was added dropwise thereto at 0-10° C. The reaction solution was stirred at 0-5° C. for 2 hours and at room temperature for 3 hours, and 2 N hydrochloric acid (15 ml) was then added thereto, followed by extraction two times with ethyl acetate. The combined extracts were washed with water, a saturated aqueous solution of sodium bicarbonate, water, and saturated saline in this order and then dried over anhydrous sodium sulfate. The solvent was distilled off, and the obtained oil was purified by silica gel column chromatography (n-hexane-ethyl acetate: 4:1, v/v) to obtain 1.29 g (yield: 90%) of compound 2B as an oil.

$^1$H-NMR (CDCl$_3$) δ: 1.25 (3H, t, J=7.2 Hz), 3.54 (2H, s), 4.14 (2H, s), 4.17 (2H, q, J=7.2 Hz), 4.59 (2H, s), 7.28-7.40 (5H, m).

Step 2

Compound 2B (9.73 g, 41.2 mmol) was dissolved in toluene (45 mL). To the solution, N,N-dimethylformamide dimethyl acetal (7.36 g, 61.8 mmol) was added, and the mixture was stirred at room temperature for 5 hours. Water was added to the reaction solution, followed by extraction two times with ethyl acetate. The combined extracts were washed with water and saturated saline in this order and then dried over anhydrous magnesium sulfate. The solvent was distilled off, and the obtained oil was purified by silica gel column chromatography (n-hexane-ethyl acetate: 1:1→3:7, v/v) to obtain 7.90 g (yield: 66%) of compound 2C as an oil.

¹H-NMR (CDCl₃) δ: 1.25 (3H, t, J=7.2 Hz), 2.95 (3H, br), 3.22 (3H, br), 4.15 (2H, q, J=7.2 Hz), 4.45 (2H, s), 4.59 (2H, s), 7.22-7.40 (5H, m), 7.73 (1H, s).

Step 3

Sodium tert-butoxide (495 mg, 5.15 mmol) and DMI (2 ml) were added to a three-neck flask in a nitrogen atmosphere, and a DMI (3 ml) solution of dimethyl oxalate (608 mg, 5.15 mmol) and compound 2C (0.50 g, 1.72 mmol) was added dropwise thereto at 25-30° C. After stirring at room temperature for 4 hours, 2 N hydrochloric acid (10 ml) was added, and the mixture was stirred at room temperature for 15 hours. After extraction two times with toluene, the combined extracts were washed with water, a saturated aqueous solution of sodium bicarbonate, water, and saturated saline in this order and then dried over anhydrous sodium sulfate. The solvent was distilled off, and the obtained residue was purified by silica gel column chromatography (n-hexane-ethyl acetate: 2:1, v/v) to obtain 420 mg (yield: 74%) of compound 2D as white crystals.

¹H-NMR (CDCl₃) δ: 1.39 (3H, t, J=7.2 Hz), 3.88 (3H, s), 4.39 (2H, q, J=7.2 Hz), 5.34 (2H, s), 7.30-7.41 (3H, m), 7.45-7.50 (2H, m), 8.48 (1H, s).

Example 3

[Chemical Formula 131]

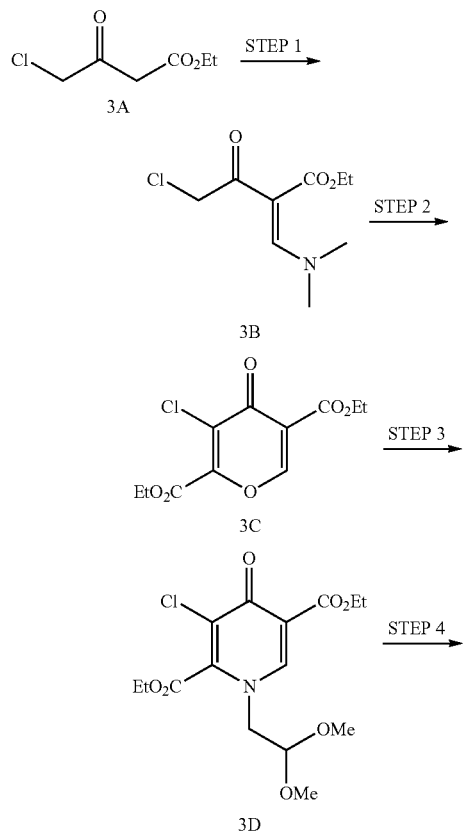

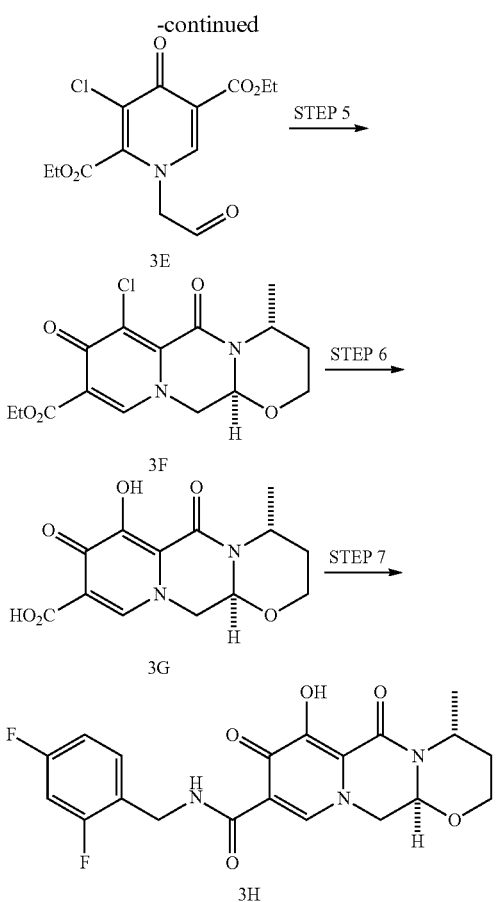

Step 1

N,N-dimethylformamide dimethyl acetal (4.9 ml, 36.5 mmol) was added dropwise to compound 3A (5.0 g, 30.4 mmol) under cooling at 0° C. After stirring at 0° C. for 1 hour, 100 ml of ethyl acetate was added to the reaction solution, and the organic layer was washed with a 0.5 N aqueous hydrochloric acid solution (50 ml). The aqueous layer was separated, followed by extraction with ethyl acetate (50 ml). The organic layers were combined, washed with a saturated aqueous solution of sodium bicarbonate and saturated saline in this order, and then dried over anhydrous sodium sulfate. The solvent was distilled off, and the obtained residue was purified by silica gel column chromatography (n-hexane-ethyl acetate: 1:1 (v/v)→ethyl acetate) to obtain 4.49 g (yield: 67%) of compound 3B as an oil.

¹H-NMR (CDCl₃) δ:1.32 (3H, t, J=7.1 Hz), 2.90 (3H, br s), 3.29 (3H, br s), 4.23 (2H, q, J=7.1 Hz), 4.54 (2H, s), 7.81 (1H, s).

Step 2

Lithium hexamethyldisilazide (1.0 M solution in toluene, 49 ml, 49.0 mmol) was diluted with tetrahydrofuran (44 ml). A tetrahydrofuran (10 ml) solution of compound 3B (4.49 g, 20.4 mmol) was added dropwise thereto under cooling at −78° C., and a tetrahydrofuran (10 ml) solution of ethyl oxalyl chloride (3.35 g, 24.5 mmol) was then added dropwise to the mixture. The mixture was stirred at −78° C. for 2 hours and then heated to 0° C. 2 N hydrochloric acid was added to the reaction solution, and the mixture was stirred for 20 minutes, followed by extraction with ethyl acetate (200 ml×2). The organic layer was washed with a saturated aqueous solution of sodium bicarbonate and saturated saline and then dried over anhydrous sodium sulfate. The solvent was distilled off, and the obtained residue was purified by silica gel column chromatography (n-hexane-ethyl acetate: 7:3→5:5→0:10 (v/v)) to obtain 1.77 g (yield: 31%) of compound 3C as a white solid.

$^1$H-NMR (CDCl$_3$) δ:1.36-1.46 (6H, m), 4.35-4.52 (8H, m), 8.53 (1H, s).

Step 3

Aminoacetaldehyde dimethyl acetal (0.13 ml, 1.20 mmol) was added to an ethanol (6 ml) solution of compound 3C (300 mg, 1.09 mmol) at 0° C., and the mixture was stirred at 0° C. for 1.5 hours, then at room temperature for 18 hours, and at 60° C. for 4 hours. The solvent in the reaction solution was distilled off under reduced pressure, and the obtained residue was then purified by silica gel column chromatography (n-hexane-ethyl acetate: 5:5→0:10 (v/v)) to obtain 252 mg (yield: 64%) of compound 3D as an oil.

$^1$H-NMR (CDCl$_3$) δ:1.36-1.47 (6H, m), 3.42 (6H, s), 3.90 (2H, d, J=5.2 Hz), 4.37 (3H, q, J=7.2 Hz), 4.50 (2H, q, J=7.2 Hz), 8.16 (1H, s).

Step 4

62% H$_2$SO$_4$ (892 mg, 5.64 mmol) was added to a formic acid (10 ml) solution of compound 3D (1.02 g, 2.82 mmol), and the mixture was stirred at room temperature for 16 hours. The formic acid was distilled off under reduced pressure. To the residue, methylene chloride was added, and the mixture was pH-adjusted to 6.6 by the addition of a saturated aqueous solution of sodium bicarbonate. The methylene chloride layer was separated, while the aqueous layer was subjected to extraction with methylene chloride. The methylene chloride layers were combined and dried over anhydrous sodium sulfate. The solvent was distilled off to obtain 531.8 mg of compound 3E as a yellow oil.

1H-NMR (CDCl$_3$) δ: 1.28-1.49 (6H, m), 4.27-4.56 (4H, m), 4.84 (2H, s), 8.10 (1H, s), 9.72 (1H, s).

Step 5

Methanol (0.20 ml, 5.0 mmol), (R)-3-amino-butan-1-ol (179 mg, 2.0 mmol), and acetic acid (0.096 ml, 1.70 mmol) were added to a toluene (5 ml) solution of compound 3E (531 mg, 1.68 mmol), and the mixture was heated to reflux for 4 hours. The reaction solution was cooled to room temperature, then diluted with chloroform, and then washed with a saturated aqueous solution of sodium bicarbonate. The aqueous layer was subjected to extraction with chloroform. The chloroform layers were combined, washed with saturated saline, and then dried over anhydrous sodium sulfate. The solvent was distilled off, and the obtained residue was purified by silica gel column chromatography (chloroform-methanol: 100:0→90:10) to obtain 309.4 mg of compound 3F as a brown oil.

1H-NMR (CDCl3) δ: 1.40 (3H, t, J=7.1 Hz), 1.40 (3H, d, J=7.1 Hz), 1.55-1.61 (1H, m), 2.19-2.27 (1H, m), 4.00 (1H, d, J=1.5 Hz), 4.03 (1H, d, J=2.5 Hz), 4.10 (1H, dd, J=13.2, 6.3 Hz), 4.26 (1H, dd, J=13.2, 3.8 Hz), 4.38 (2H, q, J=7.1 Hz), 5.00-5.05 (1H, m), 5.31 (1H, dd, J=6.4, 3.9 Hz), 8.10 (1H, s).

Step 6

Potassium trimethylsilanolate (333 mg, 2.34 mmol) was added to a 1,2-dimethoxyethane (2 ml) solution of compound 3F (159 mg, 0.47 mmol), and the mixture was stirred at room temperature for 7 hours. 1 N hydrochloric acid and saturated saline were added to the reaction solution, followed by extraction with chloroform. The chloroform layers were combined and dried over anhydrous sodium sulfate. The solvent was distilled off to obtain 34.4 mg (yield: 25%) of compound 3G as an orange powder.

1H-NMR (CDCl3) δ: 1.46 (3H, d, J=3.5 Hz), 1.58-1.65 (1H, m), 2.26-2.30 (1H, m), 4.06-4.10 (2H, m), 4.31 (1H, dd, J=13.8, 5.6 Hz), 4.48 (1H, dd, J=13.6, 3.9 Hz), 5.03 (1H, t, J=6.4 Hz), 5.36 (1H, dd, J=5.5, 4.0 Hz), 8.44 (1H, s), 12.80 (1H, s), 14.90 (1H, s).

Step 7

Compound 3G (16 mg, 0.054 mmol) and 2,4-difluorobenzylamine (17 mg, 0.12 mmol) were dissolved in N,N-dimethylformamide (1 ml). To the solution, N,N,N',N'-tetramethyl-O-(7-aza-benzotriazol-1-yl)uronium hexafluorophosphate (HATU) (53 mg, 0.14 mmol) and N-methylmorpholine (0.031 ml, 0.28 mmol) were added, and the mixture was stirred at room temperature for 16 hours. 2,4-difluorobenzylamine (17 mg, 0.12 mmol), HATU (64 mg, 0.17 mmol), and N-methylmorpholine (0.037 ml, 0.34 mmol) were further added thereto, and the mixture was stirred at room temperature for additional 16 hours. 0.5 N hydrochloric acid was added to the reaction solution, followed by extraction with ethyl acetate. The ethyl acetate layers were combined, washed with 0.5 N hydrochloric acid and then with saturated saline, and then dried over anhydrous sodium sulfate. The solvent was distilled off, and the obtained residue was purified by preparative high-performance liquid chromatography to obtain 12.5 mg (yield: 55%) of compound 3H as an orange solid.

1H-NMR (DMSO-d6) δ: 1.36 (3H, d, J=6.9 Hz), 1.55-1.60 (1H, m), 2.01-2.05 (1H, m), 3.92-3.94 (1H, m), 4.04 (1H, t, J=12.6 Hz), 4.38-4.41 (1H, m), 4.57-4.60 (1H, m), 4.81-4.83 (1H, m), 5.46-5.49 (1H, m), 7.08-7.11 (1H, m), 7.25-7.30 (1H, m), 7.41 (1H, dd, J=15.3, 8.7 Hz), 8.53 (1H, s), 10.38 (1H, s), 12.53 (1H, s).

Example 4

[Chemical Formula 132]

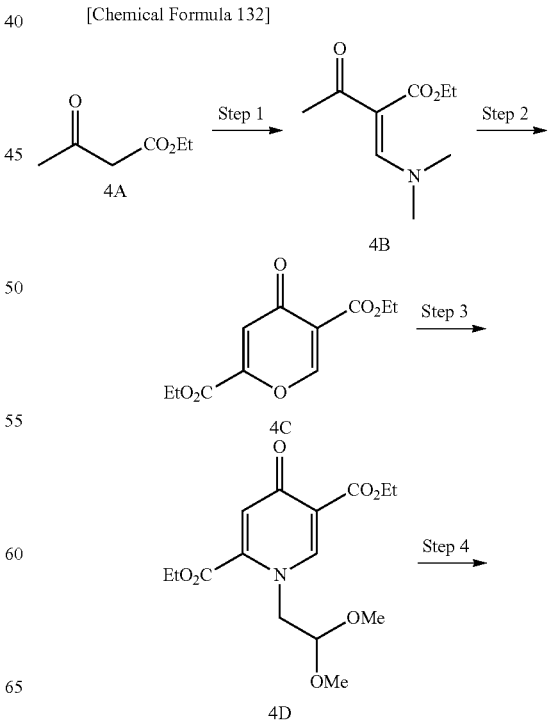

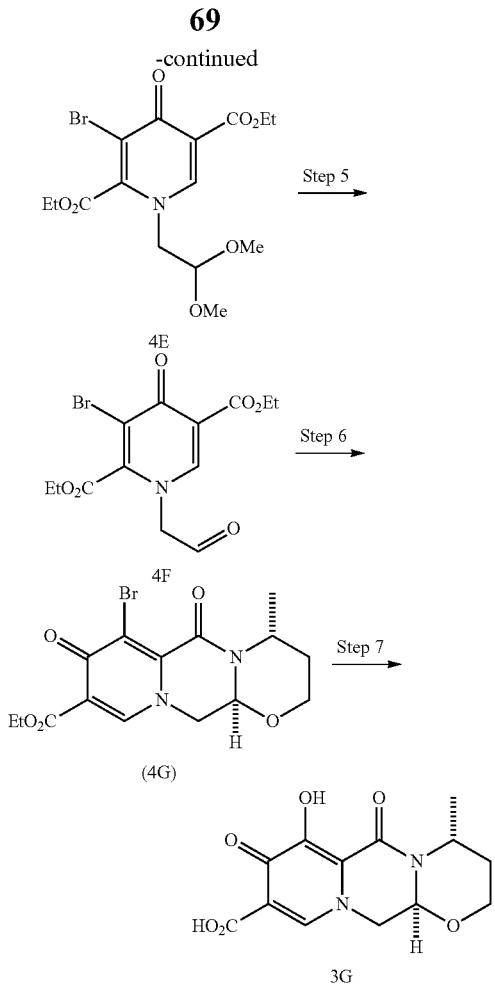

Step 1

N,N-dimethylformamide dimethyl acetal (12.2 ml, 92.2 mmol) was added dropwise to compound 4A (10.0 g, 76.8 mmol) under cooling at 0° C. After stirring at 0° C. for 1.5 hours and then at room temperature for 2.5 hours, 100 ml of ethyl acetate was added to the reaction solution, and the solvent was distilled off. The obtained residue was purified by silica gel column chromatography (n-hexane-ethyl acetate: 5:5→0:10 (v/v)) to obtain 12.45 g (yield: 88%) of compound 4B as an oil.

$^1$H-NMR (CDCl$_3$) δ:1.32 (3H, t, J=7.1 Hz), 2.33 (3H, s), 3.04 (6H, br s), 4.23 (2H, q, J=7.2 Hz), 7.68 (1H, s).

Step 2

Lithium hexamethyldisilazide (1.0 M solution in toluene, 24 ml, 24.0 mmol) was diluted with tetrahydrofuran (20 ml). A tetrahydrofuran (5 ml) solution of compound 4B (1.85 g, 10.0 mmol) was added dropwise thereto under cooling at −78° C., and a tetrahydrofuran (5 ml) solution of ethyl oxalyl chloride (1.34 ml, 12.0 mmol) was then added dropwise thereto. After stirring at −78° C. for 2 hours, 2 N hydrochloric acid was added to the reaction solution, and the mixture was stirred at room temperature for 20 minutes. After extraction with ethyl acetate, the organic layer was washed with a saturated aqueous solution of sodium bicarbonate and saturated saline in this order and then dried over anhydrous sodium sulfate. The solvent was distilled off, and the obtained residue was purified by silica gel column chromatography (n-hexane-ethyl acetate: 75:25→455:5 (v/v)) to obtain 1.03 g (yield: 43%) of compound 4C as a brown oil.

$^1$H-NMR (CDCl$_3$) δ:1.38 (3H, t, J=7.1 Hz), 1.42 (3H, t, J=7.4 Hz), 4.33-4.47 (4H, m), 7.19 (1H, s), 8.54 (1H, s).

Step 3

Aminoacetaldehyde dimethyl acetal (0.34 ml, 3.11 mmol) was added to an ethanol (6.8 ml) solution of compound 4C (680 mg, 2.83 mmol) at 0° C., and the mixture was left standing at room temperature for 16 hours. The solvent in the reaction solution was distilled off under reduced pressure, and the obtained residue was then purified by silica gel column chromatography (n-hexane-ethyl acetate: 90:10 (v/v)) to obtain 875 mg (yield: 94%) of compound 4D as an oil.

$^1$H-NMR (CDCl$_3$) δ:1.38 (3H, t, J=7.1 Hz), 1.39 (3H, t, J=7.1 Hz), 3.40 (6H, s), 4.33 (2H, d, J=4.7 Hz), 4.37 (4H, q, J=7.1 Hz), 4.49 (1H, t, J=4.7 Hz), 7.06 (1H, s), 8.17 (1H, s).

Step 4

N-bromosuccinimide (1.46 g, 8.18 mmol) was added to a N,N-dimethylformamide (10 ml) solution of compound 4D (2.68 g, 8.18 mmol), and the mixture was stirred at room temperature for 48 hours. A saturated aqueous solution of sodium bicarbonate was added to the reaction solution, followed by extraction with ethyl acetate. The organic layer was washed with water and saturated saline in this order and then dried over anhydrous sodium sulfate. The solvent was distilled off, and the obtained residue was then purified by silica gel column chromatography (n-hexane-ethyl acetate: 90:10 (v/v)) to obtain 2.83 g (yield: 85%) of compound 4E as an oil.

1H-NMR (CDCl3) δ: 1.41 (3H, t, J=7.1 Hz), 1.48 (3H, t, J=7.1 Hz), 3.42 (6H, s), 3.90 (2H, d, J=5.0 Hz), 4.39 (2H, q, J=7.1 Hz), 4.53 (3H, q, J=14.3 Hz), 4.54 (3H, s), 4.57 (3H, t, J=5.4 Hz), 8.19 (1H, s).

Step 5

62% H$_2$SO$_4$ (1.74 g, 10.98 mmol) was added to a formic acid (15 ml) solution of compound 4E (2.23 g, 5.49 mmol), and the mixture was stirred at room temperature for 8 hours. A 0.5 N aqueous sodium hydroxide solution (120 ml) was added thereto, followed by extraction with methylene chloride. The methylene chloride layers were combined, washed with saturated saline, and then dried over anhydrous sodium sulfate. The solvent was distilled off to obtain 1.31 g of compound 4F as a white powder.

1H-NMR (CDCl3) δ: 1.31-1.46 (6H, m), 4.33-4.48 (4H, m), 4.82 (2H, s), 8.11 (1H, s), 9.71 (1H, s).

Step 6

Methanol (0.44 ml, 10.9 mmol), (R)-3-amino-butan-1-ol (389 mg, 4.36 mmol), and acetic acid (0.21 ml, 3.64 mmol) were added to a toluene (13 ml) solution of compound 4F (1.31 g, 3.64 mmol), and the mixture was heated to reflux for 3 hours. The reaction solution was cooled to room temperature, then diluted with chloroform, and then washed with a saturated aqueous solution of sodium bicarbonate. The aqueous layer was subjected to extraction with chloroform. The chloroform layers were combined, washed with saturated saline, and then dried over anhydrous sodium sulfate. The solvent was distilled off, and the obtained residue was purified by silica gel column chromatography (chloroform-methanol: 100:0→90:10) to obtain 1.58 g of compound 4G as an oil.

1H-NMR (CDCl3) δ: 1.40 (3H, d, J=5.7 Hz), 1.56-1.60 (1H, m), 2.19-2.24 (1H, m), 3.99 (1H, d, J=2.0 Hz), 4.02 (1H, d, J=2.4 Hz), 4.11 (1H, dd, J=13.3, 6.7 Hz), 4.28 (1H, dd, J=13.3, 3.9 Hz), 4.36 (3H, q, J=7.1 Hz), 4.49-4.56 (1H, m), 4.98-5.03 (1H, m), 5.34 (1H, dd, J=6.6, 3.8 Hz), 8.07 (1H, s).

Step 7

Potassium trimethylsilanolate (249 mg, 1.95 mmol) was added to a 1,2-dimethoxyethane (3 ml) solution of compound 4G (300 mg, 0.78 mmol), and the mixture was stirred at room temperature for 1 hour. Potassium trimethylsilanolate (249 mg, 1.95 mmol) was further added thereto, and the mixture was stirred at 60° C. for additional 1 hour. 1 N hydrochloric acid and saturated saline were added to the reaction solution, followed by extraction with chloroform. The chloroform layers were combined and dried over anhydrous sodium sulfate. The solvent was distilled off to obtain 100.3 mg (yield: 43%) of compound 3G as a yellow powder.

1H-NMR (CDCl3) δ: 1.46 (3H, d, J=3.5 Hz), 1.58-1.65 (1H, m), 2.26-2.30 (1H, m), 4.06-4.10 (2H, m), 4.31 (1H, dd, J=13.8, 5.6 Hz), 4.48 (1H, dd, J=13.6, 3.9 Hz), 5.03 (1H, t, J=6.4 Hz), 5.36 (1H, dd, J=5.5, 4.0 Hz), 8.44 (1H, s), 12.80 (1H, s), 14.90 (1H, s).

Example 5

[Chemical Formula 133]

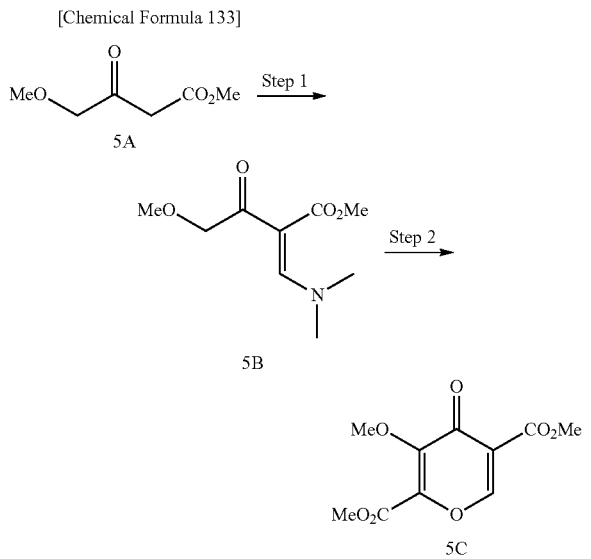

Step 1

Compound 5A (598 mg, 4.09 mmol) and N,N-dimethylformamide dimethyl acetal (488 mg, 4.09 mmol) were dissolved in toluene (1 ml), and the solution was stirred at room temperature for 11 hours. The solvent in the reaction solution was distilled off under reduced pressure, and the obtained residue (containing compound 5B) was used in Step 2 without being purified.

Step 2

Sodium tert-butoxide (400 mg, 4.16 mmol) was suspended in dimethylimidazolidinone (5 ml). To this suspension, a dimethylimidazolidinone (5 ml) solution of the crude product obtained in Step 1 was added. Then, a THF (10 ml) solution of dimethyl oxalate (983 mg, 8.32 mmol) was added dropwise thereto, and the mixture was stirred at room temperature for 45 minutes. The reaction solution was added to 2 N hydrochloric acid-methanol (20 ml), and the mixture was stirred at 0° C. for 20 minutes. Water was added thereto, followed by extraction with ethyl acetate. The organic layer was washed with water, a saturated aqueous solution of sodium bicarbonate, and saturated saline in this order and dried over anhydrous sodium sulfate. The solvent was distilled off, and the obtained residue was then purified by silica gel column chromatography to obtain 222 mg (yield based on compound 5A: 22%) of compound 5C.

1H-NMR (CDCl3) δ:3.91 (3H, s), 3.97 (3H, s), 4.05 (3H, s), 8.50 (1H, s).

Example 6

[Chemical Formula 134]

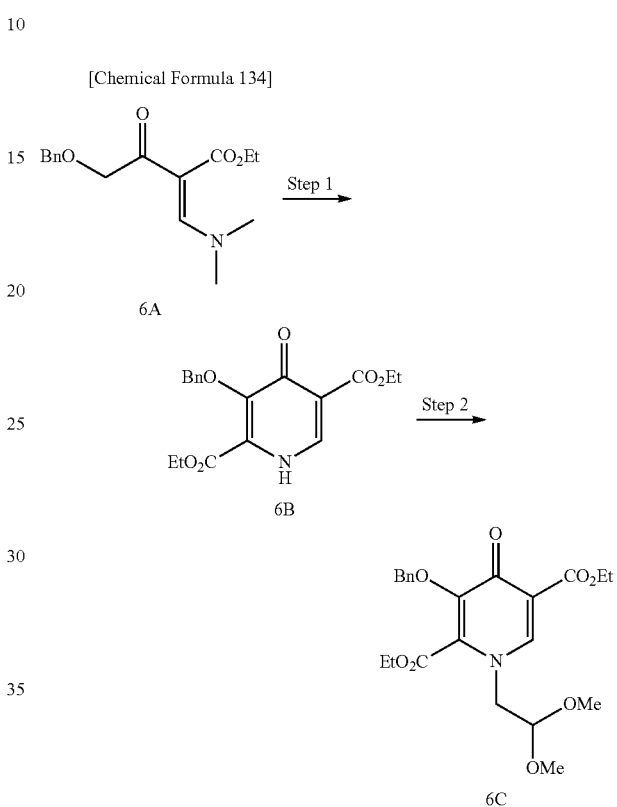

Step 1

Lithium hexamethyldisilazide (1.0 M solution in toluene, 12 ml, 12.0 mmol) was diluted with tetrahydrofuran (11 ml). A tetrahydrofuran (2 ml) solution of compound 6A (1.46 g, 5.0 mmol) was added dropwise thereto under cooling at −78° C., and a tetrahydrofuran (2 ml) solution of ethyl oxalyl chloride (0.67 ml, 6.0 mmol) was then added dropwise thereto. After stirring at −78° C. for 2 hours, ammonium acetate (500 mg) and acetic acid (10 ml) were added to the reaction solution, and the mixture was stirred at 65° C. for 1.5 hours. Water was added to the reaction solution, followed by extraction with ethyl acetate. The organic layer was washed with water and a saturated aqueous solution of sodium bicarbonate in this order and then dried over anhydrous sodium sulfate. The solvent was distilled off, and the obtained residue was purified by silica gel column chromatography (n-hexane-ethyl acetate: 55:45→45:55 (v/v)) to obtain 505.1 mg of compound 6B as a yellow solid. This solid was washed with isopropyl ether-hexane (1:2) and dried under reduced pressure to obtain 416.8 mg (yield: 24%) of compound 6B as yellow crystals.

1H-NMR (CDCl3) δ:1.35 (3H, t, J=7.1 Hz), 1.46 (3H, t, J=7.1 Hz), 4.40 (2H, q, J=7.2 Hz), 4.50 (2H, q, J=7.1 Hz), 5.20 (2H, s), 7.33-7.41 (3H, m), 7.49-7.52 (2H, m), 8.76 (1H, s), 11.61 (1H, br s).

Step 2

Cesium carbonate (73.3 mg, 0.23 mmol) and bromoacetaldehyde dimethyl acetal (38.0 mg, 0.23 mmol) were added to a N,N-dimethylformamide (1 ml) solution of compound 6B (51.8 mg, 0.15 mmol), and the mixture was stirred overnight at room temperature. Cesium carbonate (73.3 mg, 0.23 mmol) and bromoacetaldehyde dimethyl acetal (38.0 mg, 0.23 mmol) were further added thereto, and the mixture was stirred at 100° C. for additional 20 minutes. Water was added to the reaction solution, followed by extraction with ethyl acetate. The organic layer was washed with water and saturated saline in this order and then dried over anhydrous sodium sulfate. The solvent was distilled off, and the obtained residue was purified by silica gel column chromatography (n-hexane-ethyl acetate: 50:50→30:70 (v/v)) to obtain 35.3 mg (yield: 54%) of compound 6C as a colorless oil.

$^1$H-NMR (CDCl$_3$) δ:1.26 (3H, t, J=7.1 Hz), 1.40 (3H, t, J=7.1 Hz), 3.39 (6H, s), 3.91 (2H, d, J=5.0 Hz), 4.29 (2H, q, J=7.1 Hz), 4.40 (2H, q, J=7.2 Hz), 4.50 (1H, t, J=5.0 Hz), 5.30 (2H, s), 7.31-7.37 (3H, m), 7.43-7.46 (2H, m), 8.12 (1H, s).

Example 7

[Chemical Formula 135]

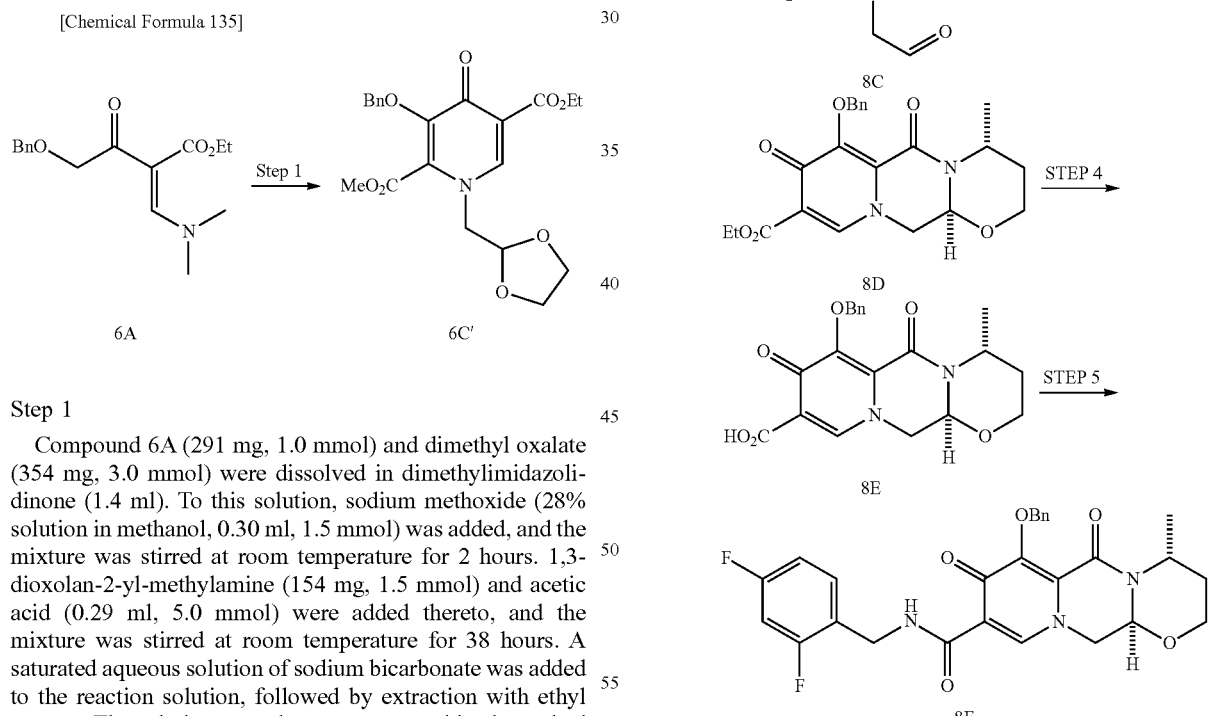

Step 1

Compound 6A (291 mg, 1.0 mmol) and dimethyl oxalate (354 mg, 3.0 mmol) were dissolved in dimethylimidazolidinone (1.4 ml). To this solution, sodium methoxide (28% solution in methanol, 0.30 ml, 1.5 mmol) was added, and the mixture was stirred at room temperature for 2 hours. 1,3-dioxolan-2-yl-methylamine (154 mg, 1.5 mmol) and acetic acid (0.29 ml, 5.0 mmol) were added thereto, and the mixture was stirred at room temperature for 38 hours. A saturated aqueous solution of sodium bicarbonate was added to the reaction solution, followed by extraction with ethyl acetate. The ethyl acetate layers were combined, washed with water and saturated saline in this order, and dried over anhydrous sodium sulfate. The solvent was distilled off, and the obtained residue was purified by silica gel column chromatography (hexane-ethyl acetate: 33:67→15:85) to obtain 294.8 mg (yield: 70%) of compound 6C' as a pale yellow oil.

1H-NMR (CDCl3) δ: 1.43 (3H, t, J=7.1 Hz), 3.73-3.75 (2H, m), 3.81 (3H, s), 3.82-3.85 (2H, m), 4.21 (2H, d, J=2.2 Hz), 4.42 (2H, q, J=7.1 Hz), 5.14 (1H, t, J=2.3 Hz), 5.32 (2H, s), 7.34-7.37 (3H, m), 7.44-7.46 (2H, m), 8.14 (1H, s).

Example 8

[Chemical Formula 136]

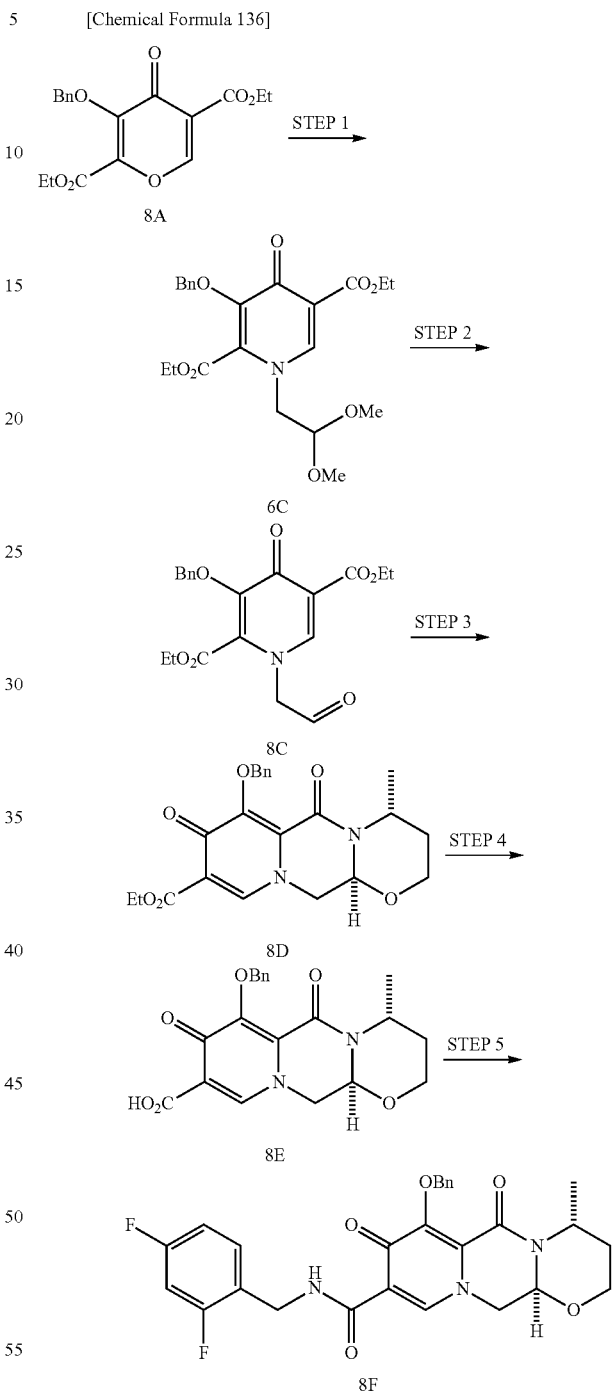

Step 1

Aminoacetaldehyde dimethyl acetal (7.80 mmol) was added to an ethanol (5 ml) solution of compound 8A (900 mg, 2.60 mmol), and the mixture was stirred at room temperature for 22 hours. Ethyl acetate (5 ml) and water (5 ml) were added to the reaction solution, followed by extraction with ethyl acetate (5 ml). The organic layer was washed with water (10 ml). Then, the solvent was distilled off, and the obtained residue was purified by silica gel column chromatography (n-hexane-ethyl acetate: 2:1) to obtain 0.37 g (yield: 33%) of compound 6C as a colorless oil.

$^1$H-NMR (CDCl$_3$) δ: 7.90 (1H, s), 7.45-7.43 (5H, m), 5.30 (2H, s), 4.51 (1H, t, J=5.1 Hz), 4.40 (2H, q, J=7.1 Hz), 4.30 (2H, q, J=7.1 Hz), 3.91 (2H, d, J=5.1 Hz), 3.46 (6H, s), 1.40 (3H, t, J=7.1 Hz), 1.26 (3H, t, J=7.1 Hz).

Step 2

62% H$_2$SO$_4$ (316 mg, 2.0 mmol) was added to a formic acid (4 ml) solution of compound 6C (433.5 mg, 1.0 mmol), and the mixture was stirred at room temperature for 3 hours. Methylene chloride was added to the reaction solution, and the organic layer was washed with a 0.5 N aqueous sodium hydroxide solution (12 ml). The aqueous layer was subjected to extraction with methylene chloride. The methylene chloride layers were combined, washed with saturated saline, and then dried over anhydrous sodium sulfate. The solvent was distilled off to obtain 207.6 mg (yield: 51%) of compound 8C as a yellow foam.

1H-NMR (CDCl3) δ: 1.23 (3H, t, J=7.1 Hz), 1.42 (3H, t, J=7.1 Hz), 4.25 (2H, q, J=7.2 Hz), 4.42 (2H, q, J=7.1 Hz), 4.79 (2H, s), 5.34 (2H, s), 7.31-7.53 (5H, m), 8.05 (1H, s), 9.67 (1H, s).

Step 3

Methanol (0.061 ml, 1.5 mmol), (R)-3-amino-butan-1-ol (53.5 mg, 0.60 mmol), and acetic acid (0.029 ml, 0.50 mmol) were added to a toluene (2 ml) solution of compound 8C (202.6 mg, 0.50 mmol), and the mixture was heated to reflux for 3 hours. The reaction solution was cooled to room temperature. Then, methylene chloride was added thereto, and the organic layer was washed with a saturated aqueous solution of sodium bicarbonate. The aqueous layer was subjected to extraction with methylene chloride. The methylene chloride layers were combined, washed with saturated saline, and then dried over anhydrous sodium sulfate. The solvent was distilled off, and the obtained residue was purified by silica gel column chromatography (chloroform-methanol: 100:0→91:9) to obtain 161.6 mg (yield: 78%) of compound 8D as a yellow foam.

1H-NMR (CDCl3) δ: 1.34 (3H, d, J=7.1 Hz), 1.41 (3H, t, J=7.1 Hz), 1.49-1.54 (1H, m), 2.14-2.20 (1H, m), 3.96-3.97 (2H, m), 4.03 (3H, dd, J=13.3, 5.9 Hz), 4.17 (3H, dd, J=13.3, 3.7 Hz), 4.41 (3H, q, J=7.1 Hz), 5.01 (1H, t, J=5.6 Hz), 5.17 (1H, dd, J=5.9, 3.9 Hz), 5.33 (2H, d, J=10.1 Hz), 5.39 (2H, d, J=9.9 Hz), 7.33-7.36 (3H, m), 7.68-7.70 (2H, m), 8.05 (1H, s).

Step 4

Compound 8D (50 mg, 0.12 mmol) was dissolved in tetrahydrofuran-methanol (0.5 ml and 0.5 ml, respectively). To this solution, a 1 N aqueous sodium hydroxide solution (0.36 ml, 0.36 mmol) was added, and the mixture was stirred at room temperature for 2 hours. The reaction solution was pH-adjusted to 2.5 by the addition of 1 N hydrochloric acid and subjected to extraction with chloroform. The chloroform layers were combined, washed with saturated saline, and then dried over anhydrous sodium sulfate. The solvent was distilled off to obtain 46.2 mg (yield: 99%) of compound 8E as a pale yellow foam.

1H-NMR (CDCl3) δ: 1.38 (3H, d, J=7.1 Hz), 1.53-1.56 (1H, m), 2.16-2.18 (1H, m), 3.98-3.99 (2H, m), 4.17 (1H, dd, J=13.3, 5.9 Hz), 4.29 (1H, dd, J=13.4, 3.5 Hz), 5.02 (1H, t, J=6.6 Hz), 5.21 (1H, dd, J=5.5, 3.9 Hz), 5.40 (1H, d, J=10.2 Hz), 5.45 (1H, d, J=10.1 Hz), 7.34-7.39 (3H, m), 7.60-7.62 (2H, m), 8.33 (1H, s), 15.02 (1H, s).

Step 5

Compound 8E (50 mg, 0.13 mmol) and 2,4-difluorobenzylamine (20.5 mg, 0.14 mmol) were dissolved in N,N-dimethylformamide (1 ml). To the solution, N,N,N',N'-tetramethyl-O-(7-aza-benzotriazol-1-yl)uronium hexafluorophosphate (HATU) (64 mg, 0.17 mmol) and N-methylmorpholine (0.037 ml, 0.34 mmol) were added, and the mixture was stirred at room temperature for 16 hours. HATU (64 mg, 0.17 mmol) and N-methylmorpholine (0.037 ml, 0.34 mmol) were further added thereto, and the mixture was stirred at room temperature for additional 16 hours. Water was added to the reaction solution, followed by extraction with ethyl acetate. The ethyl acetate layers were combined, washed with saturated saline, and then dried over anhydrous sodium sulfate. The solvent was distilled off, and the obtained residue was purified by silica gel column chromatography (chloroform-methanol: 100:0→95:5) to obtain 48.4 mg (yield: 73%) of compound 8F as a yellow oil.

1H-NMR (CDCl3) δ: 1.36 (4H, d, J=7.1 Hz), 1.50-1.55 (1H, m), 2.16-2.18 (1H, m), 3.98-3.99 (2H, m), 4.11 (1H, dd, J=13.4, 6.0 Hz), 4.24 (1H, dd, J=13.5, 3.9 Hz), 4.66 (2H, d, J=5.9 Hz), 5.01-5.04 (1H, m), 5.19 (1H, dd, J=6.0, 3.9 Hz), 5.29 (1H, d, J=10.2 Hz), 5.33 (1H, d, J=9.9 Hz), 6.79-6.87 (2H, m), 7.31-7.43 (4H, m), 7.63-7.65 (2H, m), 8.36 (1H, s), 10.42 (1H, s).

Example 9

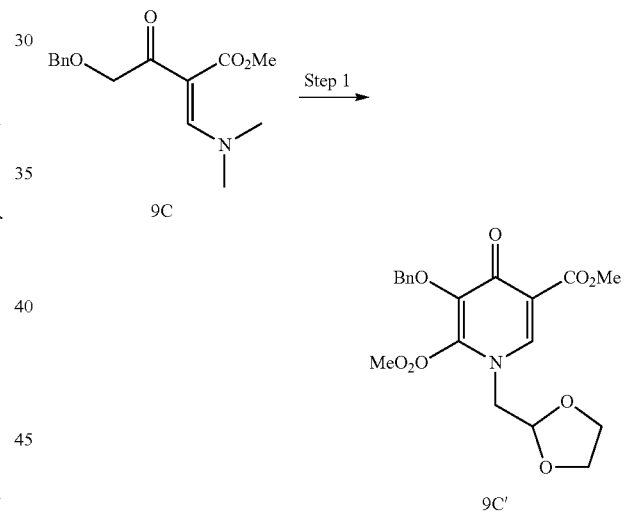

Step 1

In a two-neck flask, compound 9C (291.3 mg, 10 mmol) was dissolved in DMI (1.4 mL) in a nitrogen atmosphere. To the solution, dimethyl oxalate (354.3 mg, 3.0 mmol) and sodium methoxide (28% solution in methanol 0.3 mL, 1.5 mmol) was added, and the mixture was stirred at room temperature for 2 hours. 2-(aminomethyl)-1,3-dioxane (154.7 mg, 1.5 mmol) and acetic acid (0.29 mL, 5.0 mmol) were added thereto, and the mixture was stirred at room temperature for 5 hours. Ethyl acetate (50 mL) was added to the reaction solution, and the organic layer was washed with water (20 mL), a 10% aqueous ammonium chloride solution (20 mL), water (20 mL), and saturated saline (20 mL) in this order and dried over anhydrous magnesium sulfate. The solvent was distilled off, and the obtained residue was purified by silica gel column chromatography (n-hexane-ethyl acetate: 1:1→1:3, v/v) to obtain 99.0 mg (yield: 25%) of compound 9C' as white crystals.

¹H-NMR (CDCl₃) δ: 8.14 (1H, s), 7.44-7.42 (5H, m), 5.29 (2H, s), 5.12 (1H, s), 4.19 (2H, s), 3.93 (3H, s), 3.83-3.70 (2H, m), 3.83 (2H, s).

Example 10

[Chemical Formula 138]

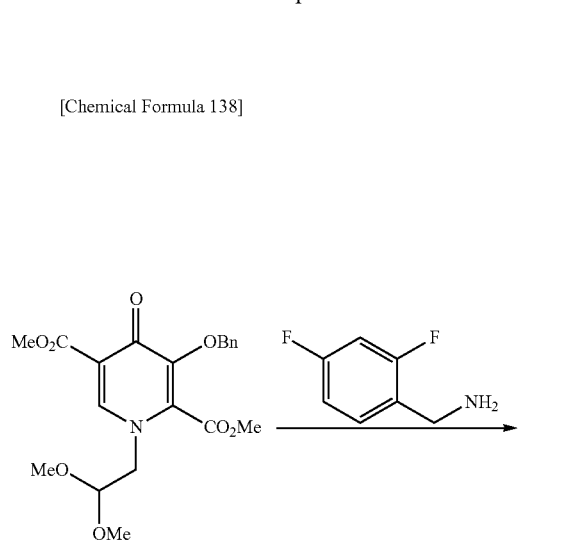

Step 1

Compound 10A (944 mg, 2.33 mmol) was mixed with 2,4-difluorobenzyl amine (401 mg, 2.80 mmol). To the mixture, methanol (2 mL) was added, and the mixture was stirred at 60° C. for 1 hour and then at 95° C. for 1.5 hours. 2,4-difluorobenzyl amine (401 mg, 2.80 mmol) was further added thereto, and the mixture was stirred at 95° C. for additional 3 hours. A 10% aqueous citric acid solution was added to the reaction solution, followed by extraction with ethyl acetate. The organic layer was washed with water and saturated saline and dried over anhydrous magnesium sulfate. The solvent was distilled off, and the obtained residue was then purified by silica gel column chromatography to obtain 310 mg (yield: 25%) of compound 10B.

¹H-NMR (CDCl₃) δ: 3.41 (6H, s), 3.82 (3H, s), 4.04 (2H, d, J=4.9 Hz), 4.49 (1H, t, J=4.9 Hz), 4.67 (2H, d, J=5.9 Hz), 5.28 (2H, s), 6.79-6.89 (2H, m), 7.29-7.46 (5H, m), 8.44 (1H, s), 10.45 (1H, t, J=5.5 Hz).

The acetal moiety of the compound 10B obtained in Example 10 is converted to an aldehyde group in the same way as in Step 4 of Example 3. The resulting compound is reacted with (R)-3-amino-butan-1-ol or (S)-2-amino-propan-1-ol. The benzyl group, which is an alcohol protective group, can be subjected to deprotection reaction (using, for example, Pd—C/H₂ gas) to induce the compound (Y1) or (Y2) of interest.

Example 11

[Chemical Formula 139]

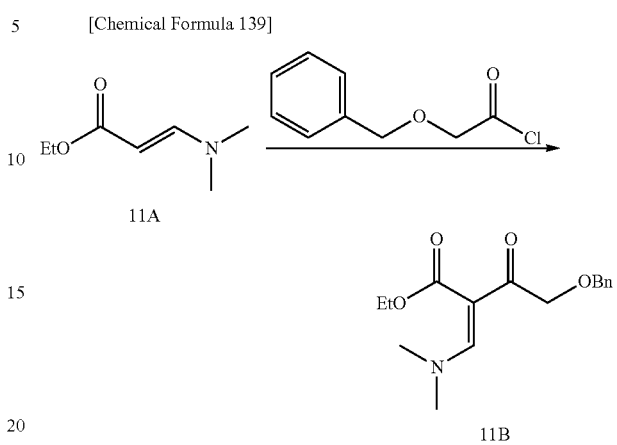

Step 1

A dichloromethane (90 mL) solution of compound 11A (12.8 g, 89.4 mmol) and pyridine (8.50 g, 107 mmol) was cooled to 1-3° C., and a dichloromethane (90 mL) solution of benzyloxy acetyl chloride (19.8 g, 107 mmol) was added dropwise thereto over 50 minutes with the same temperature kept. The reaction solution was stirred at the same temperature for 30 minutes and then gradually heated to 15° C. over 60 minutes, and ice water was added thereto. The dichloromethane layer was separated, while the aqueous layer was subjected to extraction once with dichloromethane. The combined extracts were washed with water three times, and washed with saturated saline, and then dried. The solvent was distilled off, and the obtained oil was subjected to silica gel column chromatography for purification. Elution was performed first with n-hexane and then with n-hexane-ethyl acetate (1:1, v/v). The fraction of interest was concentrated to obtain 22.2 g of compound 11B as an oil.

¹H-NMR (CDCl₃) δ: 1.25 (3H, t, J=7.2 Hz), 2.90 (3H, brs), 3.24 (3H, brs), 4.15 (2H, q, J=7.2 Hz), 4.45 (2H, s), 4.58 (2H, s), 7.25-7.38 (5H, m), 7.72 (1H, s).

The compound 11B obtained in Example 11 can be used in the next reaction in the same way as in Example 6.

Example 12

[Chemical Formula 140]

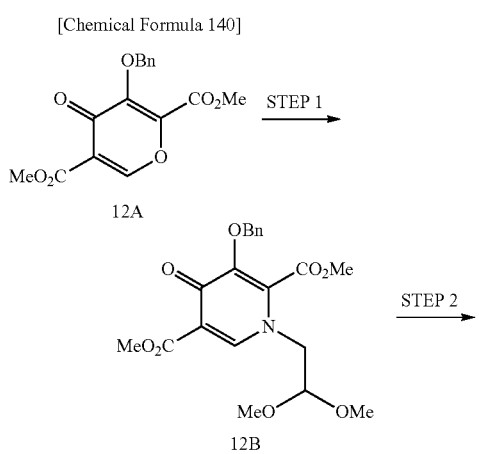

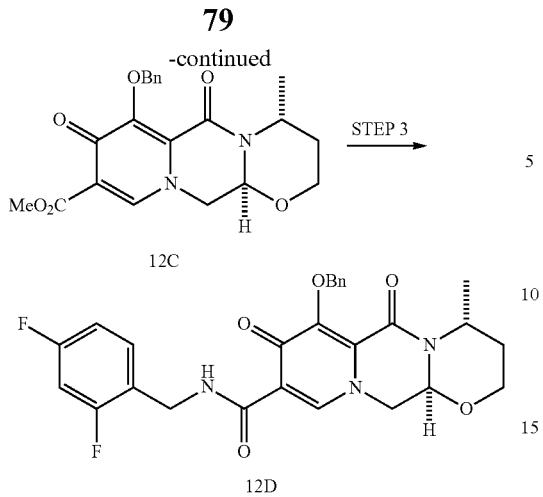

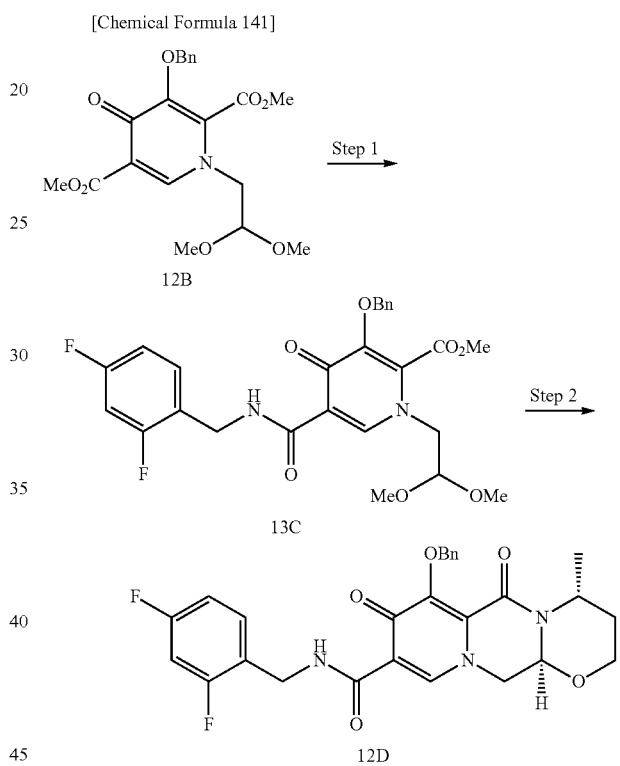

Step 1

Aminoacetaldehyde dimethyl acetal (0.72 g, 6.9 mmol) was added dropwise to a methanol (20 mL) slurry solution of compound 12A (2.0 g, 6.3 mmol) at room temperature, and the mixture was then stirred for 6 hours under heating to reflux. After the completion of reaction, the solvent was distilled off under reduced pressure, and the obtained residue was purified by silica gel chromatography (n-hexane:ethyl acetate=3:17 (v/v)) to obtain 2.26 g (yield: 88%) of compound 12B as a colorless oil.

$^1$H-NMR (CDCl$_3$) δ: 3.38 (6H, s), 3.81 (3H, s), 3.91 (2H, d, J=4.7 Hz), 3.93 (3H, s), 4.47 (1H, t, J=4.7 Hz), 5.29 (2H, s), 7.29-7.37 (3H, m), 7.42-7.44 (2H, m), 8.15 (1H, s).

The compound 12B was dried under conditions of concentration under reduced pressure and left standing at 5° C. for approximately 2 months. In this case, this compound was still in an oil form and was not crystallized. As a result of various studies, however, the compound was successfully crystallized by repeating the addition of ethyl acetate and concentration and isolated as white crystals.

Step 2

A 62% aqueous sulfuric acid solution (307 mg, 1.9 mmol) was added dropwise to a formic acid (3.7 mL) solution of compound 12B (525 mg, 1.3 mmol) at room temperature, and the mixture was stirred at the same temperature for 3 hours. After the completion of reaction, the solution was cooled to 5° C. and neutralized by the addition of a saturated aqueous solution of sodium bicarbonate (24.5 g), followed by extraction with dichloromethane (5 mL×4). The solvent was distilled off under reduced pressure. Then, toluene (5.2 mL) was added to the obtained residue, and methanol (125 mg, 3.9 mmol), (R)-3-amino-butan-1-ol (127 mg, 1.4 mmol), and acetic acid (78 mg, 1.4 mmol) were further added dropwise thereto in this order at room temperature. The mixture was heated to 90° C., stirred for 3 hours, and then allowed to cool to room temperature. Then, water (2 mL) was added thereto, followed by extraction with ethyl acetate (10 mL×2). The solvent was distilled off under reduced pressure, and the obtained residue was purified by silica gel chromatography (chloroform:methanol=97:3 (v/v)) to obtain 418 mg (yield: 81%) of compound 12C as a white foam.

$^1$H-NMR (CDCl$_3$) δ: 1.33 (3H, d, J=7.1 Hz), 1.50 (2H, dd, J=13.9, 2.3 Hz), 2.11-2.20 (1H, m), 3.93 (3H, s), 3.94 (1H, d, J=2.5 Hz), 3.96 (1H, br s), 4.02 (1H, dd, J=13.4, 5.8 Hz), 4.15 (1H, dd, J=13.4, 3.8 Hz), 5.04-4.96 (1H, m), 5.16 (1H, dd, J=6.1, 4.1 Hz), 5.35 (2H, dd, J=22.8, 10.1 Hz), 7.28-7.36 (3H, m), 7.67 (2H, d, J=7.1 Hz), 8.07 (1H, s).

Step 3

2,4-difluorobenzylamine (75 mg, 0.52 mmol) and acetic acid (31 mg, 0.52 mmol) were added dropwise to a toluene (3.4 mL) slurry solution of compound 12C (171 mg, 0.43 mmol) at room temperature, and the mixture was then heated to 100° C. and stirred for 7 hours. After the completion of reaction, the solvent was distilled off under reduced pressure, and the obtained residue was then purified by silica gel chromatography (chloroform:methanol=97:3 (v/v)) to obtain 150 mg (yield: 69%) of compound 12D as yellow crystals.

Example 13

[Chemical Formula 141]

Step 1

2,4-difluorobenzylamine (209 mg, 1.4 mmol) and acetic acid (88 mg, 1.4 mmol) were added to a toluene (5.4 mL) suspension of compound 12B (539 mg, 1.3 mmol) at room temperature, and the mixture was then heated to 90° C. and stirred for 7 hours. After the completion of reaction, the solvent was distilled off under reduced pressure, and the obtained residue was purified by silica gel chromatography (n-hexane:ethyl acetate=3:7 (v/v)) to obtain 666 mg (yield: 97%) of compound 13C as a pale yellow oil.

$^1$H-NMR (CDCl$_3$) δ: 3.37 (6H, s), 3.79 (3H, s), 4.01 (2H, d, J=5.0 Hz), 4.47 (1H, t, J=5.0 Hz), 4.65 (2H, d, J=6.0 Hz), 5.26 (2H, s), 6.78-6.86 (2H, m), 7.30-7.42 (6H, m), 8.42 (1H, s), 10.41 (1H, t, J=6.0 Hz).

Step 2

A 62% aqueous sulfuric acid solution (306 mg, 1.9 mmol) was added to a toluene (2.7 mL)-formic acid (6.7 mL) solution of compound 13C (666 mg, 1.3 mmol) at room temperature, and the mixture was stirred at the same temperature for 3 hours. After the completion of reaction, the solution was cooled to 5° C. and neutralized by the addition of a saturated aqueous solution of sodium bicarbonate (37.0 g), followed by extraction with ethyl acetate (10 mL×2). The solvent was distilled off under reduced pressure. Then, toluene (6.7 mL) was added to the obtained residue, and methanol (124 mg, 3.9 mmol), (R)-3-amino-butan-1-ol (138 mg, 1.6 mmol), and acetic acid (85 mg, 1.4 mmol) were further added dropwise thereto in this order at room temperature. The mixture was heated to 90° C., stirred for 2 hours, and then allowed to cool to room temperature. Then, water (7 mL) was added thereto, followed by extraction with ethyl acetate (10 mL×2). The solvent was distilled off under reduced pressure, and toluene was added to the residue. Then, the solvent was distilled off under reduced pressure to bring the contents to approximately 4.0 g. The residue was concentrated and crystallized. The obtained yellow slurry solution was filtered to obtain 429 mg (yield: 65%) of compound 12D as pale yellow crystals.

Example 14

[Chemical Formula 142]

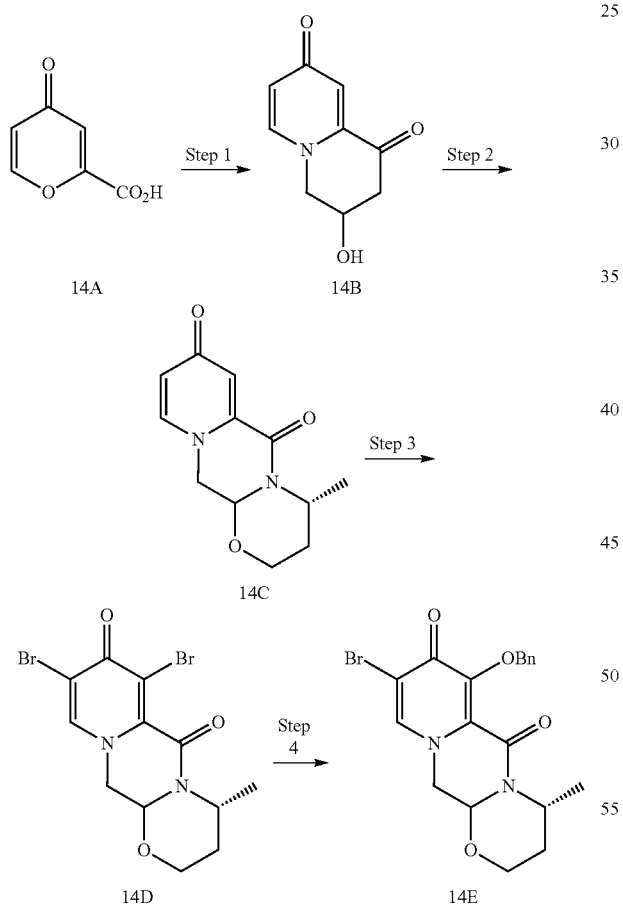

Step 1

Water (2.5 mL) and aminoacetaldehyde dimethyl acetal (756 μL, 7.0 mmol) were added to compound 14A (1.0 g, 7.1 mmol) at room temperature. The mixture was stirred at 65° C. for 1.5 hours and then stirred at 100° C. for 3.5 hours. After concentration to dryness, crystals were deposited by the addition of water (5 mL). 2-propanol (10 mL) was added thereto, followed by filtration. The crystals were washed with 2-propanol (5 mL) and through-flow-dried to obtain 0.98 g (yield: 76%) of crystals of compound 14B.

$^1$H-NMR (CDCl$_3$) δ: 4.56 (2H, d, J=4.9 Hz), 5.38 (1H, t, J=4.9 Hz), 7.16 (1H, dd, J=7.3 Hz, 2.9 Hz), 7.26 (1H, d, J=2.9 Hz), 8.31 (1H, d, J=7.3 Hz).

Step 2

(R)-3-amino-butan-1-ol (75.1 mg, 0.82 mmol) was diluted with 2-propanol (1 mL), and compound 14B (100.6 mg, 0.56 mmol) was added thereto. To the mixture, acetic acid (50 μL) was added, and the mixture was stirred at 80° C. for 16 hours. The solvent was distilled off, and the obtained residue was purified by reverse-phase column chromatography (water-acetonitrile: 95:5→70:30 (v/v)) to obtain 42.0 mg (yield: 32%) of compound 14C as an oil.

$^1$H-NMR (CDCl$_3$) δ: 1.31 (3H, d, J=7.0 Hz), 1.49 (1H, m), 1.96 (1H, m), 3.87 (1H, ddd, J=11.6 Hz, 5.1 Hz, 2.3 Hz), 4.01 (1H, m), 4.12 (1H, dd, J=13.6 Hz, 4.9 Hz), 4.33 (1H, dd, J=13.6 Hz, 4.0 Hz), 4.79 (1H, m), 5.40 (1H, dd, J=4.9 Hz, 4.0 Hz), 6.23 (1H, d, J=7.4 Hz, 2.9 Hz), 6.77 (1H, d, J=2.9 Hz), 7.72 (1H, d, J=7.4 Hz).

Step 3

An acetonitrile (1.5 mL) solution of NBS (191.4 mg, 1.08 mmol) was added dropwise to an acetonitrile (1.5 mL) solution of compound 14C (100.0 mg, 0.43 mmol) at room temperature, and the mixture was stirred at room temperature for 21 hours (including 30 min at 40° C.). Then, NBS (50.1 mg, 0.28 mmol) was further added thereto. After stirring at room temperature for 2 hours, the solvent was distilled off. The obtained residue was purified by reverse-phase column chromatography (water-acetonitrile: 95:5→40:60 (v/v)) to obtain 30.2 mg (yield: 18%) of compound 14D as crystals.

$^1$H-NMR (CDCl$_3$) δ: 1.27 (3H, d, J=7.0 Hz), 1.53 (1H, m), 1.96 (1H, m), 3.87 (1H, m), 3.95 (1H, m), 4.22 (1H, dd, J=13.5 Hz, 6.2 Hz), 4.45 (1H, dd, J=13.5 Hz, 3.8 Hz), 4.74 (1H, m), 5.37 (1H, dd, J=6.2 Hz, 3.8 Hz), 8.50 (1H, s).

Step 4

A 1 mol/L solution of sodium benzyloxide in benzyl alcohol (100 μL, 0.1 mmol) was added to a benzyl alcohol (0.5 mL) solution of compound 14D (5.11 mg, 0.013 mmol) at room temperature, and the mixture was stirred at 90° C. for 50 minutes. The obtained reaction solution was purified by reverse-phase column chromatography (water-acetonitrile: 95:5→40:60 (v/v)) to obtain 2.98 mg (yield: 55%) of compound 14E as crystals.

$^1$H-NMR (CDCl$_3$) δ: 1.27 (3H, d, J=7.0 Hz), 1.59 (1H, m), 1.93 (1H, m), 3.84 (1H, m), 3.96 (1H, m), 4.18 (1H, dd, J=13.5 Hz, 5.5 Hz), 4.39 (1H, dd, J=13.5 Hz, 4.0 Hz), 4.77 (1H, m), 5.04 (2H, s), 5.32 (1H, dd, J=5.5 Hz, 3.5 Hz), 7.31 (1H, m), 7.39 (2H, m), 7.56 (2H, m), 8.38 (1H, s).

Example 15A: Obtainment of Crystals 15A of Anhydride by Crystallization of Compound 12C

[Chemical Formula 143]

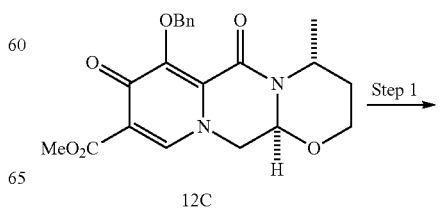

Step 1

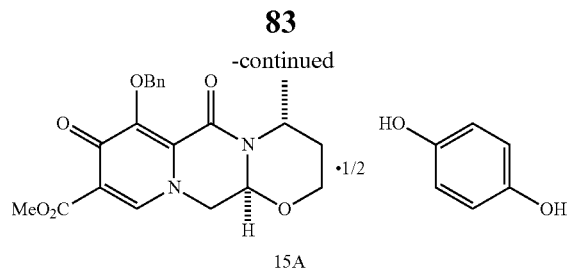

An ethyl acetate (3 mL) solution of hydroquinone (168 mg, 1.52 mmol) was added dropwise to an ethyl acetate (4 mL) solution of compound 12C (1.01 g, 2.53 mmol) at room temperature. After stirring at the same temperature for 1 hour, the obtained slurry solution was filtered to obtain 0.95 g (yield: 81%) of compound 15A as pale yellow crystals. The compound 15A was confirmed to be hydroquinone hemisolvate crystals of compound 12C.

$^1$H-NMR (CDCl$_3$) δ: 1.32 (3H, d, J=7.1 Hz), 1.50 (1H, dd, J=14.2, 2.0 Hz), 2.16 (1H, ddd, J=21.8, 8.1, 5.8 Hz), 3.93 (3H, s), 3.94-3.97 (2H, m), 4.02 (1H, dd, J=13.2, 6.1 Hz), 4.15 (1H, dd, J=13.2, 3.5 Hz), 4.58 (1H, br s), 5.00 (1H, td, J=6.7, 2.2 Hz), 5.16 (1H, dd, J=6.1, 3.5 Hz), 5.34 (2H, dd, J=22.8, 10.1 Hz), 6.72 (1H, s), 7.32 (3H, dt, J=18.9, 5.4 Hz), 7.66 (2H, d, J=7.1 Hz), 8.07 (1H, s).

Example 15B: Obtainment of Crystals 15B of Hydrate by Crystallization of Compound 15A

[Chemical Formula 144]

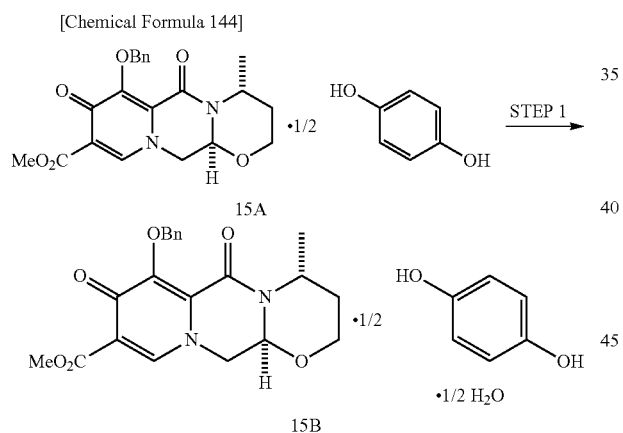

Water (500 µl) was added to compound 15A (50 mg) at room temperature, and the mixture was stirred at the same temperature for 1 hour and then stirred at 70° C. for 2 hours. Then, the obtained slurry solution was filtered to obtain compound 15B as pale yellow crystals. The compound 15B was confirmed to be hemihydrate and hydroquinone hemisolvate crystals of compound 12C.

Example 16

Measurement of Powder X-Ray Diffraction Pattern

The powder X-ray diffractometry of the crystals obtained in each Example was performed under the following measurement conditions according to the powder X-ray diffractometry described in the general test methods of the Japanese Pharmacopoeia.

(Apparatus)
D-8 Discover manufactured by Bruker Corp.
(Operation Procedure)
Each sample was assayed under the following conditions:
Measurement method: Reflection method
Type of light source: Cu tube
Wavelength used: CuKα rays
Tube current: 40 mA
Tube voltage: 40 Kv
Sample plate: glass
X-ray incident angle: 3° and 12°

Methods for producing diastereomers A-5 and B-5 of compound 3H will be shown below in Reference Examples.

Reference Example 1

[Chemical Formula 145]

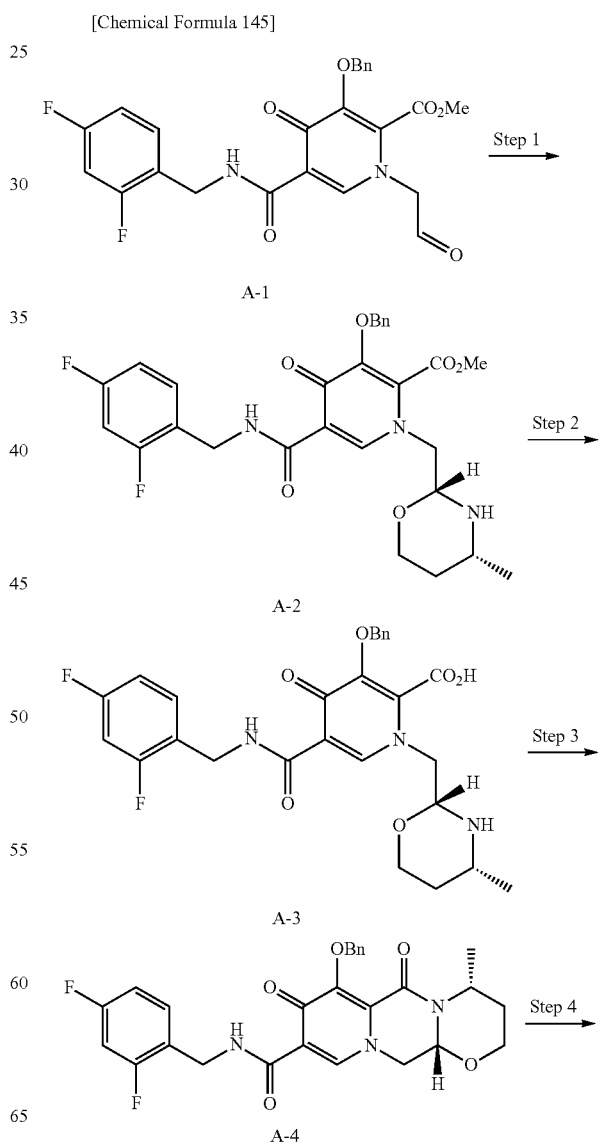

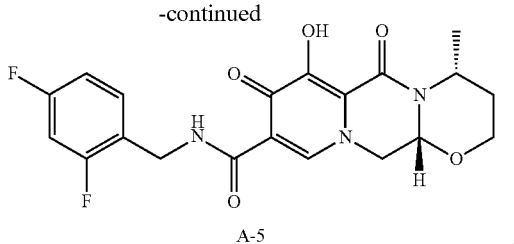

A-5

Step 1

Acetic acid (180 mg, 3.00 mmol) was added to a toluene (90 ml) solution of compound A-1 (4.39 g, 9.33 mmol) and (R)-3-aminobutan-1-ol (998 mg, 11.2 mmol), and the mixture was stirred at 50° C. for 90 minutes. The reaction solution was allowed to cool to room temperature and then poured to a saturated aqueous solution of sodium bicarbonate. The organic layer was separated, while the aqueous layer was subjected to extraction three times with ethyl acetate. The combined extracts were washed with saturated saline and then dried over sodium sulfate. The solvent was distilled off to obtain 4.29 g of crude product A-2.

Step 2

The crude product A-2 obtained in the preceding step was dissolved in ethanol (40 ml). To the solution, a 2 N aqueous sodium hydroxide solution (20 ml) was added at room temperature, and the mixture was stirred at the same temperature for 2 hours. The reaction solution was neutralized to pH 7 using a 2 N aqueous hydrochloric acid solution. The solvent was directly distilled off. The obtained crude product A-3 was subjected to azeotropy with toluene (100 ml) and used in the next step without being purified.

Step 3

HOBt (1.65 g, 12.2 mmol) and WSC HCl (2.34 g, 12.2 mmol) were added at room temperature to a DMF (100 ml) solution of the crude product A-3 obtained in the preceding step, and the mixture was stirred at the same temperature for 15 hours. Water was added to the reaction solution, followed by extraction three times with ethyl acetate. The combined extracts were washed with water three times and then dried over sodium sulfate. The solvent was distilled off, and the obtained oil was subjected to silica gel column chromatography for purification. Elution was performed first with n-hexane-ethyl acetate (3:7, v/v) and then with only ethyl acetate. The fraction of interest was concentrated, and the obtained oil was then dissolved in ethyl acetate. The solution was crystallized with diisopropyl ether as a poor solvent. The obtained crystals were collected by filtration and dissolved again in ethyl acetate. The solution was recrystallized to obtain 1.84 g of compound A-4.

$^1$HNMR (CDCl$_3$) δ: 1.49 (3H, d, J=6.6 Hz), 1.88-1.96 (1H, m), 2.13-2.26 (1H, m), 3.90-4.17 (4H, m), 4.42-4.47 (1H, m), 4.63 (2H, d, J=6.0 Hz), 5.12-5.17 (1H, m), 5.17 (1H, d, J=9.9 Hz), 5.33 (1H, d, J=9.9 Hz), 6.77-6.87 (2H, m), 7.27-7.42 (4H, m), 7.59-7.62 (2H, m), 8.35 (1H, s), 10.41 (1H, t, J=5.7 Hz).

Step 4

The compound A-4 was subjected to the hydroxy deprotection reaction described in Step F of the paragraph [0088] to obtain compound A-5.

$^1$HNMR (DMSO-d$_6$) δ:1.41 (3H, d, J=6.3 Hz), 1.85-1.92 (1H, m), 1.50-1.75 (1H, m), 4.02-4.09 (3H, m), 4.28-4.34 (1H, m), 4.53 (2H, d, J=5.7 Hz), 4.64 (1H, dd, J=3.9 Hz, 12.6 Hz), 5.45 (1H, dd, J=3.6 Hz, 9.3 Hz), 7.06 (1H, ddd, J=2.7 Hz, 8.4 Hz, 8.4 Hz), 7.20-7.28 (1H, m), 7.35-7.42 (1H, m), 8.43 (1H, s), 10.37 (1H, t, J=6.0 Hz), 12.37 (1H, brs).

Reference Example 2

[Chemical Formula 146]

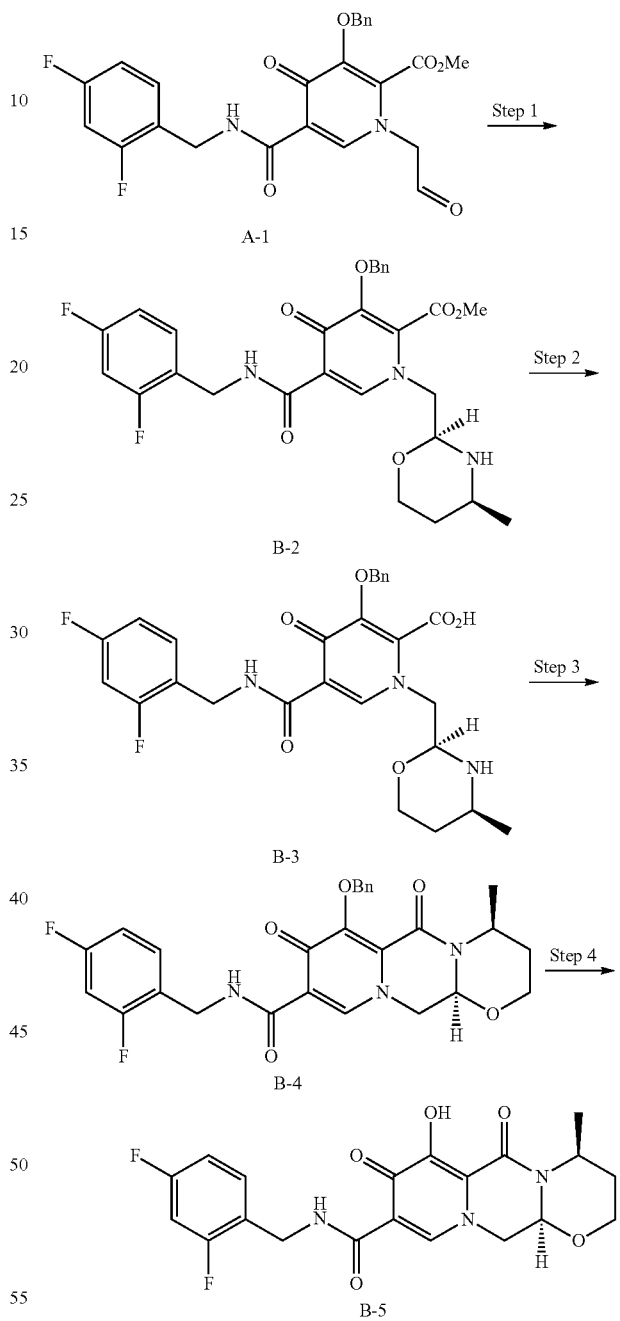

Compound A-1 was reacted with (S)-3-aminobutan-1-ol in Step 1. Compound B-5 was obtained in the same way as in Reference Example 1.

$^1$HNMR (DMSO-d$_6$) δ:1.41 (3H, d, J=6.3 Hz), 1.85-1.92 (1H, m), 1.50-1.75 (1H, m), 4.02-4.09 (3H, m), 4.28-4.34 (1H, m), 4.53 (2H, d, J=5.7 Hz), 4.64 (1H, dd, J=3.9 Hz, 12.6 Hz), 5.45 (1H, dd, J=3.6 Hz, 9.3 Hz), 7.06 (1H, ddd, J=2.7 Hz, 8.4 Hz, 8.4 Hz), 7.20-7.28 (1H, m), 7.35-7.42 (1H, m), 8.43 (1H, s), 10.37 (1H, t, J=6.0 Hz), 12.37 (1H, brs).

INDUSTRIAL APPLICABILITY

Use of the production method according to the present invention can reduce the number of steps for producing compounds having HIV integrase inhibitory activity from, for example, conventionally required 16 to 11 steps to preferably 8 to 6 steps. Thus, the production method of the present invention is applicable as an efficient industrial production method and as such, has industrial applicability.

What is claimed is:
1. A method of producing a compound shown by formula (Y2):

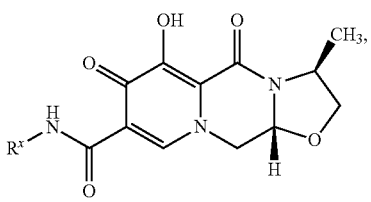

or a pharmaceutically acceptable salt thereof,
wherein:
$R^x$ is carbocyclyl optionally substituted by substituent E, heterocyclyl optionally substituted by substituent E, carbocyclyl lower alkyl optionally substituted by substituent E, or heterocyclyl lower alkyl optionally substituted by substituent E, where substituent E is as defined below;
comprising the following steps:
(Step C)
reacting a compound shown by formula (X3),

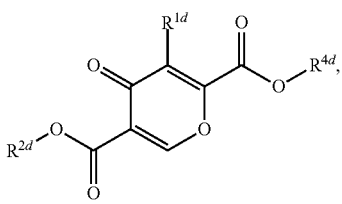

wherein:
$R^{1d}$ is hydrogen, halogen, lower alkyloxy optionally substituted by substituent E, carbocyclyl lower alkyloxy optionally substituted by substituent E, heterocyclyl lower alkyloxy optionally substituted by substituent E, or —OSi($R^{1e}$)$_3$, where substituent E is as defined below;
each $R^{1e}$ is independently lower alkyl optionally substituted by substituent E, carbocyclyl optionally substituted by substituent E, heterocyclyl optionally substituted by substituent E, carbocyclyl lower alkyl optionally substituted by substituent E, or heterocyclyl lower alkyl optionally substituted by substituent E, where substituent E is as defined below;
$R^{2d}$ is hydrogen, lower alkyl optionally substituted by substituent E, carbocyclyl lower alkyl optionally substituted by substituent E, or heterocyclyl lower alkyl optionally substituted by substituent E, where substituent E is as defined below; and $R^{4d}$ is lower alkyl optionally substituted by substituent E, carbocyclyl lower alkyl optionally substituted by substituent E, or heterocyclyl lower alkyl optionally substituted by substituent E, where substituent E is as defined below;
with a compound shown by formula (V3):

wherein:
$R^{6d}$ is lower alkyl optionally substituted by substituent E, or lower alkenyl optionally substituted by substituent E, where substituent E is as defined below;
to obtain a compound shown by formula (X4):

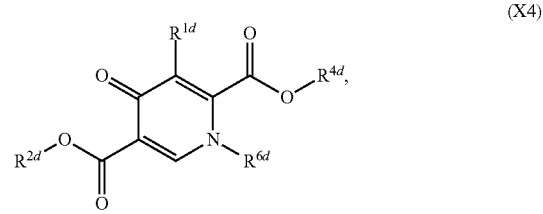

wherein:
$R^{1d}$ is hydrogen, halogen, lower alkyloxy optionally substituted by substituent E, carbocyclyl lower alkyloxy optionally substituted by substituent E, heterocyclyl lower alkyloxy optionally substituted by substituent E, or —OSi($R^{1e}$)$_3$, where substituent E is as defined below;
each $R^{1e}$ is independently lower alkyl optionally substituted by substituent E, carbocyclyl optionally substituted by substituent E, heterocyclyl optionally substituted by substituent E, carbocyclyl lower alkyl optionally substituted by substituent E, or heterocyclyl lower alkyl optionally substituted by substituent E, where substituent E is as defined below;
$R^{2d}$ is hydrogen, lower alkyl optionally substituted by substituent E, carbocyclyl lower alkyl optionally substituted by substituent E, or heterocyclyl lower alkyl optionally substituted by substituent E, where substituent E is as defined below;
$R^{4d}$ is lower alkyl optionally substituted by substituent E, carbocyclyl lower alkyl optionally substituted by substituent E, or heterocyclyl lower alkyl optionally substituted by substituent E, where substituent E is as defined below; and
$R^{6d}$ is lower alkyl optionally substituted by substituent E, or lower alkenyl optionally substituted by substituent E, where substituent E is as defined below;
(Step D)
reacting the compound shown by formula (X4) above with (S)-2-aminopropan-1-ol, to obtain a compound shown by formula (X5'):

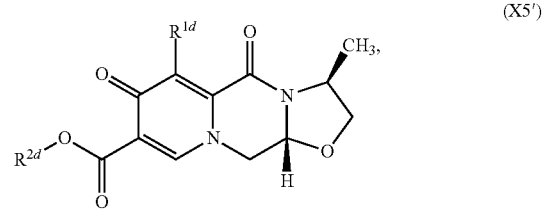

wherein:
- $R^{1d}$ is hydrogen, halogen, lower alkyloxy optionally substituted by substituent E, carbocyclyl lower alkyloxy optionally substituted by substituent E, heterocyclyl lower alkyloxy optionally substituted by substituent E, or —OSi($R^{1e}$)$_3$, where substituent E is as defined below;
- each $R^{1e}$ is independently lower alkyl optionally substituted by substituent E, carbocyclyl optionally substituted by substituent E, heterocyclyl optionally substituted by substituent E, carbocyclyl lower alkyl optionally substituted by substituent E, or heterocyclyl lower alkyl optionally substituted by substituent E, where substituent E is as defined below; and
- $R^{2d}$ is hydrogen, lower alkyl optionally substituted by substituent E, carbocyclyl lower alkyl optionally substituted by substituent E, or heterocyclyl lower alkyl optionally substituted by substituent E, where substituent E is as defined below;

(Step E)

reacting the compound shown by formula (X5') above with a compound of formula (V6):

$$H_2N-R^x \quad (V6)$$

wherein:
- $R^x$ is carbocyclyl optionally substituted by substituent E, heterocyclyl optionally substituted by substituent E, carbocyclyl lower alkyl optionally substituted by substituent E, or heterocyclyl lower alkyl optionally substituted by substituent E, where substituent E is as defined below;

to obtain a compound shown by formula (X6'):

(X6')

wherein:
- $R^{1d}$ is hydrogen, halogen, lower alkyloxy optionally substituted by substituent E, carbocyclyl lower alkyloxy optionally substituted by substituent E, heterocyclyl lower alkyloxy optionally substituted by substituent E, or —OSi($R^{1e}$)$_3$, where substituent E is as defined below;
- each $R^{1e}$ is independently lower alkyl optionally substituted by substituent E, carbocyclyl optionally substituted by substituent E, heterocyclyl optionally substituted by substituent E, carbocyclyl lower alkyl optionally substituted by substituent E, or heterocyclyl lower alkyl optionally substituted by substituent E, where substituent E is as defined below; and
- $R^x$ is carbocyclyl optionally substituted by substituent E, heterocyclyl optionally substituted by substituent E, carbocyclyl lower alkyl optionally substituted by substituent E, or heterocyclyl lower alkyl optionally substituted by substituent E, where substituent E is as defined below; and (Step F)

reacting the compound shown by formula (X6') above:
- (a) through hydroxyl deprotection, when $R^{1d}$ is lower alkyloxy optionally substituted by substituent E, carbocyclyl lower alkyloxy optionally substituted by substituent E, heterocyclyl lower alkyloxy optionally substituted by substituent E, or —OSi($R^{1e}$)$_3$, where substituent E is as defined below;
- (b) with $(CH_3)_3$—Si—I, $BBr_3$ or $BF_3.Et_2O$, when $R^{1d}$ is methyloxy;
- (c) with Pd—C/$H_2$ or Raney-Ni, when $R^{1d}$ is benzyloxy;
- (d) with $(CH_3)_4N^+F^-$, when $R^{1d}$ is —OSi($CH_3$)$_3$;
- (e) with $(CH_3)_3SiO^-K^+$ or $(CH_3)_3SiO^-Li^+$, followed by addition of aqueous mineral acid, when $R^{1d}$ is halogen; or
- (f) with a halogenating agent selected from the group consisting of N-bromosuccinimide, N-chlorosuccinimide and sulfuryl chloride, followed by addition of $(CH_3)_3SiO^-K^+$ or $(CH_3)_3SiO^-Li^+$ and aqueous mineral acid, when $R^{1d}$ is hydrogen;

to obtain the compound shown by formula (Y2) above, or a pharmaceutically acceptable salt thereof, wherein:
- substituent E is selected from the group consisting of halogen, cyano, hydroxy, carboxy, formyl, amino, oxo, nitro, lower alkyl, halogeno lower alkyl, lower alkyloxy, carbocyclyl optionally substituted by substituent F, heterocyclyl optionally substituted by substituent F, carbocyclyl lower alkyloxy optionally substituted by substituent F, heterocyclyl lower alkyloxy optionally substituted by substituent F, carbocyclyl lower alkylthio optionally substituted by substituent F, heterocyclyl lower alkylthio substituted by substituent F, carbocyclyl lower alkylamino optionally substituted by substituent F, heterocyclyl lower alkylamino optionally substituted by substituent F, carbocyclyloxy optionally substituted by substituent F, heterocyclyloxy optionally substituted by substituent F, carbocyclylcarbonyl optionally substituted by substituent F, heterocyclylcarbonyl optionally substituted by substituent F, carbocyclylaminocarbonyl optionally substituted by substituent F, heterocyclylaminocarbonyl optionally substituted by substituent F, halogeno lower alkyloxy, lower alkyloxy lower alkyl, lower alkyloxy lower alkyloxy, lower alkylcarbonyl, lower alkyloxycarbonyl, lower alkyloxycarbonylamino, lower alkylamino, lower alkylcarbonylamino, lower alkylaminocarbonyl, lower alkylsulfonyl and lower alkylsulfonylamino; and
- substituent F is selected from the group consisting of halogeno, hydroxy, carboxy, amino, oxo, nitro, lower alkyl, halogeno lower alkyl and lower alkyloxy.

2. The method according to claim 1, wherein $R^x$ is carbocyclyl lower alkyl optionally substituted by substituent E.

3. The method according to claim 1, wherein $R^x$ is 2,4-difluorobenzyl.

4. A method of producing a compound shown by formula (Y2):

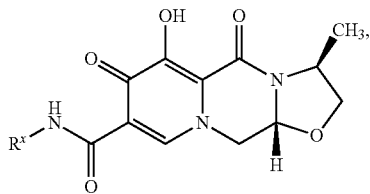

(Y2)

or a pharmaceutically acceptable salt thereof,
wherein:
R$^x$ is carbocyclyl optionally substituted by substituent E, heterocyclyl optionally substituted by substituent E, carbocyclyl lower alkyl optionally substituted by substituent E, or heterocyclyl lower alkyl optionally substituted by substituent E, where substituent E is as defined below;
comprising the following steps:
(Step C')
reacting a compound shown by formula (X4'):

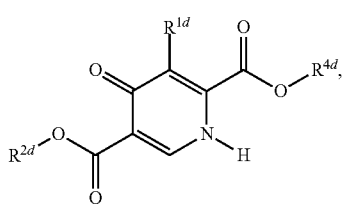

(X4')

wherein:
R$^{1d}$ is hydrogen, halogen, lower alkyloxy optionally substituted by substituent E, carbocyclyl lower alkyloxy optionally substituted by substituent E, heterocyclyl lower alkyloxy optionally substituted by substituent E, or —OSi(R$^{1e}$)$_3$, where substituent E is as defined below;
each R$^{1e}$ is independently lower alkyl optionally substituted by substituent E, carbocyclyl optionally substituted by substituent E, heterocyclyl optionally substituted by substituent E, carbocyclyl lower alkyl optionally substituted by substituent E, or heterocyclyl lower alkyl optionally substituted by substituent E, where substituent E is as defined below;
R$^{2d}$ is hydrogen, lower alkyl optionally substituted by substituent E, carbocyclyl lower alkyl optionally substituted by substituent E, or heterocyclyl lower alkyl optionally substituted by substituent E, where substituent E is as defined below; and
R$^{4d}$ is lower alkyl optionally substituted by substituent E, carbocyclyl lower alkyl optionally substituted by substituent E, or heterocyclyl lower alkyl optionally substituted by substituent E, where substituent E is as defined below;
with a compound shown by formula (V3'):

L$^d$-R$^{6d}$     (V3'), wherein:
L$^d$ is halogen, —OSO$_2$CH$_3$, —OSO$_2$CF$_3$, —OSO$_2$Ph or —OSO$_2$PhCH$_3$; and R$^{6d}$ is lower alkyl optionally substituted by substituent E, or lower alkenyl optionally substituted by substituent E, where substituent E is as defined below;
to obtain a compound shown by formula (X4):

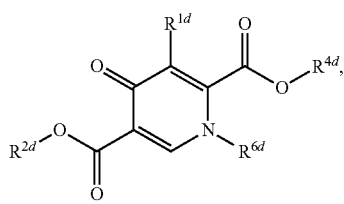

(X4)

wherein:
R$^{1d}$ is hydrogen, halogen, lower alkyloxy optionally substituted by substituent E, carbocyclyl lower alkyloxy optionally substituted by substituent E, heterocyclyl lower alkyloxy optionally substituted by substituent E, or —OSi(R$^{1e}$)$_3$, where substituent E is as defined below;
each R$^{1e}$ is independently lower alkyl optionally substituted by substituent E, carbocyclyl optionally substituted by substituent E, heterocyclyl optionally substituted by substituent E, carbocyclyl lower alkyl optionally substituted by substituent E, or heterocyclyl lower alkyl optionally substituted by substituent E, where substituent E is as defined below;
R$^{2d}$ is hydrogen, lower alkyl optionally substituted by substituent E, carbocyclyl lower alkyl optionally substituted by substituent E, or heterocyclyl lower alkyl optionally substituted by substituent E, where substituent E is as defined below;
R$^{4d}$ is lower alkyl optionally substituted by substituent E, carbocyclyl lower alkyl optionally substituted by substituent E, or heterocyclyl lower alkyl optionally substituted by substituent E, where substituent E is as defined below; and
R$^{6d}$ is lower alkyl optionally substituted by substituent E, or lower alkenyl optionally substituted by substituent E, where substituent E is as defined below;
(Step D)
reacting the compound shown by formula (X4) above with (S)-2-aminopropan-1-ol, to obtain a compound shown by formula (X5'):

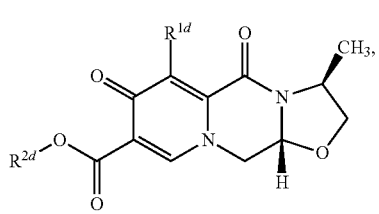

(X5')

wherein:
R$^{1d}$ is hydrogen, halogen, lower alkyloxy optionally substituted by substituent E, carbocyclyl lower alkyloxy optionally substituted by substituent E, heterocyclyl lower alkyloxy optionally substituted by substituent E, or —OSi(R$^{1e}$)$_3$, where substituent E is as defined below;

each $R^{1e}$ is independently lower alkyl optionally substituted by substituent E, carbocyclyl optionally substituted by substituent E, heterocyclyl optionally substituted by substituent E, carbocyclyl lower alkyl optionally substituted by substituent E, or heterocyclyl lower alkyl optionally substituted by substituent E, where substituent E is as defined below; and $R^{2d}$ is hydrogen, lower alkyl optionally substituted by substituent E, carbocyclyl lower alkyl optionally substituted by substituent E, or heterocyclyl lower alkyl optionally substituted by substituent E, where substituent E is as defined below;

(Step E)

reacting the compound shown by formula (X5') above with a compound of formula (V6):

$$H_2N-R^x \quad (V6),$$

wherein:

$R^x$ is carbocyclyl optionally substituted by substituent E, heterocyclyl optionally substituted by substituent E, carbocyclyl lower alkyl optionally substituted by substituent E, or heterocyclyl lower alkyl optionally substituted by substituent E, where substituent E is as defined below;

to obtain a compound shown by formula (X6'):

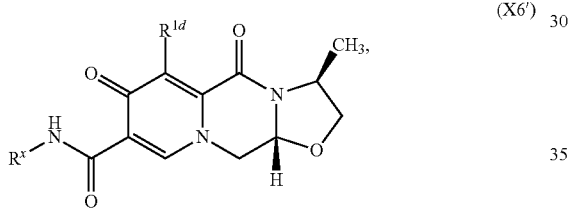

wherein:

$R^{1d}$ is hydrogen, halogen, lower alkyloxy optionally substituted by substituent E, carbocyclyl lower alkyloxy optionally substituted by substituent E, heterocyclyl lower alkyloxy optionally substituted by substituent E, or $-OSi(R^{1e})_3$, where substituent E is as defined below;

each $R^{1e}$ is independently lower alkyl optionally substituted by substituent E, carbocyclyl optionally substituted by substituent E, heterocyclyl optionally substituted by substituent E, carbocyclyl lower alkyl optionally substituted by substituent E, or heterocyclyl lower alkyl optionally substituted by substituent E, where substituent E is as defined below; and $R^x$ is carbocyclyl optionally substituted by substituent E, heterocyclyl optionally substituted by substituent E, carbocyclyl lower alkyl optionally substituted by substituent E, or heterocyclyl lower alkyl optionally substituted by substituent E, where substituent E is as defined below; and (Step F)

reacting the compound shown by formula (X6') above:

(a) through hydroxyl deprotection, when $R^{1d}$ is lower alkyloxy optionally substituted by substituent E, carbocyclyl lower alkyloxy optionally substituted by substituent E, heterocyclyl lower alkyloxy optionally substituted by substituent E, or $-OSi(R^{1e})_3$, where substituent E is as defined below;

(b) with $(CH_3)_3-Si-I$, $BBr_3$ or $BF_3.Et_2O$, when $R^{1d}$ is methyloxy;

(c) with $Pd-C/H_2$ or Raney-Ni, when $R^{1d}$ is benzyloxy;

(d) with $(CH_3)_4N^+F^-$, when $R^{1d}$ is $-OSi(CH_3)_3$;

(e) with $(CH_3)_3SiO^-K^+$ or $(CH_3)_3SiO^-Li^+$, followed by addition of aqueous mineral acid, when $R^{1d}$ is halogen; or (f) with a halogenating agent selected from the group consisting of N-bromosuccinimide, N-chlorosuccinimide and sulfuryl chloride, followed by addition of $(CH_3)_3SiO^-K^+$ or $(CH_3)_3SiO^-Li^+$ and aqueous mineral acid, when $R^{1d}$ is hydrogen;

to obtain the compound shown by formula (Y2) above, or a pharmaceutically acceptable salt thereof, wherein:

substituent E is selected from the group consisting of halogen, cyano, hydroxy, carboxy, formyl, amino, oxo, nitro, lower alkyl, halogeno lower alkyl, lower alkyloxy, carbocyclyl optionally substituted by substituent F, heterocyclyl optionally substituted by substituent F, carbocyclyl lower alkyloxy optionally substituted by substituent F, heterocyclyl lower alkyloxy optionally substituted by substituent F, carbocyclyl lower alkylthio optionally substituted by substituent F, heterocyclyl lower alkylthio substituted by substituent F, carbocyclyl lower alkylamino optionally substituted by substituent F, heterocyclyl lower alkylamino optionally substituted by substituent F, carbocyclyloxy optionally substituted by substituent F, heterocyclyloxy optionally substituted by substituent F, carbocyclylcarbonyl optionally substituted by substituent F, heterocyclylcarbonyl optionally substituted by substituent F, carbocyclylaminocarbonyl optionally substituted by substituent F, heterocyclylaminocarbonyl optionally substituted by substituent F, halogeno lower alkyloxy, lower alkyloxy lower alkyl, lower alkyloxy lower alkyloxy, lower alkylcarbonyl, lower alkyloxycarbonyl, lower alkyloxycarbonylamino, lower alkylamino, lower alkylcarbonylamino, lower alkylaminocarbonyl, lower alkylsulfonyl and lower alkylsulfonylamino; and substituent F is selected from the group consisting of halogeno, hydroxy, carboxy, amino, oxo, nitro, lower alkyl, halogeno lower alkyl and lower alkyloxy.

5. The method according to claim 4, wherein $R^x$ is carbocyclyl lower alkyl optionally substituted by substituent E.

6. The method according to claim 4, wherein $R^x$ is 2,4-difluorobenzyl.

7. The method according to claim 4, wherein Step C' is continuously performed.

* * * * *